United States Patent
Griffin et al.

(10) Patent No.: US 12,370,227 B1
(45) Date of Patent: Jul. 29, 2025

(54) FERMENTATE WITH ANTI-INFLAMMATORY AND IMMUNE MODULATING PROPERTIES

(71) Applicant: The Culture Club, LLC, West Hollywood, CA (US)

(72) Inventors: Michelle Griffin, Los Angeles, CA (US); Gitte S. Jensen, Klamath Falls, OR (US)

(73) Assignee: ITE Investments, LLC, Los Angeles, CA (US)

( * ) Notice: Subject to any disclaimer, the term of this patent is extended or adjusted under 35 U.S.C. 154(b) by 0 days.

(21) Appl. No.: 17/887,025

(22) Filed: Aug. 12, 2022

Related U.S. Application Data

(60) Provisional application No. 63/232,602, filed on Aug. 12, 2021.

(51) Int. Cl.
| | |
|---|---|
| *A61K 35/744* | (2015.01) |
| *A23K 10/18* | (2016.01) |
| *A61K 35/741* | (2015.01) |
| *A61K 36/06* | (2006.01) |
| *A61P 29/00* | (2006.01) |
| *A61P 37/02* | (2006.01) |

(52) U.S. Cl.
CPC ............ *A61K 35/744* (2013.01); *A23K 10/18* (2016.05); *A61K 35/741* (2013.01); *A61K 36/06* (2013.01); *A61P 29/00* (2018.01); *A61P 37/02* (2018.01)

(58) Field of Classification Search
CPC .... A61K 35/744; A61K 35/741; A61K 36/06; A23K 10/18; A61P 29/00; A61P 37/02
See application file for complete search history.

(56) References Cited

U.S. PATENT DOCUMENTS

| | | | | |
|---|---|---|---|---|
| 8,840,942 | B2* | 9/2014 | Olver | A21B 3/15 |
| | | | | 426/243 |
| 2010/0119653 | A1* | 5/2010 | Hall | A23L 19/00 |
| | | | | 426/62 |
| 2015/0335688 | A1* | 11/2015 | Coulson | A61K 31/205 |
| | | | | 424/93.3 |

FOREIGN PATENT DOCUMENTS

| | | | | |
|---|---|---|---|---|
| CA | 2204634 C | * | 5/2007 | .............. A21D 2/38 |
| CN | 105725012 A | * | 7/2016 | |
| CN | 106064991 A | * | 11/2016 | |
| CN | 111202205 A | * | 5/2020 | |
| FR | 2972728 A1 | * | 9/2012 | ............. A21D 8/047 |
| WO | WO-2014169079 A2 | * | 10/2014 | ........... C12M 45/09 |

OTHER PUBLICATIONS

Yong et al. (Effect of Lactobacillus Fermentation on the Anti-Inflammatory Potential of Turmeric, J. Microbiol. Biotechnol. (2019), 29(10), 1561-1569). (Year: 2019).*
Crittenden et al. (In vitro fermentation of cereal dietary fibre carbohydrates by probiotic and intestinal bacteria, J Sci Food Agric. 82: 781-789 (published online: 2002)) (Year: 2002).*
Bruhn et al. (Fermentation of sugar kelp (*Saccharina latissima*)—effects on sensory properties, and content of minerals and metals, Journal of Applied Phycology (2019) 31:3175-3187). (Year: 2019).*
Simova et al. (Bacteriocin production by strain *Lactobacillus delbrueckii* ssp. *bulgaricus* BB18 during continuous prefermentation of yogurt starter culture and subsequent batch coagulation of milk, J Ind Microbiol Biotechnol (2008) 35:559-567). (Year: 2008).*
Kapoore et al., "Co-culturing microbial consortia: approaches for applications in biomanufacturing and bioprocessing", *Critical Reviews in Biotechnology*, Taylor & Francis Group, vol. 42, No. 1, 46-72, 2022.

* cited by examiner

*Primary Examiner* — Louise W Humphrey
*Assistant Examiner* — Alexander M Duryee
(74) *Attorney, Agent, or Firm* — Klarquist Sparkman, LLP

(57) ABSTRACT

A fermentation process is disclosed that produces an immunomodulatory product. The process includes combining a source of starch, a source of sugar, and a source of a trace mineral with probiotic microorganisms and fermenting aerobically and anaerobically, thereby producing an immunomodulatory product. Turmeric is added before or after fermentation. The immunomodulatory product is also disclosed. Also provided are uses of the immunomodulatory product, such as to decrease inflammation in a subject. These methods can include increasing function of natural killer cells, decreasing T cell activation, altering CD69 expression on immune cells, and/or altering cytokine expression in a subject.

15 Claims, 34 Drawing Sheets

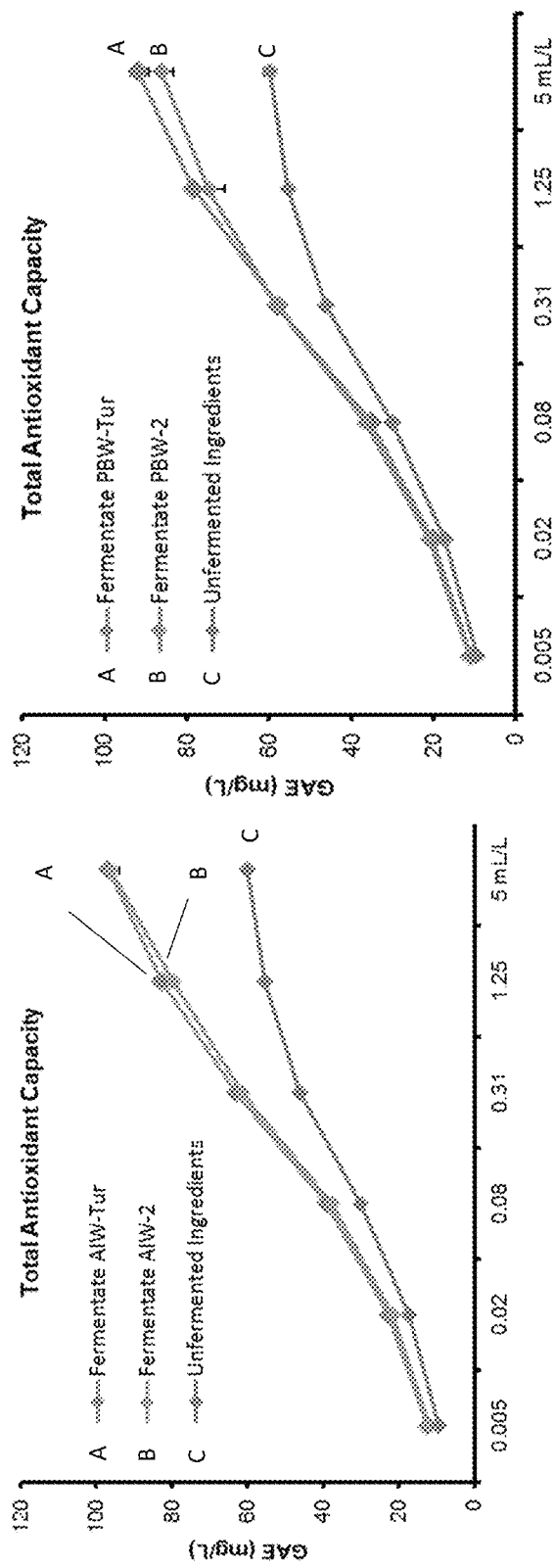

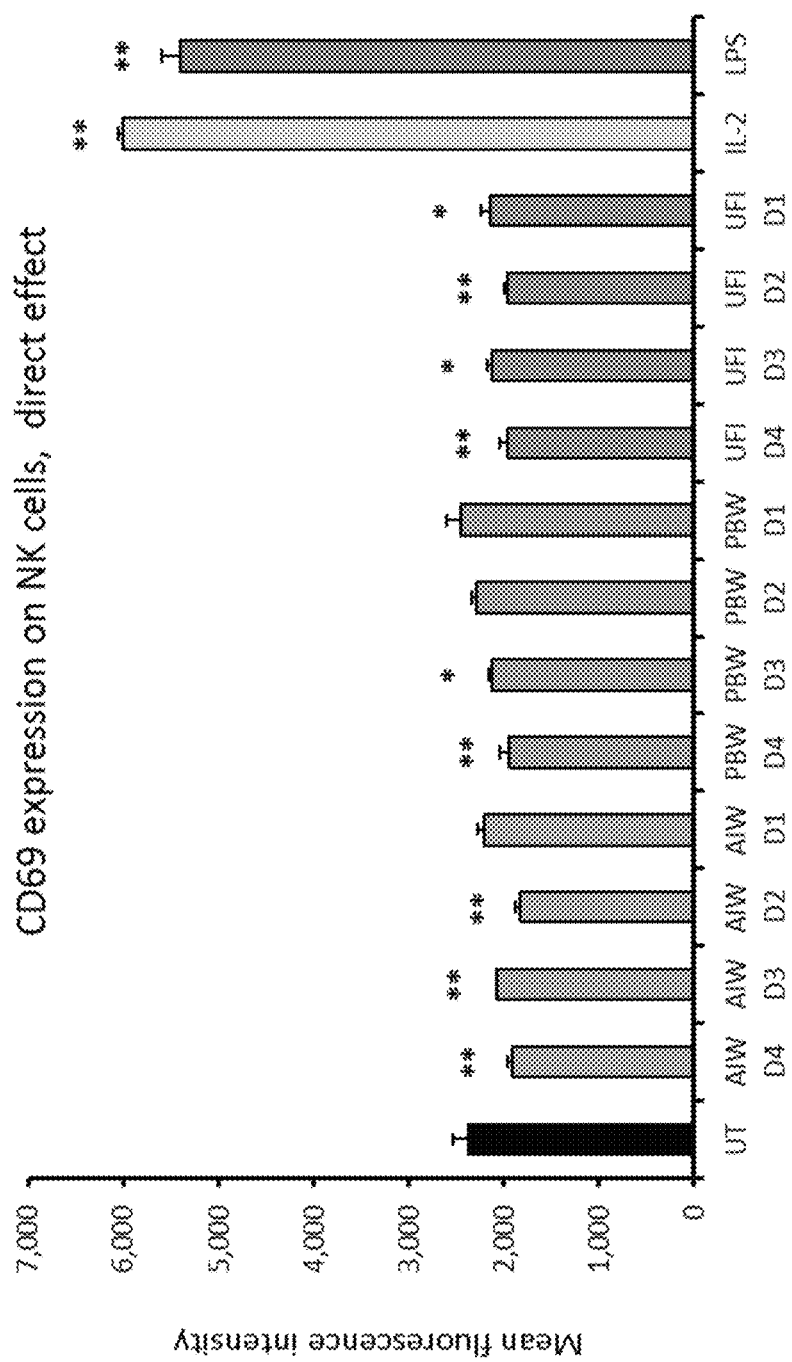

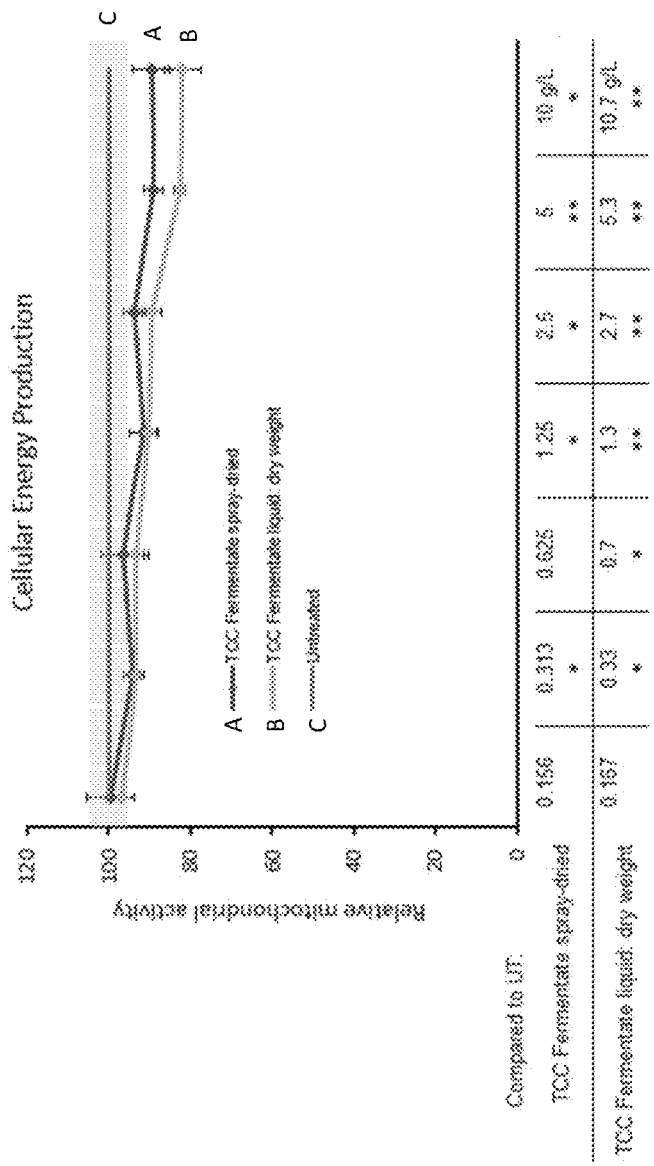

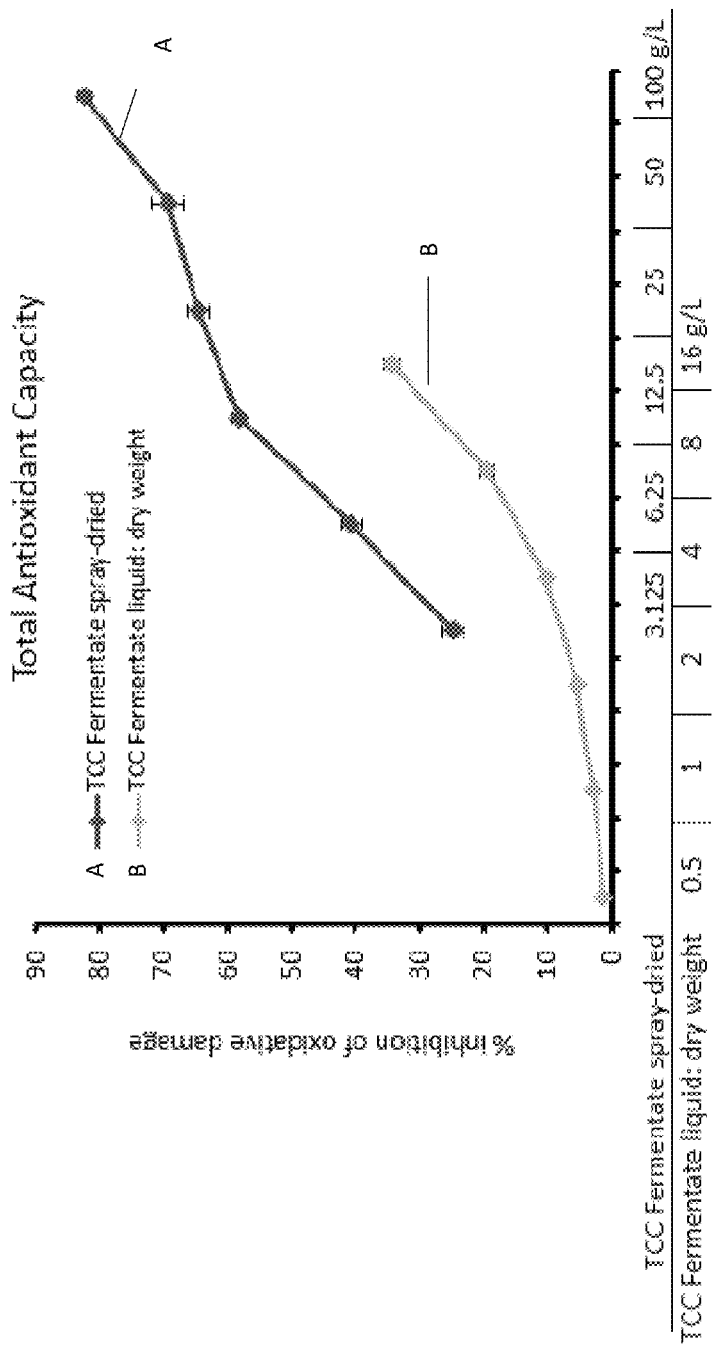

FERMENTATE WITH ANTI-INFLAMMATORY AND IMMUNE MODULATING PROPERTIES

CROSS REFERENCE TO RELATED APPLICATION

This claims the benefit of U.S. Provisional Application No. 63/232,602, filed Aug. 12, 2021, which is incorporated herein by reference in its entirety.

FIELD OF THE DISCLOSURE

This relates to the field of immunomodulatory products, specifically to products fermented from a source of starch, a source of sugar, and turmeric, with a probiotic bacteria and yeast, and their use to reduce inflammation.

BACKGROUND

Inflammation can be involved in the development of chronic diseases. Healthy dietary patterns, such as the Mediterranean diet (MD), may decrease the markers of inflammation. Healthy Nordic diet (HND) has many similarities with MD, but its effects on low grade inflammation are less well known. Both of these dietary patterns emphasize the abundant use of fruits and vegetables (and berries in HND), whole grain products, fish, and vegetable oil (canola oil in HND and olive oil in MD), but restrict the use of saturated fat and red and processed meat. There are several different biomarkers that are used for assessing inflammation in dietary studies. In these studies, the markers have been CRP, hsCRP, IL-6, IL-1 Ra, leptin, high-molecular weight adiponectin, TNF-$\alpha$, IL-1$\beta$, IL-10, TNF RII, and Chatepsin (see Lankinen et al., Nutrients 11 (6): 1369, 2019).

The antioxidant capacity of foods, juices, and teas has been linked to in vivo protection from oxidative stress in numerous studies. However, a need remains to identify products, fermented from natural sources, that can be used to reduce inflammation in subjects, and alter cytokine production.

SUMMARY OF THE DISCLOSURE

An immunomodulatory product produced by a fermentation process is provided herein. This fermentation process includes combining a source of starch, a source of sugar, and a source of a trace mineral with probiotic microorganisms to form a slurry. In some embodiments, the slurry includes turmeric. The slurry is fermented aerobically, to form an aerobic fermentate. In some embodiments, an effective amount of stabilizer and a second source of a trace mineral are added to the aerobic fermentate, thereby forming an intermediate composition. In some embodiments, turmeric is also added to the aerobic fermentate. The aerobic fermentate is then fermented anaerobically, to form the immunomodulatory product.

The immunomodulatory products disclosed herein demonstrate antioxidant and anti-inflammatory properties. In some embodiments, the immunomodulatory product includes a prebiotic, probiotic, and postbiotic. In some embodiments, the immunomodulatory product can be used, for example, as a nutraceutical. In some embodiments, animal feed is disclosed that includes the immunomodulatory product. The immunomodulatory product can be used to decrease inflammation in a subject.

Methods are disclosed for decreasing inflammation in a subject. These methods include administering to the subject an effective amount of an immunomodulatory product disclosed herein. These methods can increase function of natural killer cells, decrease T cell activation, alter CD69 expression on immune cells, and/or alter cytokine expression in the subject.

The foregoing and other features of the invention will become more apparent from the following detailed description of several embodiments which proceeds with reference to the accompanying figures.

BRIEF DESCRIPTION OF THE FIGURES

FIGS. 1A and 1B show total antioxidant capacity over a serial dilution of each sample. The average ±standard deviation of duplicate data points is shown. FIG. 1A shows the results for the two test products made using alkaline ionized water (AIW). FIG. 1B shows the results for the two test products produced using purified bottled water (PBW). All 4 test products (fermentates) showed better total antioxidant capacity than the unfermented ingredients. Thus, alkaline ionized water can be used in these processes, in addition to other types of water such as alkaline water, tap water, or spring water.

FIG. 4A shows the two test products with turmeric added prior to the fermentation process. FIG. 4B shows the two test products with turmeric added after the fermentation process. Statistical significance (p<0.05) is indicated by #, and a high level of significance (p<0.01) is indicated by ##.

FIG. 5 shows raw data for CD69 expression on NK cells. The data points represent the average±standard deviation of triplicate data sets. This demonstrates that treatment of immune cells with the fermentates activates NK cells to a higher level of alertness towards virus-infected or malignant cells.

11A) and solid fractions (FIG. 11B) of the test products. Results are shown as the average±standard deviation of duplicate samples.

Figure 12A:
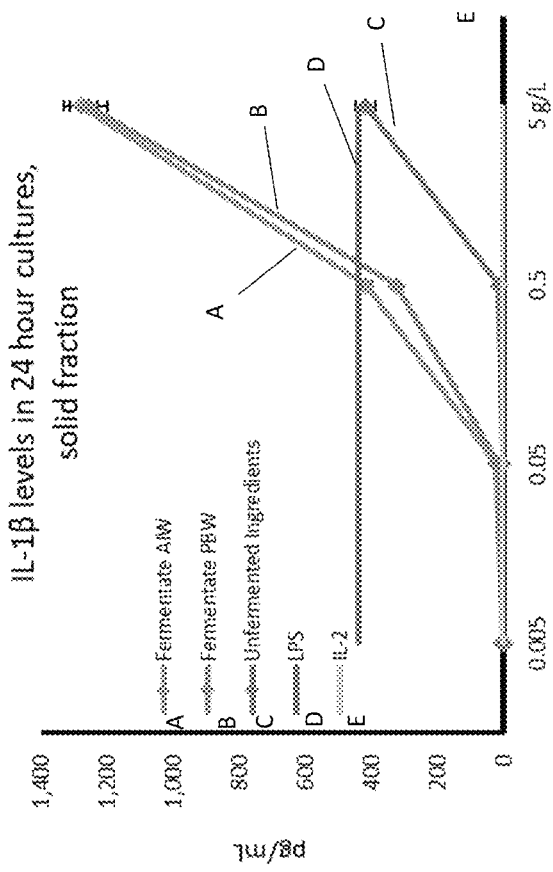
Figure 12B:
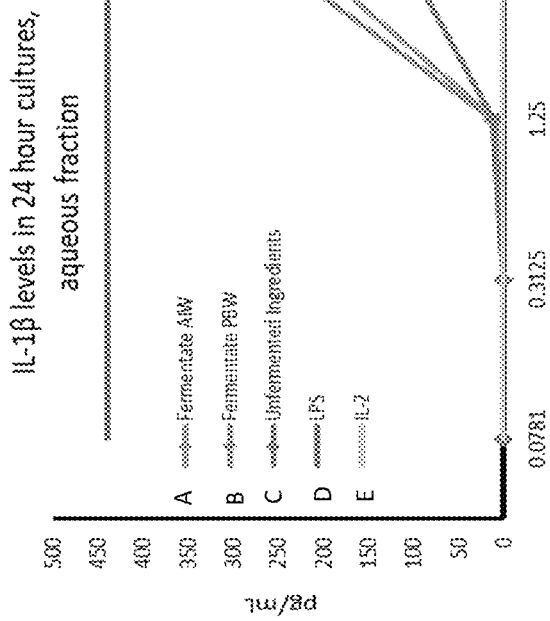

FIGS. 12A and 12B show interleukin 1 beta (IL-1β) levels in PBMC cultures treated with the aqueous fractions (FIG. 12A) and solid fractions (FIG. 12B) of the test products. Results are shown as the average±standard deviation of duplicate samples.

Figure 13A:
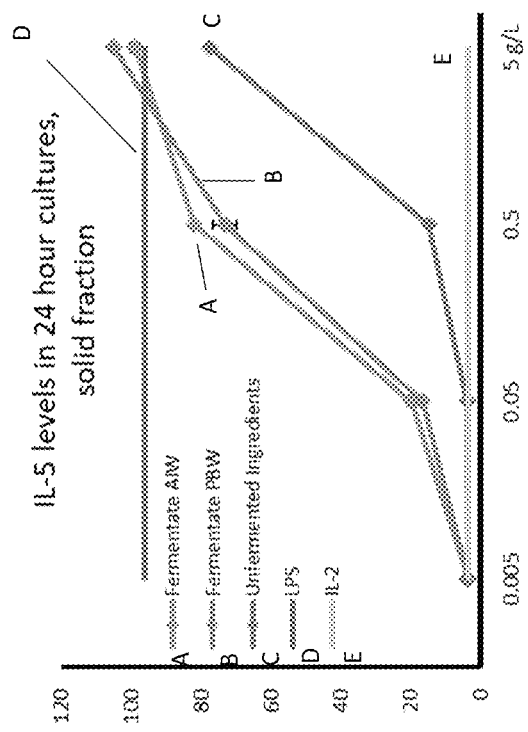
Figure 13B:
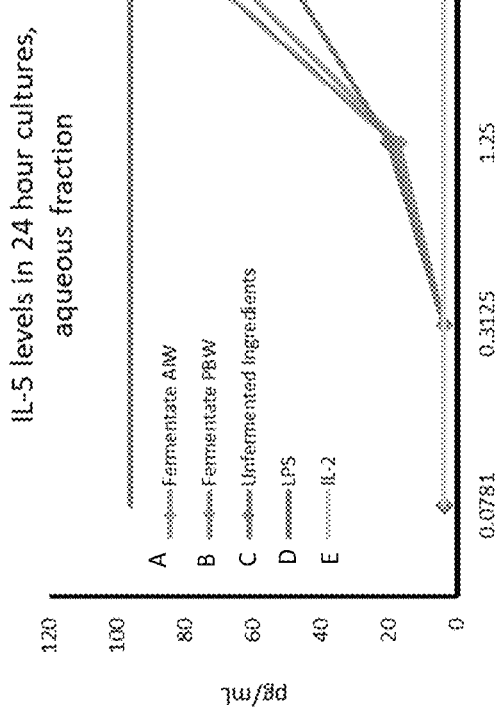

FIGS. 13A and 13B show interleukin 5 (IL-5) levels in PBMC cultures treated with the aqueous fractions (FIG. 13A) and solid fractions (FIG. 13B) of the test products. Results are shown as the average±standard deviation of duplicate samples.

Figure 14A:
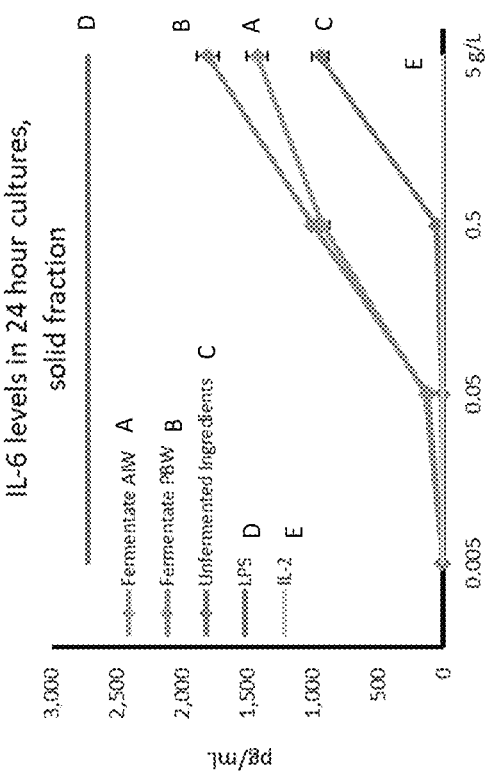
Figure 14B:
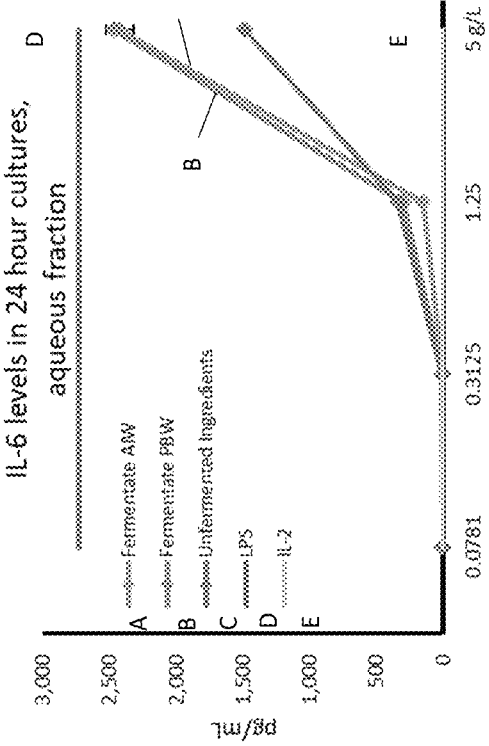

FIGS. 14A and 14B show interleukin 6 (IL-6) levels in PBMC cultures treated with the aqueous fractions (FIG. 14A) and solid fractions (FIG. 14B) of the test products. Results are shown as the average±standard deviation of duplicate samples.

Figure 15A:
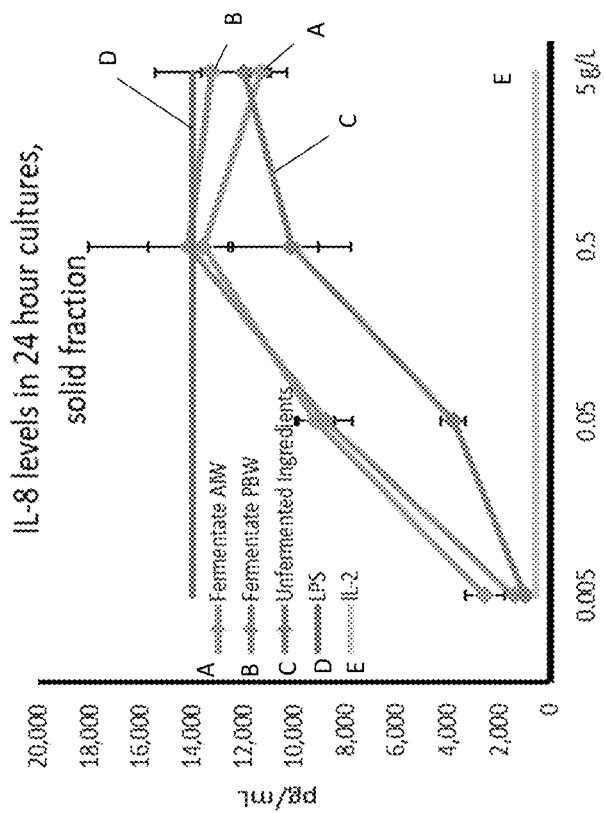
Figure 15B:
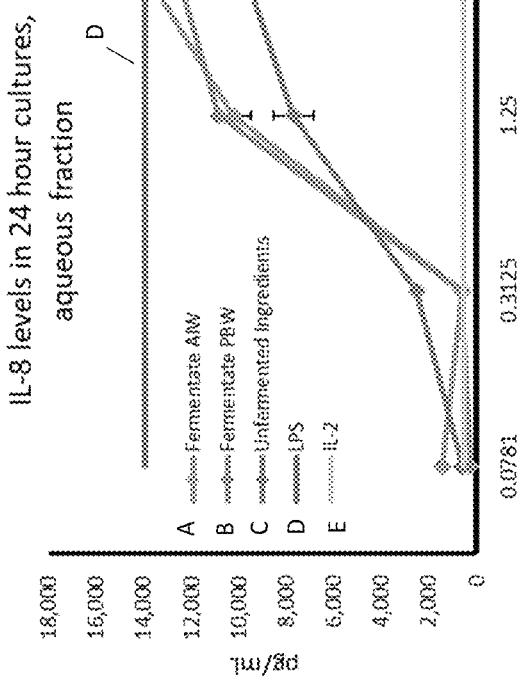

FIGS. 15A and 15B show interleukin 8 (IL-8) levels in PBMC cultures treated with the aqueous fractions (FIG. 15A) and solid fractions (FIG. 16B) of the test products. Results are shown as the average±standard deviation of duplicate samples.

Figure 16A:
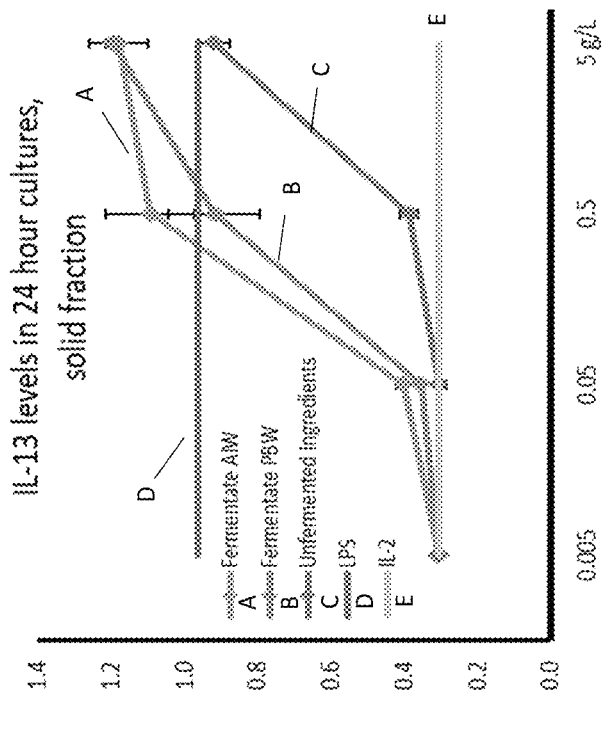
Figure 16B:
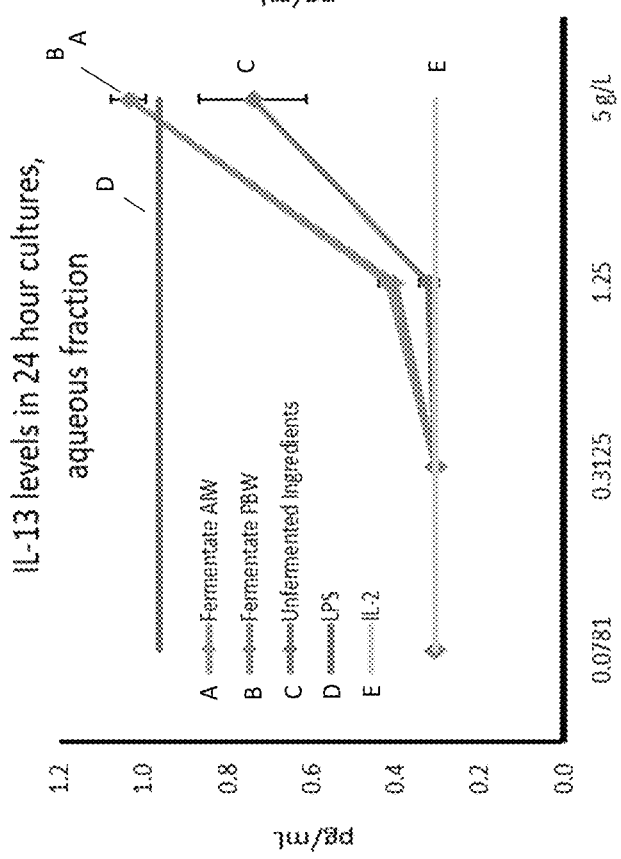

FIGS. 16A and 16B show interleukin 13 (IL-13) levels in PBMC cultures treated with the aqueous fractions (FIG. 16A) and solid fractions (FIG. 16B) of the test products. Results are shown as the average±standard deviation of duplicate samples.

Figure 17B:
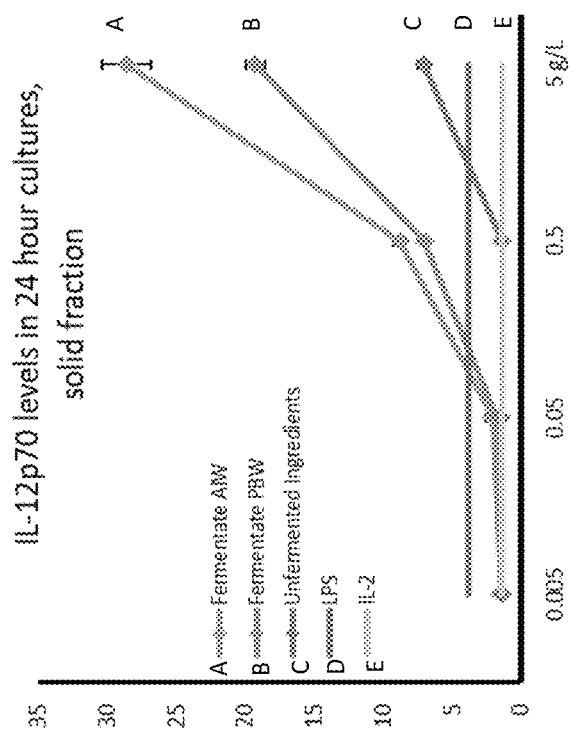
Figure 17A:
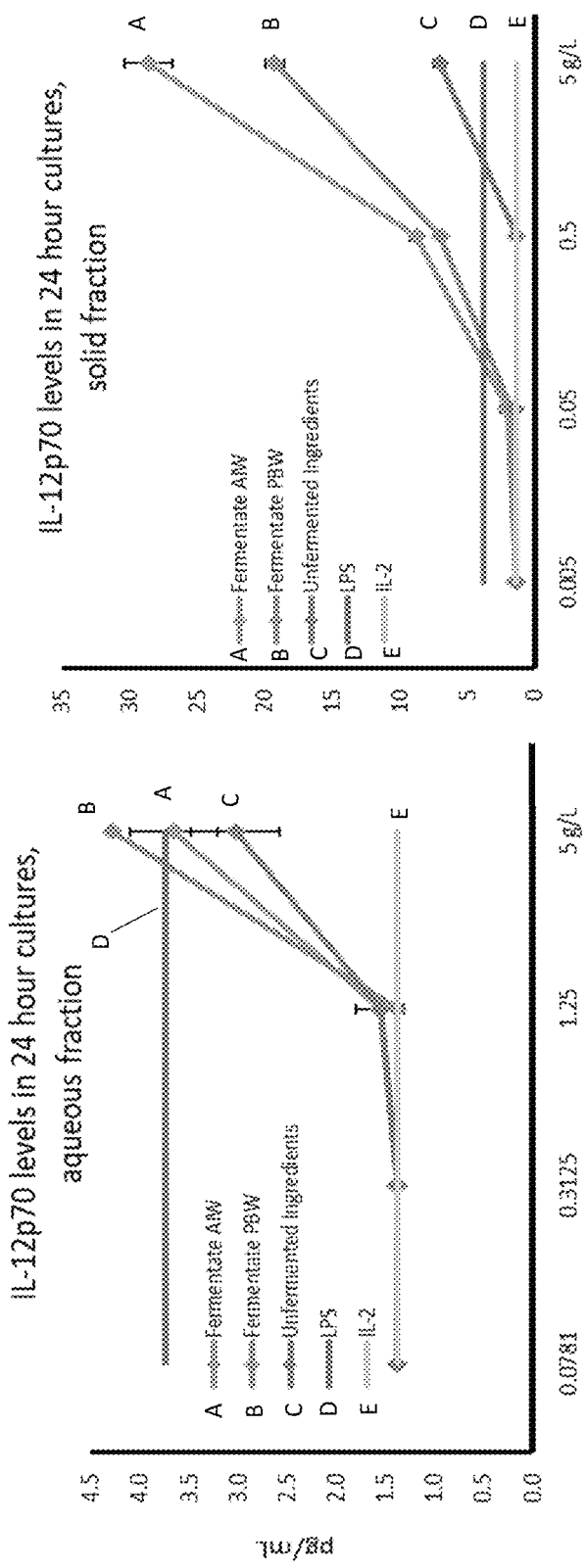

FIGS. 17A and 17B show interleukin 12 protein 70 (IL-12p70) levels in PBMC cultures treated with the aqueous fractions (FIG. 17A) and solid fractions (FIG. 17B) of the test products. Results are shown as the average±standard deviation of duplicate samples.

Figure 18A:
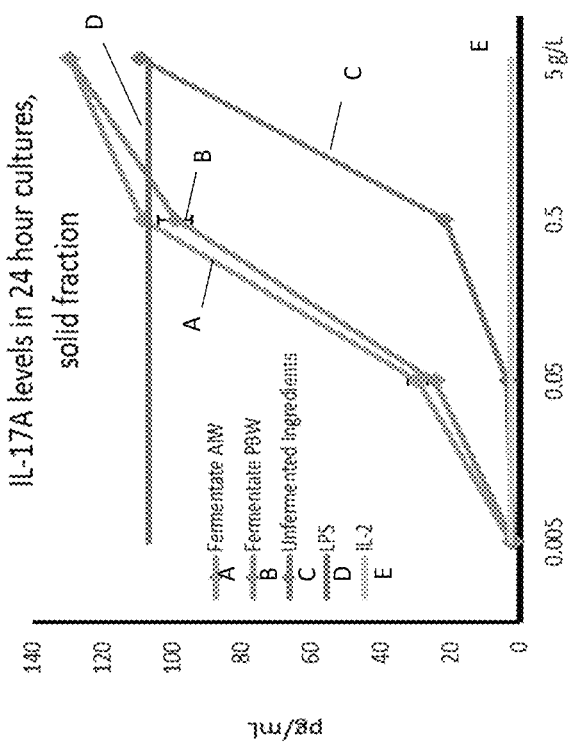
Figure 18B:
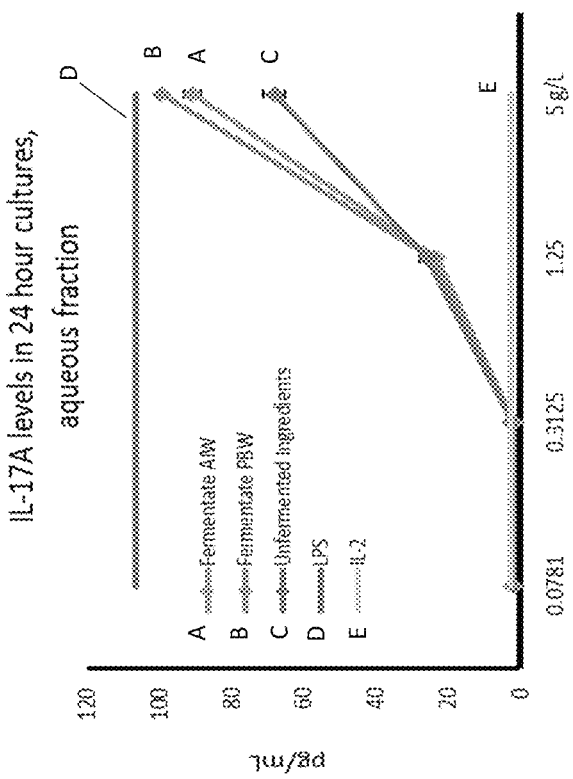

FIGS. 18A and 18B show interleukin 17A (IL-17A) levels in PBMC cultures treated with the aqueous fractions (FIG. 18A) and solid fractions (FIG. 18B) of the test products. Results are shown as the average±standard deviation of duplicate samples.

Figure 19A:
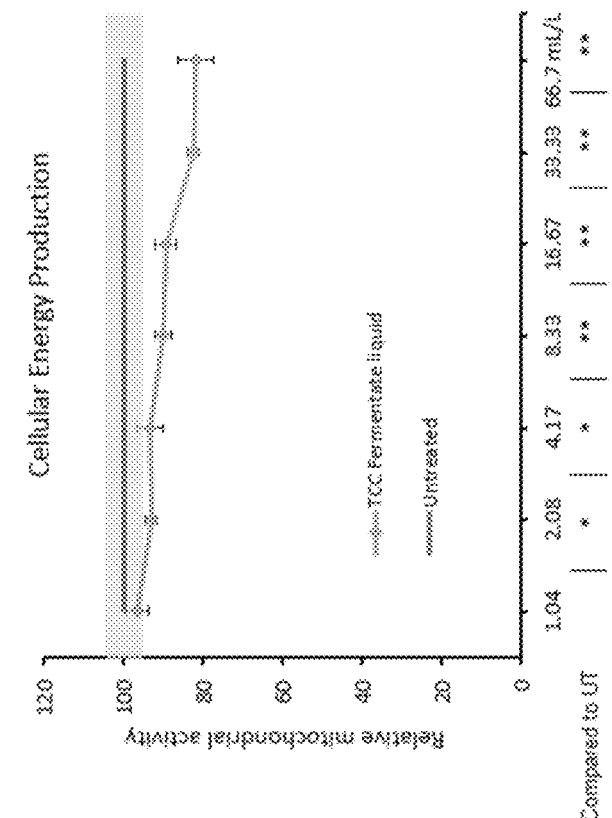
Figure 19B:
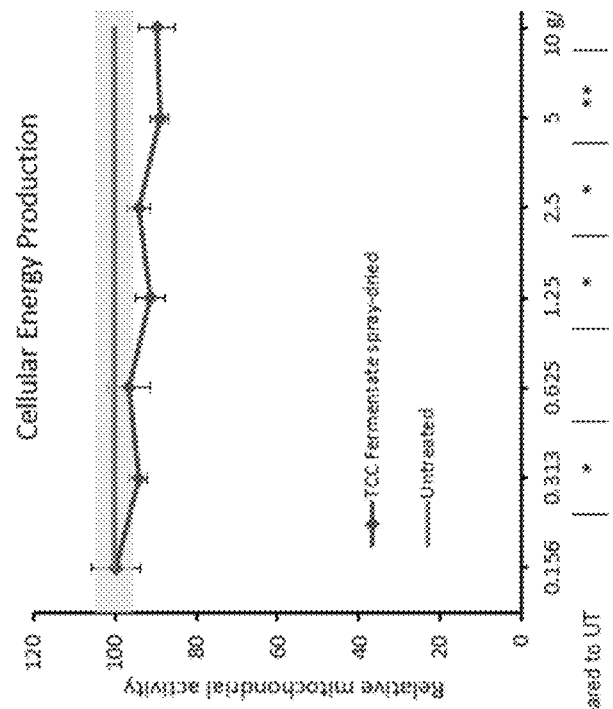

FIGS. 19A-19C show cellular energy production as a measure of relative mitochondrial metabolic activity. FIG. 19A shows PBMC cell culture treated with spray dried product. FIG. 19B shows PBMC cell culture treated with liquid product. FIG. 19C shows a comparison between the test products based on estimated dry weight. For FIGS. 19A-C, the solid line at 100% shows the average metabolic activity of untreated cells. The shaded area represents standard deviation for the untreated cells. Percent changes for treatments are shown as the average±standard deviation for each quadruplicate set of cell cultures, relative to the untreated cells. Statistical significance at different doses is indicated by asterisks, when P<0.10: (*), P<0.05: * and P<0.01: *.

Figure 20A:
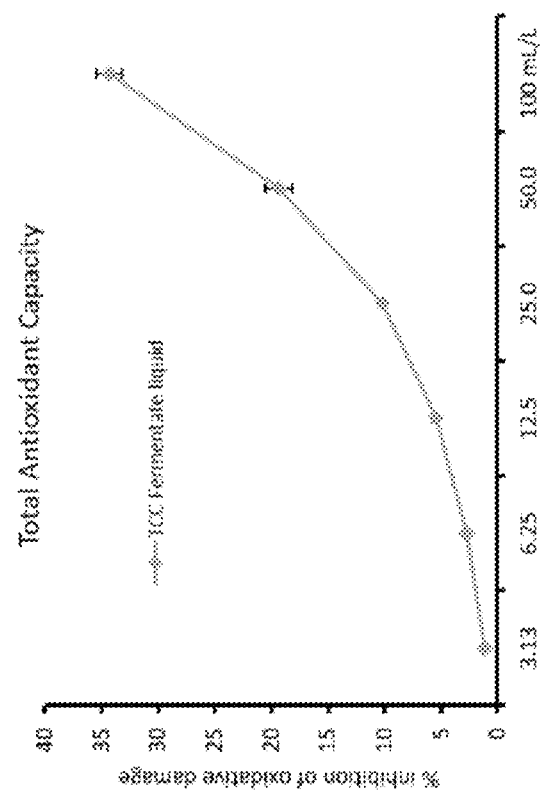
Figure 20B:
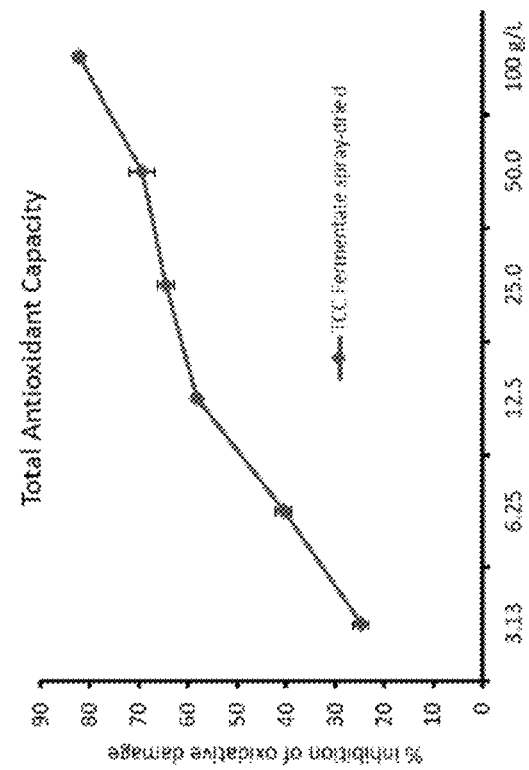

FIGS. 20A-20C show antioxidant capacity. FIG. 20A shows antioxidant capacity of the spray dried product. FIG. 20B shows antioxidant capacity of the liquid product. FIG. 20C shows a comparison between the test products based on estimated dry weight. The data shown is the average±standard deviation of duplicate data points for each dose.

Figure 21A:
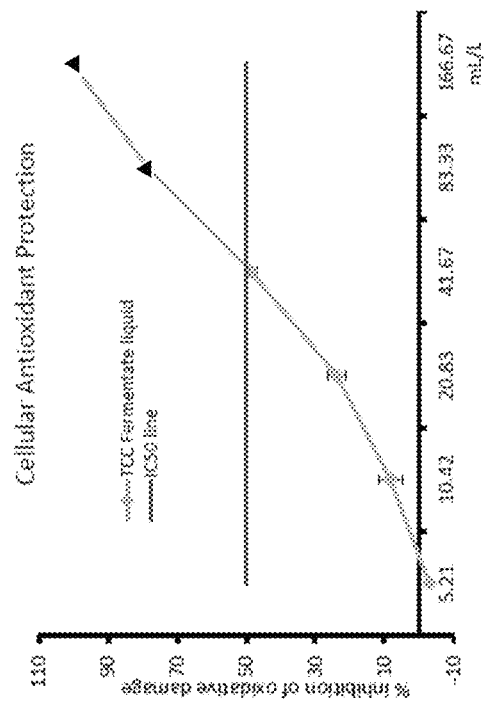
Figure 21B:
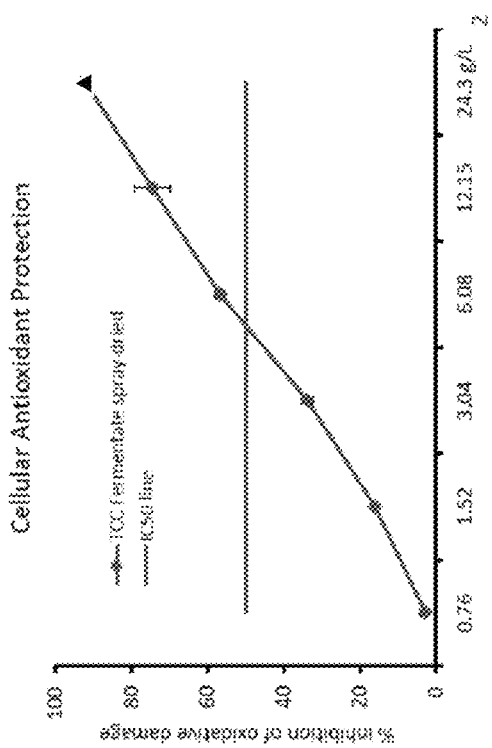
Figure 21C:
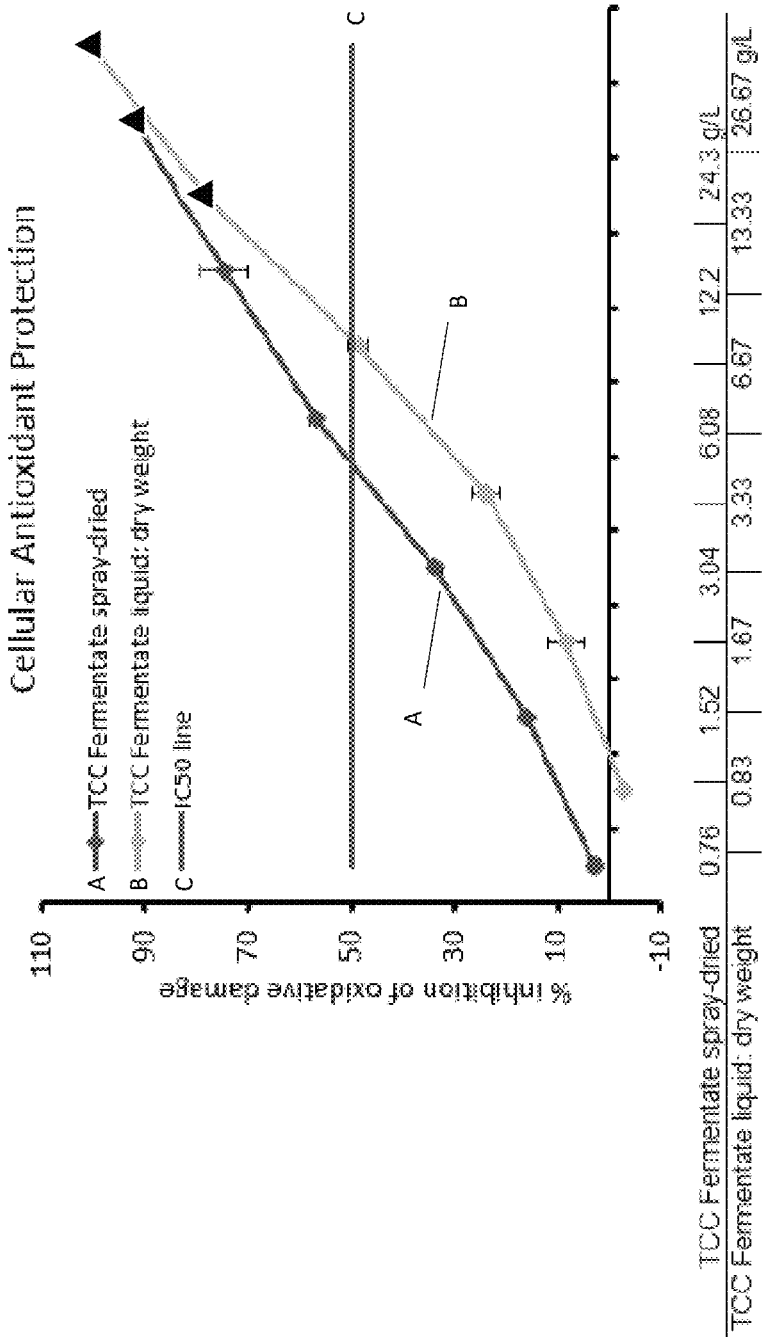

FIGS. 21A-21C show cellular antioxidant protection in red blood cells (RBCs). FIG. 21A shows cellular antioxidant protection of the spray dried product. FIG. 21B shows cellular antioxidant protection of the liquid product. FIG. 21C shows a comparison between the test products based on estimated dry weight. The data shown is the average±standard deviation of duplicate data points for each dose. The percent inhibition of cellular oxidative damage is shown as the average±standard deviation of duplicate data points for each dose of test product. Triangle markers indicate cell lysing.

Figure 22A:
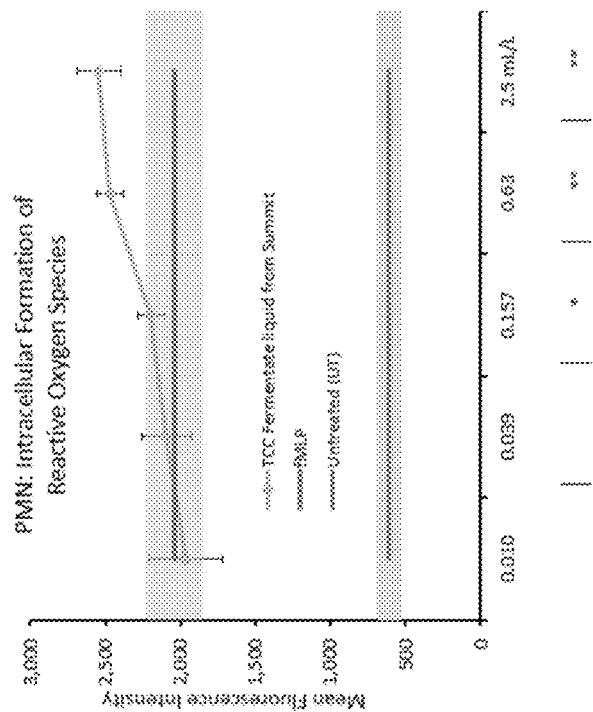
Figure 22B:
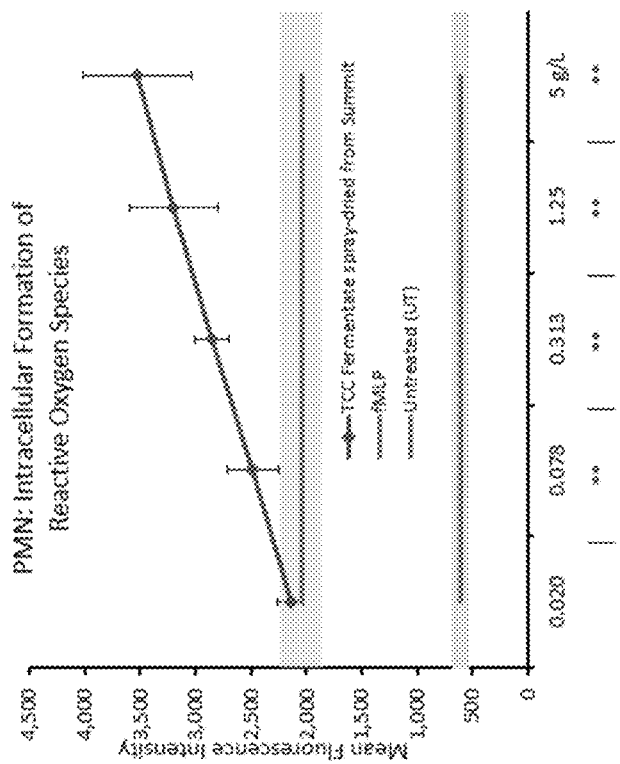
Figure 22C:
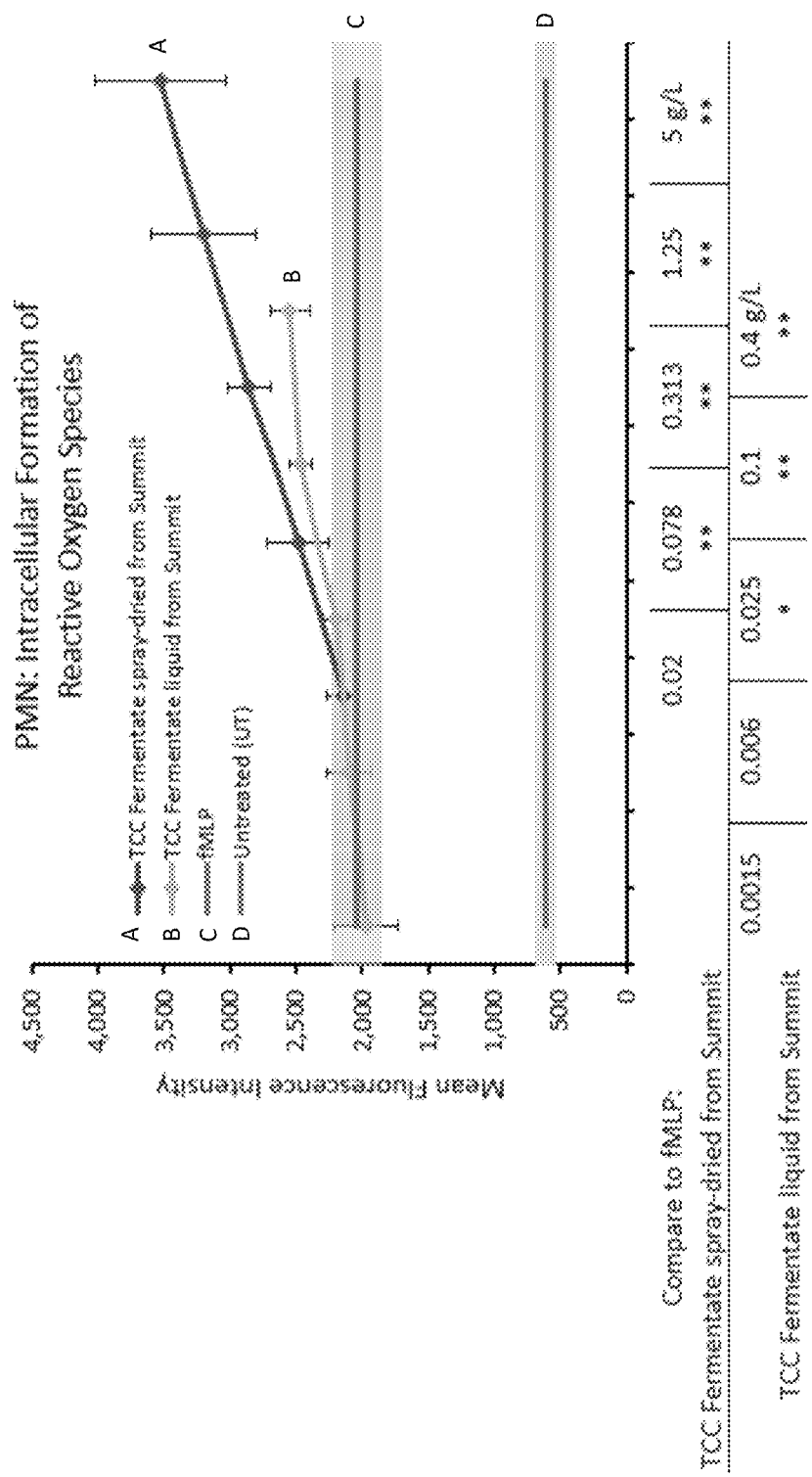
Figure 23A:
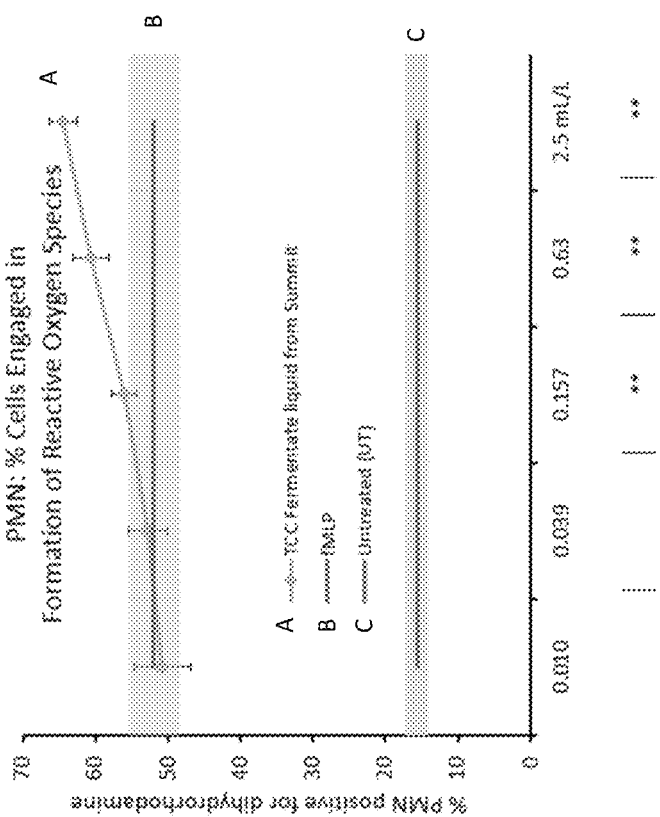
Figure 23B:
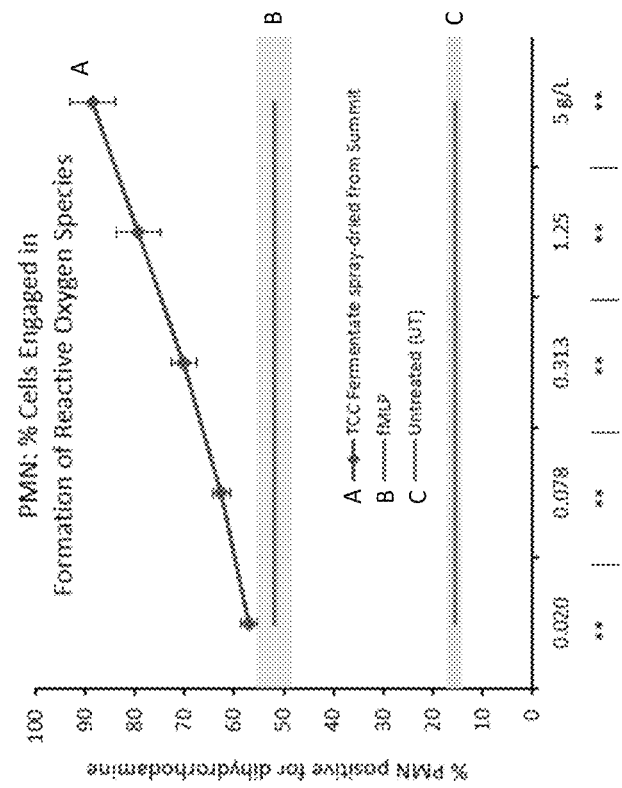
Figure 23C:
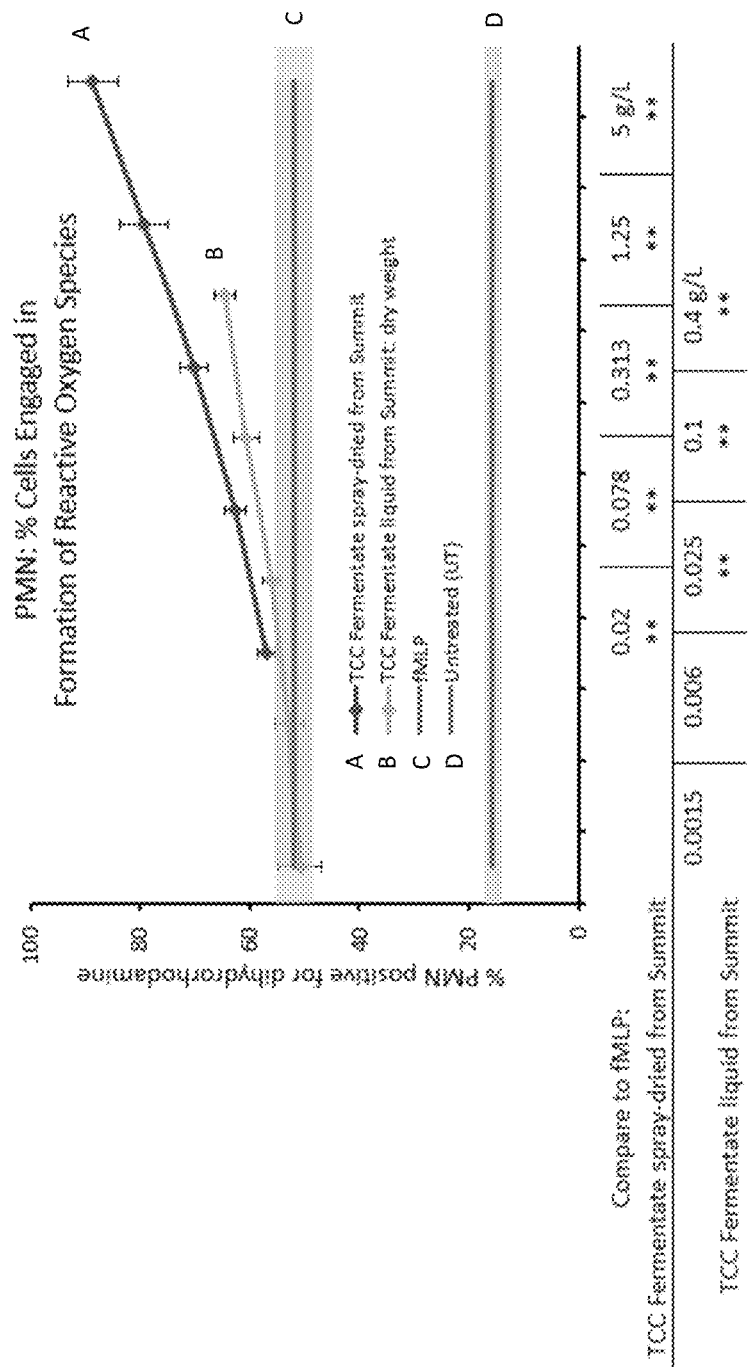

FIGS. 22A-22C show the effect of test products on the formation of reactive oxygen species (ROS) in polymorphonuclear (PMN) phagocytic cells. FIG. 22A shows ROS after incubation with the spray dried product. FIG. 22B shows ROS after incubation with the liquid product. FIG. 22C shows a comparison between the test products based on estimated dry weight. Shaded areas represent the standard deviation for untreated or fMLP treatments, respectively. The mean fluorescence intensity is shown as the average±standard deviation of sextuplicate data points for each dose of test product. Statistical significance (as compared to fMLP) at different doses is indicated by asterisks, when $p<0.10$: (*), $p<0.05$: * and $p<0.01$:

FIGS. 23A-23C show the effect of test products on the percent of PMN cells engaged in formation of reactive oxygen species (ROS). FIG. 23A shows % PMN cells positive for dihydrorhodamine (DHR) after incubation with the spray dried product. FIG. 23B shows % PMN cells positive for DHR after incubation with the liquid product. FIG. 23C shows a comparison between the test products based on estimated dry weight. Shaded areas represent the standard deviation for untreated or fMLP treatments, respectively. The mean fluorescence intensity is shown as the average±standard deviation of sextuplicate data points for each dose of test product. Statistical significance (as compared to fMLP) at different doses is indicated by asterisks, when $p<0.10$: (*), $p<0.05$: * and $p<0.01$: **.

Figure 24B:
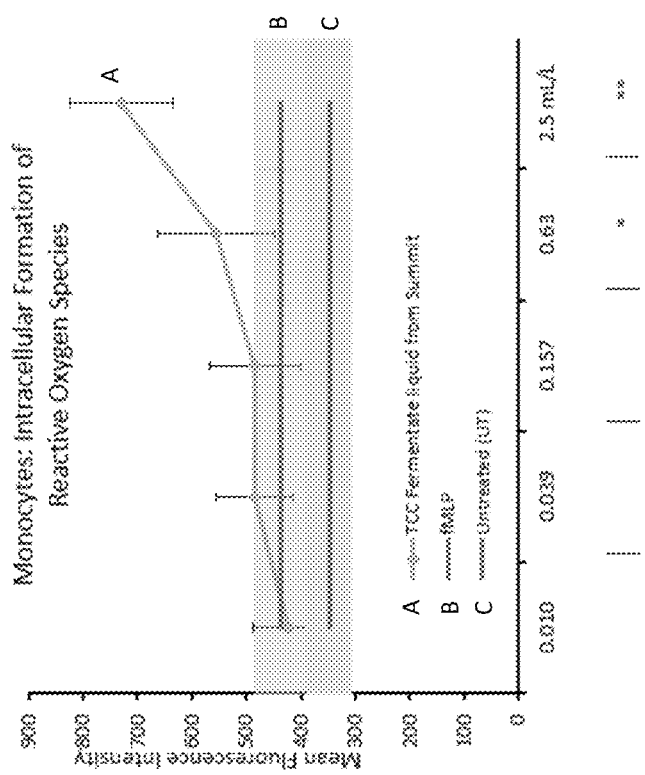
Figure 24A:
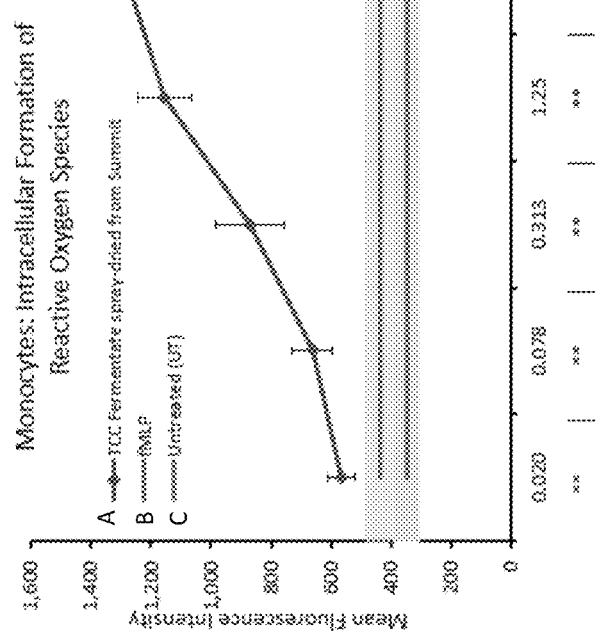
Figure 24C:
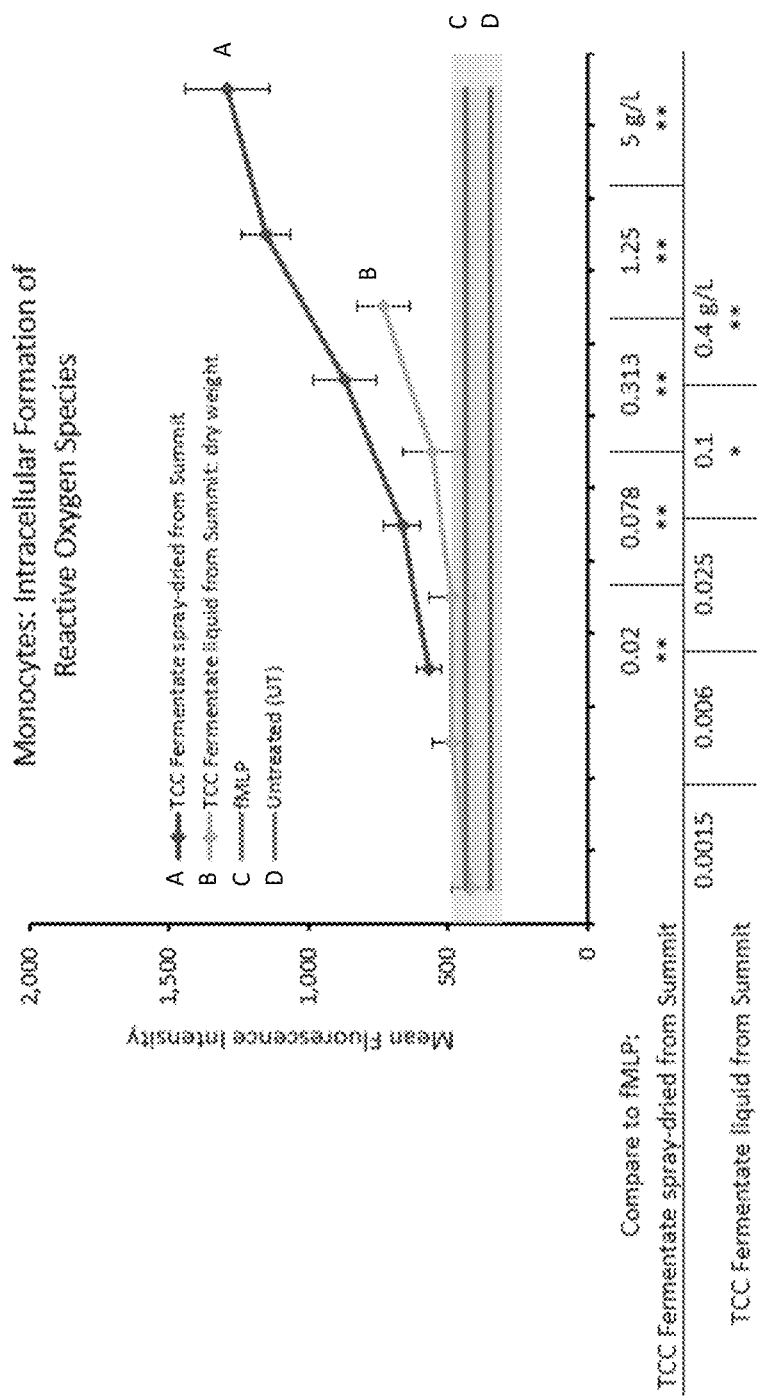

FIGS. 24A-24C show the effect of test products on intracellular formation of reactive oxygen species (ROS) in monocytes. FIG. 24A shows ROS after incubation with the spray dried product. FIG. 24B shows ROS after incubation with the liquid product. FIG. 24C shows a comparison between the test products based on estimated dry weight. Shaded areas represent the standard deviation for untreated or fMLP treatments, respectively. The mean fluorescence intensity is shown as the average±standard deviation of sextuplicate data points for each dose of test product. Statistical significance (as compared to fMLP) at different doses is indicated by asterisks, when $p<0.10$: (*), $p<0.05$: * and $p<0.01$: **.

Figure 25B:
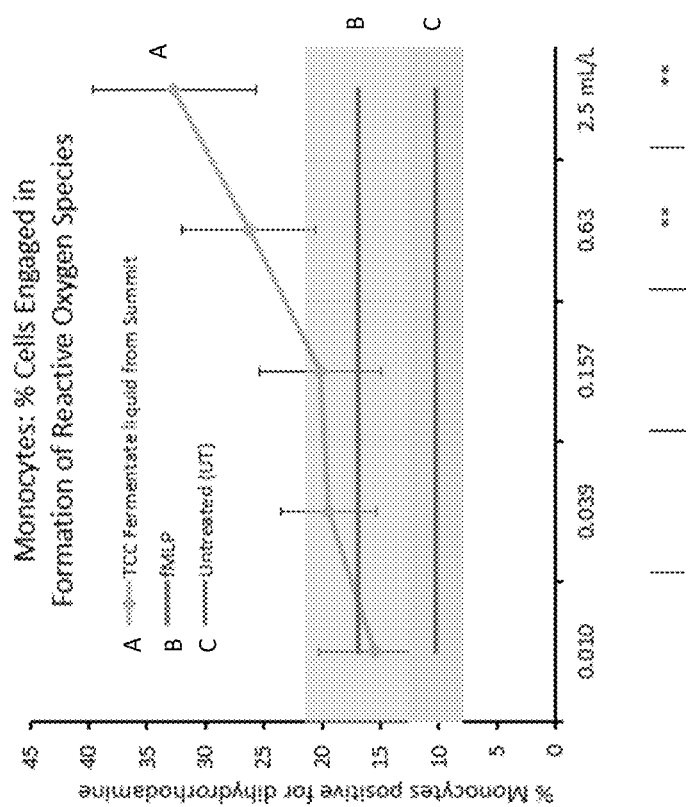
Figure 25A:
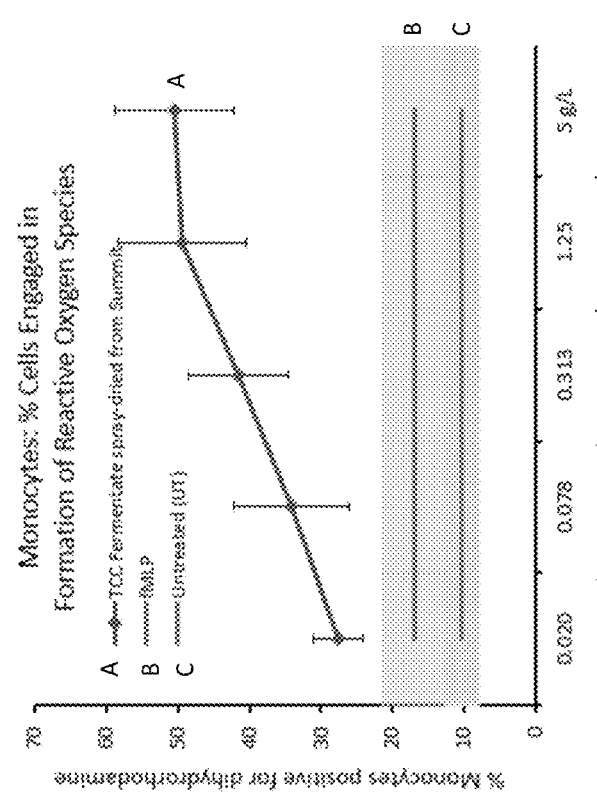
Figure 25C:
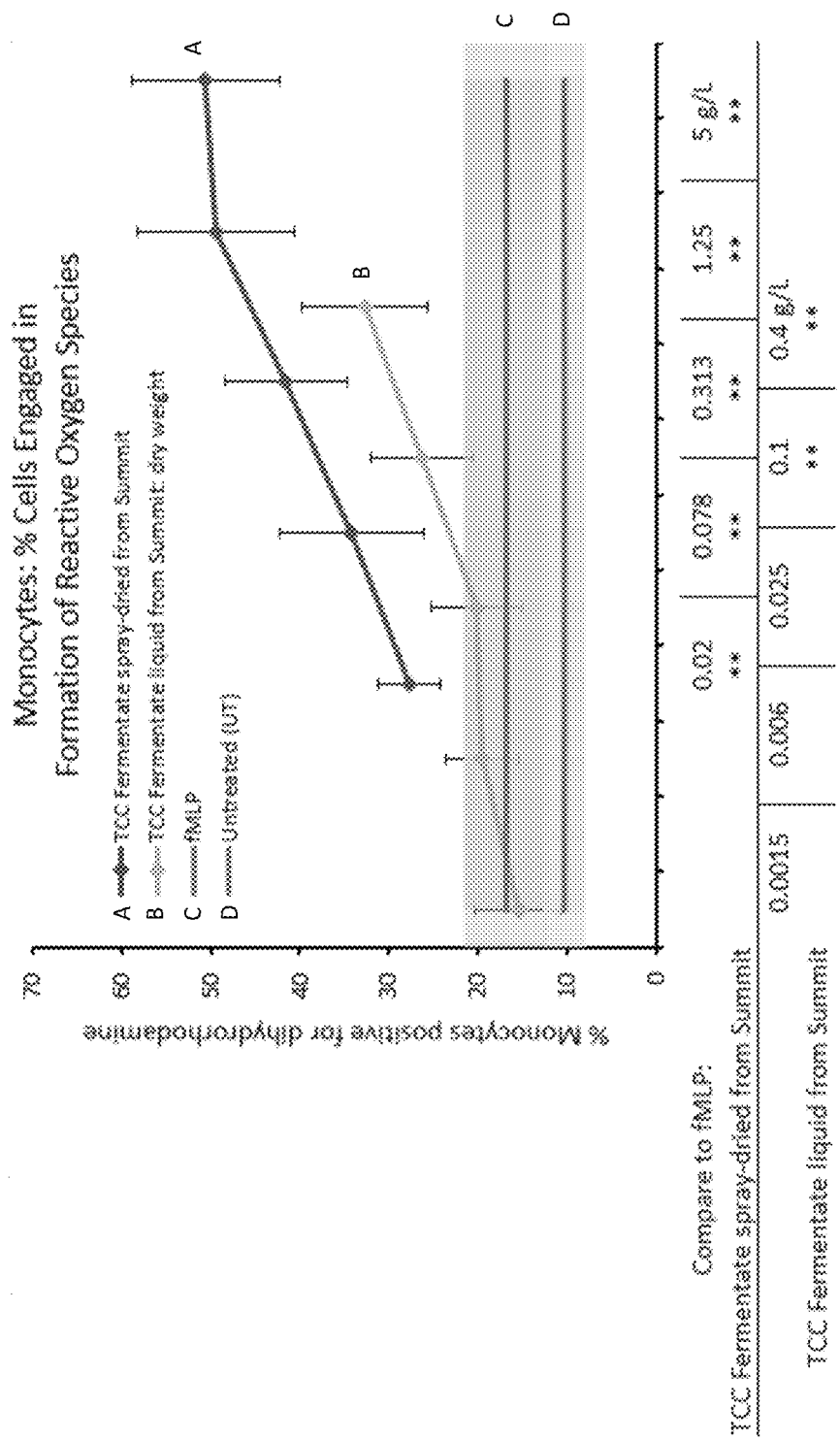
Figure 26A:
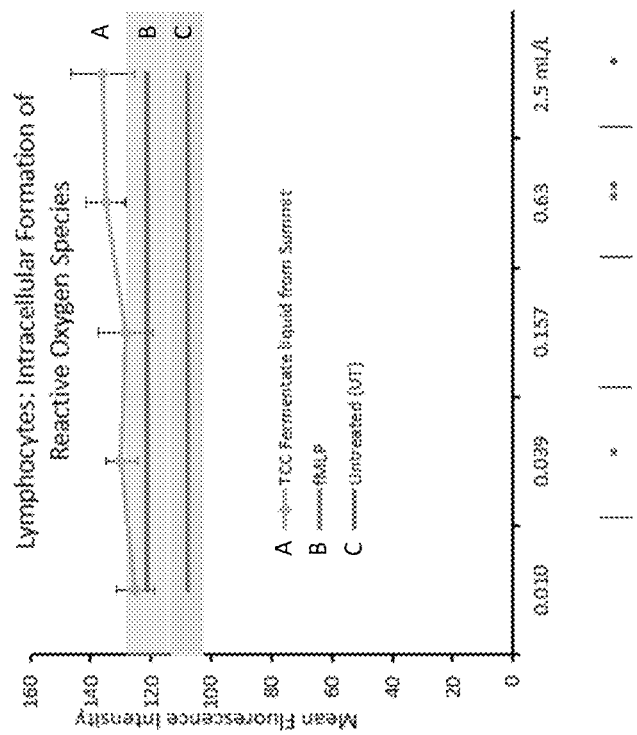
Figure 26B:
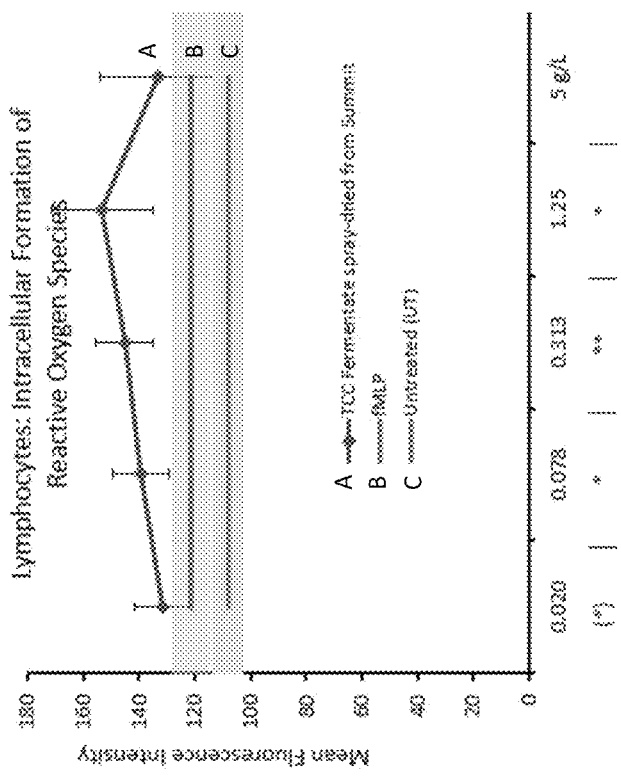
Figure 26C:
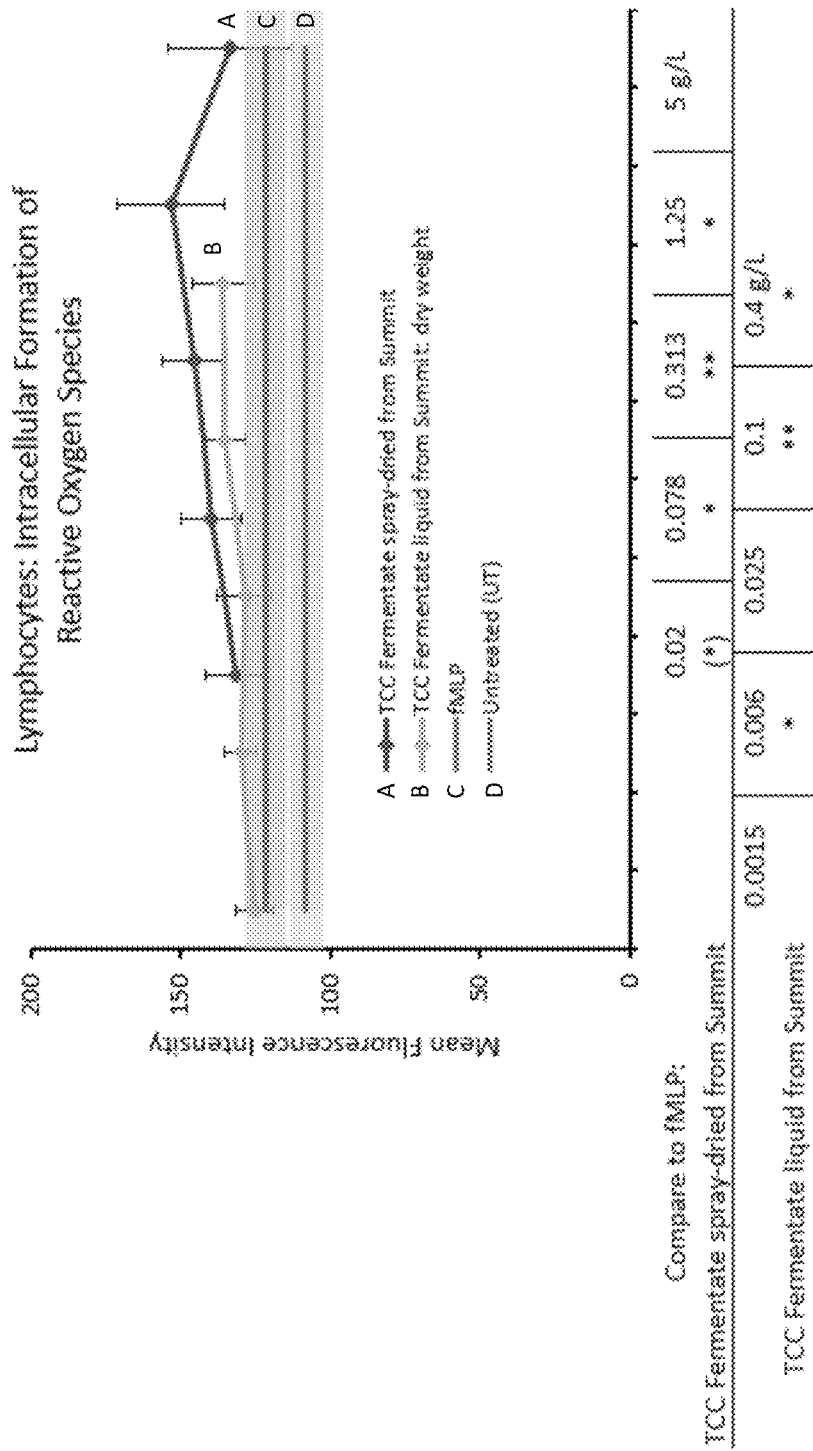

FIGS. 25A-25C show the effect of test products on the percent of monocyte cells engaged in formation of reactive oxygen species (ROS). FIG. 25A shows % monocyte cells positive for dihydrorhodamine (DHR) after incubation with the spray dried product. FIG. 25B shows % monocyte cells positive for DHR after incubation with the liquid product. FIG. 25C shows a comparison between the test products based on estimated dry weight. Shaded areas represent the standard deviation for untreated or fMLP treatments, respectively. The mean fluorescence intensity is shown as the average±standard deviation of sextuplicate data points for each dose of test product. Statistical significance (as compared to fMLP) at different doses is indicated by asterisks, when $p<0.10$: (*), $p<0.05$: * and $p<0.01$:

FIGS. 26A-26C show the effect of test products on formation of reactive oxygen species (ROS) by lymphocytes. FIG. 26A shows ROS after incubation with the spray dried product. FIG. 26B shows ROS after incubation with the liquid product. FIG. 26C shows a comparison between the test products based on estimated dry weight. Shaded areas represent the standard deviation for untreated or fMLP treatments, respectively. The mean fluorescence intensity is shown as the average±standard deviation of sextuplicate data points for each dose of test product. Statistical significance (as compared to fMLP) at different doses is indicated by asterisks, when $p<0.10$: (*), $p<0.05$: * and $p<0.01$:**.

DETAILED DESCRIPTION OF SEVERAL EMBODIMENTS

Disclosed herein are immunomodulatory products fermented from a source of starch, a source of sugar, and turmeric using a probiotic bacteria and yeast. These immunomodulatory products can be used to reduce inflammation. Methods for producing these immunomodulatory products are also disclosed.

I. Terms

The following explanations of terms and methods are provided to better describe the present disclosure and to guide those of ordinary skill in the art in the practice of the present disclosure. As used herein and in the appended claims, the singular forms "a" or "an" or "the" include plural references unless the context clearly dictates otherwise. As used herein, "comprises" means "includes." Thus, "comprising A or B." means "including A, B, or A and B," without excluding additional elements. It is further to be understood that any and all molecular weight or molecular mass values, given for specific molecules are approximate, and are provided for descriptive purposes, unless otherwise indicated.

Unless explained otherwise, all technical and scientific terms used herein have the same meaning as commonly understood to one of ordinary skill in the art to which this disclosure belongs. All percentages and ratios are calculated by weight unless otherwise indicated. Unless context indicates otherwise, the term "about" means plus or minus 10% of a reference value. For example, about 0.5L means 0.45 to 0.55L.

Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: To provide or give a subject an agent, such as an immunomodulatory product, by any effective route. Exemplary routes of administration include, but are not limited to, oral, injection (such as subcutaneous, intramuscular, intradermal, intraperitoneal, and intravenous), sublingual, transdermal, intranasal, topical, and inhalation routes. In some examples, administration is oral.

Aerobic: A reaction that takes place in the presence of oxygen.

Anaerobic: A reaction that takes place in the absence of oxygen.

Animal Feed: Food given to domestic animals or wild animals in captivity. Animal feed includes food (including treats) for pets (e.g., dogs, cats, hamsters, etc.) as well as for farm animals (e.g., pigs, cows, goats, rabbits, sheep, horses, chicken, etc.). In some examples. The animal feed is for a non-human mammal. In some examples, the animal feed is a food for dogs. In some examples, the animal feed is a food for cats.

Antioxidant: A substance that, when present in a mixture or structure containing an oxidizable substrate molecule (e.g., an oxidizable biological molecule or oxidizable indicator), significantly delays or prevents oxidation of the oxidizable substrate molecule. Antioxidants can act by scavenging biologically important reactive free radicals or other ROS or RNS, or by preventing their formation, or by catalytically converting the free radical or other ROS or RNS to a less reactive species. Cells have endogenous antioxidant machinery, which includes enzymes (such as superoxide dismutase, catalase, and glutathione peroxidase) and proteins (such as albumin, metallothionine, transferrin, ceruloplasmin, myoglobin, and ferritin). Additional antioxidants include compounds such as carotenoids (such as lutein, zeaxanthin, β-cryptoxanthin, lycopene, α-carotene, and β-carotene), tocopherols (such as vitamin E, α-tocopherol, γ-tocopherol, and δ-tocopherol), retinoids (such as vitamin A, retinol, and retinyl palmitate), and fat-soluble polyphenols such as quercetin. Antioxidants also include compounds such as ascorbic acid (vitamin C) and its oxidized form dehydroascorbic acid, uric acid and its oxidized form allantoin, bilirubin, albumin, isoflavones, procyanidins, and water-soluble polyphenols such as catechins.

Antioxidant activity: The ability of a compound to inhibit oxidative damage caused by free radicals or other ROS or RNS. The antioxidant activity of a test sample may be expressed relative to a known antioxidant, for example as TROLOX® equivalents (see, e.g., U.S. Pat. No. 7,132,296). The antioxidant activity of a compound may also be expressed as a percentage inhibition of oxidative damage, where oxidative damage is assessed by use of an indicator dye which becomes fluorescent upon oxidative damage (such as under conditions of oxidative stress). In some examples, antioxidant activity is measured by Folin-Ciocalteu assay.

Cluster of Differentiation (CD) 69: A human transmembrane C-Type lectin protein encoded by the CD69 gene that is an early activation marker that is expressed in hematopoietic stem cells, T cells, and many other cell types in the immune system. CD69 is also implicated in T cell differentiation as well as lymphocyte retention in lymphoid organs. Exemplary CD69 sequences are provided in GENBANK Accession No. NP_001772, Jun. 20, 2021 and GENBANK Accession No. NM_001781, Jun. 20, 2021, both incorporated by reference herein.

Collagen: The main structural protein found in skin and other connective tissues. It is important for the health of bones, skin, blood vessels, and all the body's organs. Low collagen levels can lead to joint problems and a lack of elasticity in the skin. Collagen supplements are often consumed to improve skin, hair or nail health, relieve joint pain, prevent bone loss (osteoporosis), increase muscle mass, or promote heart health. Collagen is most commonly derived from bovine, porcine, or marine sources. It can also be produced synthetically from insect, yeast, plant, or mammal cell culture, resulting in a lower risk of allergic reactions. Oral collagen supplements are typically sold as collagen peptides or hydrolyzed collagen, which are broken down forms of collagen that are more easily absorbed.

Colostrum: The first secretion from mammary glands after giving birth. Colostrum is a milk-like fluid that is rich in nutrients and antibodies. It is produced by mammals, including humans, cats, dogs, cows, horses, sheep, pigs, and goats. Colostrum is commercially available, for example, NURSEMATE®, a high performance bovine colostrum produced by Sterling Technology Bioactive Solutions (e.g., NURSEMATE®, NURSEMATE® ASAP, NURSEMATE® PLUS 150 with Immu-PRIME®, NURSEMATE® 50 with Immu-PRIMER, NURSEMATE® 100 with Immu-PRIME®).

Control: A reference standard. The control can be a negative or positive control. In some embodiments, the control is a historical control or a standard reference value (or range of values). Non-limiting examples of controls include untreated samples, or treatment with the unfermented ingredients (UFI). In some examples, the control is a treatment known to induce a particular response or outcome, for example, treatment with IL-2, LPS, or fMLP. In some examples, the control is a measurement prior to a treatment of interest, for example, measurements prior to treatment with (or administering) the immunomodulatory product disclosed herein.

Cytokine: A small protein (~5-20 kDa) involved in cell signaling. Cytokines have been shown to be involved in autocrine, paracrine and endocrine signaling as immunomodulating agents. Cytokines include chemokines, interferons, interleukins, lymphokines, and tumor necrosis factors, but are not hormones or growth factors. Cytokines are produced by immune cells such as macrophages, B lymphocytes, T lymphocytes, NK cells, and mast cells, as well as endothelial cells, fibroblasts, and various stromal cells. The "interleukins" are a type of cytokines that are divided into four groups based on distinguishing structural features. These included IL-1, 2, 3, 4, 5, 6, 7, 8, 9, 10, 11, 12, 13, 14, 15, 16 and 17.

Exemplary proinflammatory cytokines include, but are not limited to, IL-1-$\beta$, IL-5, IL-6, IL-8, IL-12 protein 70 (IL-12p70), IL-13, IL-17A, cotaxin, IFN-$\gamma$, IP-10, MCP-1 (MCAF), MIP-1$\alpha$, MIP-1$\beta$, RANTES, and TNF-$\alpha$. Exemplary anti-inflammatory cytokines include, but are not limited to, IL-1ra and IL-10. Exemplary regulatory cytokines (shows both anti- and pro-inflammatory effects) include, but are not limited to, IL-2, IL-4, IL-7, IL-9, and IL-15. In some examples, the cytokine is one or more of: interferon-$\gamma$, interleukin (IL)-1-$\beta$, IL-5, IL-6, IL-8, IL-13, IL-17A, or IL-12 protein 70 (IL-12p70).

Decreasing (or Reducing): A negative change relative to a control value, such as a decrease of at least 10%, at least 15%, at least 20%, at least 25%, at least 30%, at least 40%, at least 50%, at least 60%, at least 70%, at least 80%, at least 90%, at least 95%, at least 98%, at least 99%, or at least 100% decrease as compared to a control value. A decrease can be within a range, for example, about 25% to 100%, about 25% to 98%, about 25% to 95%, about 25% to 90%, about 25% to 80%, about 25% to 70%, about 25% to 50%, about 50% to 100%, about 75% to 100%, about 90% to 100%, about 95% to 100%, about 98% to 100%, about 99% to 100%, about 50% to 75%, about 50% to 80%, about 50% to 90%, about 50% to 95%, about 50% to 98%, about 75% to 80%, about 75% to 90%, about 75% to 95%, or about 75% to 98%.

Effective Amount: An amount of a composition that alone, or together with an additional agent(s) (for example additional antioxidants), induces the desired response, such as a change in cytokine production. The preparations disclosed herein can be administered in effective amounts. The effective amount can be administered in a single dose, or in several doses, for example daily. The effective amount can depend on the subject being treated, the subject's condition, and the manner of administration.

In some examples, an effective amount of the immunomodulatory product disclosed herein is an amount that increases function of natural killer cells, decreases T cell activation, alters CD69 expression on immune cells, alters cytokine expression in a subject, and/or decreases inflammation in a subject, relative to a suitable control. In a specific, non-limiting example, the effective amount alters expression of an anti-inflammatory cytokine in a subject relative to a suitable control.

Extract: A substance obtained from a mixture by a physical or chemical process, for example by dissolving the substance in a solvent. An extract includes an organic product derived from a biological material, such as a fruit, vegetable, plant, or animal material. The process of generating an extract may include the use of solvents, such as aqueous solvents (for example physiological saline, water, 1-4% glucose, or 1-4% fructose), organic solvents (for example, ethanol, methanol, acetone, glycerol, acetonitrile, dimethyl sulfoxide, or PLURONIC® surfactants), or combinations thereof. Preparation of an extract may also include treatment of the starting material with heat or pressure. Extracts may also be prepared by mechanical means, such as grinding, sonication, or freeze-thaw treatment.

Fermentate: A product made by fermentation. A fermentate can be produced by aerobic and/or anaerobic fermentation. In some examples, an aerobic fermentate is further fermented anaerobically to produce an immunomodulatory product.

Fermentation is a natural process by which microorganisms (e.g., yeast and bacteria) metabolize organic substrates (e.g., starch and sugar) producing alcohols, acids, and other metabolites. In food processing, fermentation is often carried out in two stages. The first stage is Aerobic Fermentation (fermentation in the presence of oxygen) and the second stage is Anaerobic Fermentation (fermentation in the absence of oxygen). Aerobic fermentation is also known as overflow metabolism, aerobic glycolysis, the Warburg effect, the Crabtree effect, and the lactate switch.

Flare-up or flare: An exacerbation of a condition or disorder, such as an inflammatory disorder and/or autoimmune disorder. A flare-up occurs when symptoms that have been present for a time suddenly worsen. For example, in a flare-up, severity of symptoms transiently worsen but eventually subside or lessen. For example, in an inflammatory disorder and/or autoimmune disorder, inflammation or other signs or symptoms of the inflammatory disorder and/or autoimmune disorder can worsen during a flare-up.

Food Grade: A material that is either safe for human consumption or safe to come into direct contact with food products. Standards for "food grade" are provided by the U.S. Food and Drug Administration.

Free radical: A chemically reactive species which possesses one or more single unpaired electrons. Free radicals include reactive oxygen species and reactive nitrogen species. In cells, free radicals cause oxidative damage, for example to lipids, proteins, or nucleic acids.

Free radicals arise during normal metabolism as a consequence of ATP production by the mitochondria. They are also generated by neutrophils and other cell types as part of inflammatory processes. Environmental factors, such as ionizing radiation, pollution, environmental toxins, and lifestyle stressors, such as cigarette smoking and alcohol consumption also affect levels of free radicals.

A free radical generator is a compound which produces ROS or RNS. Examples of free radical generators include hydrogen peroxide, 2,2'-azobis(2-amidinopropane) dihydrochloride (AAPH), tert-butylhydroperoxide, and cumene hydroperoxide.

Immune-Supportive Fungi: Medicinal fungi that support the immune system. Medicinal mushrooms have been used in Eastern medicine for thousands of years. They are typically used as dietary supplements in the form of extracts or powders, which can be mixed with a food or drink. Non-limiting examples include reishi, lion's mane, chaga, shitake, turkey tail, cordyceps, maitake, and oyster mushrooms. Dietary supplements of medicinal fungi in the form of capsules or powders are commercially available, for example, through Fungi Perfecti, LLC (e.g., Lion's Mane Powder SKU NPHE100G, Turkey Tail powder SKU NPTV100G, Reishi powder SKU NPGL100G, Cordyceps powder SKU NPCS100G, etc.).

Increasing (or Improving): A positive change relative to a control value, such as an increase of at least 10%, at least 20%, at least 25%, at least 30%, at least 40%, at least 50%, at least 60%, at least 75%, at least 90%, at least 100%, at least 200%, at least 300%, at least 400%, or at least 500% as compared to the control value. An increase can be within a range, for example, about 25% to 500%, about 25% to 400%, about 25% to 300%, about 25% to 200%, about 25% to 100%, about 25% to 75%, about 25% to 50%, about 50% to 500%, about 75% to 500%, about 100% to 500%, about 200% to 500%, about 300% to 500%, about 400% to 500%, about 50% to 100%, about 50% to 200%, about 50% to 300%, about 50% to 400%, about 50% to 500%, about 100% to 200%, about 100% to 300%, about 100% to 400%, about 100% to 500%, or about 250% to 500%.

Glucosamine: An amino sugar compound found in cartilage and the fluid that surrounds joints. Oral consumption of glucosamine may increase, and/or prevent the breakdown, of cartilage or the fluid that helps cushion joints. Glucosamine products, such as glucosamine sulfate, glucosamine hydrochloride, or N-acetyl glucosamine, are often taken orally to decrease symptoms of joint conditions, such as osteoarthritis or rheumatoid arthritis.

Immunomodulatory: A substance that stimulates or suppresses the immune system of a subject, for example, the human immune system. In some examples, an immunomodulatory product suppresses the immune system of a human subject.

Inflammation and Inflammatory disorder: Inflammation is a localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods, including, but not limited to measuring the number of white blood cells, the number of polymorphonuclear neutrophils (PMN), a measure of the degree of PMN activation, such as luminol enhanced-chemiluminescence, or a measure of the amount of cytokines present. C-reactive protein is a marker of a systemic inflammatory response.

An inflammatory disorder is a genus of disorders in which inflammation disrupts normal or regular physiological function. Inflammatory disorders can include a variety of conditions, such as autoimmune disorders (an inappropriate inflammatory response to an endogenous antigen), and disorders caused by inflammation due to traumatic injury or exogenous antigens. A primary inflammatory disorder is a disease or disorder that is caused by inflammation itself. A secondary inflammatory disorder is inflammation that is the result of another disorder. Inflammation can lead to inflammatory disorders, such as acute respiratory distress syndrome (ARDS), angitis, appendicitis, arteritis, arthrosteitis, asbestosis, asthma, atherosclerosis, Bechet's disease, beryliosis, blepharitis, bronchiectasis, bronchiolitis, bronchitis, chronic bronchitis, bursitis, cellular interstitial pneumonia, cellulitis, cervicitis, cholangitis, chorioamnionitis, chronic cholecystitis, chronic inflammatory demyelinating polyneuropathy, chronic obstructive pulmonary disease (COPD), chronic kidney disease (CKD), conjunctivitis, cystitis, dacryoadenitis, degenerative arthritis, atopic dermatitis, dermatitis, Seborrheic dermatitis, dermatomyositis, desquamative interstitial pneumonia, encephalitis, endocarditis, enteritis, epicondylitis, epididymitis, fasciitis, fibrositis, gastritis, gastroenteritis, giant cell interstitial pneumonia, gingivitis, glomerulonephritis, gout, hepatitis, hiradentis suppurativa, ileitis, inclusion body myositis, inflammatory arthritis, interstitial cystitis, juvenile idiopathic arthritis, laryngitis, Lyme arthritis, lymphadenitis, lymphoid interstitial pneumonia, myelitis, myocarditis, nephritis, omphalitis, orchitis, osteitis, osteomyelitis, otitis, pancreatitis, parotitis, pelvic inflammatory disease, pericarditis, periodontitis, pharyngitis, phlebitis, pleuritis, pneumoconiosis, pneumonia, pneumonitis, polymyalgia rheumatica (PMR), polymyositis, proctitis, prostatitis, pyelonephritis, reactive arthritis, Reiter's syndrome, relapsing polychondritis, respiratory tract inflammation, rhinitis, rosacea, sarcoidosis, sclerosing cholangitis, sepsis, silicosis, sinusitis, stomatitis, synovitis, systemic sclerosis, talcosis, temporal arteritis, tendonitis, testitis, thrombocytopenia purpura, tonsillitis, transverse myelitis, urethritis, urocystitis, usual interstitial pneumonitis, vaginitis, vasculitis, vulvitis, vulvovaginitis, and the like.

An inflammatory disorder may be chronic, lasting for months or years and going through phases of remission and relapse or flare-ups. An inflammatory disorder may be acute with sudden onset with all signs and symptoms of the disorder resolving over a period of weeks or months.

Oxidative challenge (oxidative stress): Conditions under which molecules such as lipids, proteins, or nucleic acids are vulnerable to oxidative damage. An oxidative challenge can involve the introduction of free radicals, ROS, or RNS, such as to RBC or lysed RBC, for example in an assay of antioxidant activity. The oxidative challenge may be created by adding a free radical generator, such as hydrogen peroxide or AAPH.

Oxidative damage: Damage to cellular components, such as lipids, proteins, or nucleic acids from oxidation or nitrosylation resulting from the presence of free radicals, ROS, or RNS. Oxidative damage may contribute to disease states, such as cardiovascular disease (for example atherosclerosis, ischemia/reperfusion injury, restenosis, and hypertension), cancer, inflammatory disorders (such as acute respiratory distress syndrome, asthma, inflammatory bowel disease, dermal and ocular inflammation, and arthritis), metabolic disease such as diabetes, and diseases of the central nervous system such as amyotrophic lateral sclerosis, Alzheimer disease, Parkinson disease, or stroke.

The lipid components of the cell membrane are prone to oxidative damage. ROS species act on unsaturated lipids to yield reactive unsaturated aldehydes. These unsaturated aldehydes can react with other cellular components, such as membrane-bound or associated proteins and nucleic acids, thereby crosslinking them to the lipid. Oxidized lipids may be identified by presence of lipid peroxides.

Proteins are also susceptible to oxidative damage. In particular, proteins containing sulfhydryl groups and iron-sulfur clusters are vulnerable to attack by ROS. For example, ROS attack on mitochondrial aconitase will cause release of the iron from the protein and inactivation of the enzyme. Oxidative damage to proteins may inhibit normal function, induce protein fragmentation, or lead to crosslinking with lipids, nucleic acids and other proteins, promoting formation of aggregates. Oxidized proteins may be identified by presence of protein carbonyls.

Oxidative damage to nucleic acids results in strand breakage and formation of abasic sites, oxidized bases and DNA adducts. Damaged bases can lead to mutations or altered gene expression. Oxidized nucleic acids may be identified by presence of oxidized bases, such as 8-oxo-guanine.

Macrophage: A type of white blood cell that phagocytoses and degrades cellular debris, foreign substances, microbes, and cancer cells. In addition to their role in phagocytosis, these cells play a role in development, tissue maintenance and repair, and are involved in both innate and adaptive immunity in that they recruit and influence other cells, including immune cells such as lymphocytes. Macrophages can exist in many phenotypes, including phenotypes that have been referred to as M1 and M2. Macrophages that perform primarily pro-inflammatory functions are called M1 macrophages ($CD86^+/CD68^+$), whereas macrophages that decrease inflammation and encourage and regulate tissue repair are called M2 macrophages ($CD206^+/CD68^+$). The markers that identify the various phenotypes of macrophages vary among species. It should be noted that macrophage phenotype is represented by a spectrum that ranges between the extremes of M1 and M2. F4/80 (encoded by the adhesion G protein coupled receptor E1 (ADGRE1) gene) is a macrophage marker, see GENBANK® Accession No. NP_001243181.1, Apr. 6, 2018 and NP_001965, Mar. 5, 2018, both incorporated herein by reference.

Natural Killer (NK) Cell: A type of cytotoxic lymphocyte and a component of the innate immune system. NK cells can be identified by the presence of CD56 and the absence of CD3 (CD56+, CD3−).

"Increasing a function" of natural killer cells includes an increase of CD69 expression and/or an increase in cytokine production by the natural killer cells. NK cells (belonging to the group of innate lymphoid cells) are one of the three kinds of cells differentiated from the common lymphoid progenitor, the other two being B and T lymphocytes.

Nutraceutical: A composition containing components from food sources that confer extra health benefits in addition to the basic nutritional value found in the food, for example, products that contain probiotics, reduce inflammation, or are immunomodulatory. Non-limiting examples of nutraceuticals include health foods and dietary supplements. In some examples, the immunomodulatory product disclosed herein is a nutraceutical composition.

Nutrients: Nutrients are nutritious components in foods that an organism uses to survive and/or thrive. Although nutrients are present in food, a nutrient as used herein can be either naturally occurring or synthetically manufactured. A "whole food nutrient" refers to a nutrient that is found in whole food and not synthetically made.

Pharmaceutically Acceptable Vehicles: The pharmaceutically acceptable vehicles (carriers) useful in this disclosure are conventional. *Remington's Pharmaceutical Sciences*, by E. W. Martin, Mack Publishing Co., Easton, PA, 19th Edition (1995), describes compositions and formulations suitable for pharmaceutical delivery of one or more compositions, such as the immunomodulatory product disclosed herein. The use of pharmaceutically acceptable carriers does not imply that that product so made is useful only for pharmaceutical purposes. Rather it implies that the product is suitable for administration to or consumption by a subject, for example as a pharmaceutical or nutraceutical that is suitable for oral ingestion by a subject.

In general, the nature of the vehicle will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Postbiotic: Bioactive compounds probiotic bacteria produce when they consume prebiotics. There are many types of postbiotics, including short chain fatty acids, lipopolysaccharides, exopolysaccharides, enzymes, cell wall fragments, bacterial lysates, and other metabolites (such as vitamins and amino acids). Postbiotics have been linked to health benefits, such as reducing inflammation and promoting immune responses. Postbiotics may also improve symptoms of inflammatory bowel disease (including Crohn's disease and ulcerative colitis) and reduce the frequency or duration of diarrhea.

Prebiotic: A nutrient that promotes the growth of beneficial microorganisms, particularly microorganisms that colonize the lower digestive tract. Prebiotics are typically plant fibers (indigestible carbohydrates). Prebiotics are commonly found in fruits, vegetables, and whole grains. Non-limiting examples include galactooligosaccharides, fructooligosaccharides, oligofructose, chicory fiber, and inulin.

Probiotic (Microorganism): A microorganism (e.g., bacteria or yeast) that is intended to have health benefits (e.g., aiding in digestion, preventing illness, modulating the immune system, reducing inflammation, or producing vitamins) when consumed. Exemplary probiotic bacteria include: *Bifidobacterium lactis* (SD-5219), *Lactobacillus acidophilus* (SD-5221), *Lactobacillus paracasei* (SD-5218), *Bifidobacterium lactis* (SD-5220), *Bifidobacterium longum, Lactobacillus acidophilus, Lactobacillus brevis, Lactobacillus bulgaricus, Lactobacillus casei, Lactobacillus fermentum, Lactobacillus helveticus, Lactobacillus kefiranofaciens, Lactobacillus kefirgranum, Lactobacillus rhamnosus, Lactococcus lactis, Lactococcus cremoris, Streptococcus thermophilus, Lactobacillus kefir, Lactobacillus parakefir, Lactobacillus plantarum, Lactococcus lactis biovar diacetylactis, Leuconostoc lactis, Leuconostoc mesenteroides, Leuconostoc cremoris*, and *Leuconostoc dextranicum*. Exemplary probiotic yeast include: *Kluyveromyces marxianus, Brettanomyces anomalus, Debaryomyces hansenii, Saccharomyces unisporus, Saccharomyces turicensis, Saccharomyces cerevisiae, Saccharomyces exiguus, Torulaspora delbrueckii*.

Probiotic microorganisms can include one or more microorganism. In some examples, probiotic microorganisms include at least one probiotic bacteria (such as a *Lactobacillus* or *Bifidobacterium*) and at least on probiotic yeast (such as a *Saccharomyces*). In some examples, probiotic microorganisms include at least one organism capable of aerobic fermentation and at least one organism capable of anaerobic fermentation. In some examples, the probiotic microorganisms include the GARDEN OF LIFE™ Raw Probiotics Ultimate Care capsules, which contain 34 probiotic strains (Cat. No: 658010123334).

In some embodiments, the probiotic microorganisms include *Lactobacillus* acidophilus, *Lactobacillus plantarum, Lactobacillus rhamnosus, Lactobacillus fermentum, Lactobacillus casei, Bifidobacterium bifidum, Bifidobacterium*

*longum, Bifidobacterium breve, Bifidobacterium animalis* subsp. *lactis, Streptococcus thermophillus, Lactococcus lactis, Lactobacillus bulgaricus*, and *Saccharomyces cerevisiae*.

Physiological saline (PS): A solution which contains a physiological concentration of saline (about 0.85-0.9%), such as 0.9% NaCl. In some examples, the PS may be buffered. Examples of buffered PS include phosphate-buffered saline (PBS), Hank's balanced salt solution, or lactated Ringer's solution. PS may also contain electrolytes other than sodium, such as potassium, chloride, calcium and phosphate.

Purified: The term purified does not require absolute purity; rather, it is intended as a relative term. Thus, for example, a purified substance is one in which the substance is more enriched than the substance in its natural environment. In one embodiment, a preparation is purified such that the substance represents at least about 5% (such as, but not limited to, at least 10%, 20%, 30%, 40%, 50%, 70%, 80%, 90%, 95%, 98% or 99%) of the total content of the preparation.

Slurry: A mixture of solids denser than water suspended in liquid, usually water or another aqueous carrier. A slurry can be used to transport solids, wherein the liquid is a carrier that is pumped on a device such as a centrifugal pump. The size of solid particles may vary from 1 micron up to hundreds of millimeters. In several embodiments, the aqueous carrier is water.

Stabilizer: A substance that is used to reduce (including inhibit or prevent) degradation of a product. In some examples, the stabilizer is bentonite clay. Other exemplary stabilizers include sodium alginate, sodium carboxymethyl cellulose (CMC), guar gum, locust bean gum, carrageenan, gelatin, or pectin.

Starch: A polymeric carbohydrate consisting of numerous glucose units joined by glycosidic bonds that is present in numerous plants. This polysaccharide is the most common carbohydrate in human diets and is contained in large amounts in staple foods like potatoes, maize (corn), rice, wheat and cassava (manioc). Pure starch is a white, tasteless and odorless powder that is insoluble in cold water or alcohol. It consists of two types of molecules: the linear and helical amylose and the branched amylopectin. Depending on the plant, starch generally contains 20 to 25% amylose and 75 to 80% amylopectin by weight. Non-limiting exemplary sources of starch include bran, flour, rice kernels, buckwheat, rye or oats.

Sugar: Simple sugars, also called monosaccharides, include glucose, fructose, and galactose. Compound sugars, also called disaccharides or double sugars, are molecules composed of two monosaccharides joined by a glycosidic bond. Common examples are sucrose (table sugar) (glucose+fructose), lactose (glucose+galactose), and maltose (two molecules of glucose). In the body, compound sugars are hydrolysed into simple sugars. Non-limiting exemplary sources of sugar include molasses, brown sugar, white sugar, beet sugar, or cane sugar.

Subject: Living multi-cellular vertebrate organisms, including both human and veterinary subjects (e.g., mice, rats, cats, dogs, livestock). In some examples, the subject is a human.

T Cell: A type of cytotoxic lymphocyte and a component of the adaptive immune system. T cells can be distinguished from other lymphocytes by the presence of a T-cell receptor (TCR) on their cell surface. In some examples, T cells can be identified by the absence of CD56 and the presence of CD3 (CD56−, CD3+).

T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8+ T cell is a cytotoxic T lymphocyte. In another embodiment, a CD8+ cell is a suppressor T cell. A T cell is "activated "when it can respond to a specific antigen of interest presented on an antigen presenting cells.

Trace Mineral: A mineral such as iron, manganese, copper, iodine, zinc, cobalt, fluoride, and selenium. In some examples, the source of the trace mineral includes sea salt, rock salt, marine algae (such as kelp or dulse), fulvic acid, humic acid, or mineral pitch (e.g. Himalayan shilajit).

Ultrafiltration: A type of membrane filtration in which forces (such as pressure or concentration gradients) lead to a separation through a semipermeable membrane. Ultrafiltration membranes are typically characterized by the molecular weight cut off (MWCO) of the membrane. Suspended solids and solutes of higher molecular weight are retained in the retentate, while water and lower molecular weight solutes pass through the membrane in the permeate. Different types of modules can be used for ultrafiltration processes. Examples of such modules are tubular elements that use polymeric membranes cast on the inside of plastic or paper tubes; hollow fiber designs that contain multiple hollow fibers; spiral wound modules in which flat membrane sheets are separated by a thin meshed spacer material that is rolled around a central perforated tube and fitted into a tubular steel pressure vessel casing; and plate and frame assemblies that use a membrane placed on a flat plate separated by a mesh like material through which the filtrate passes.

II. Methods of Producing and Product Thereof

A) Overview

Disclosed herein are methods for producing an immunomodulatory product. The methods include combining a source of starch, a source of sugar, and a first source of a trace mineral with probiotic microorganisms and a liquid (e.g., water) to form a slurry. In some embodiments, turmeric is also added to the slurry. The slurry is fermented aerobically, thereby forming an aerobic fermentate. An effective amount of stabilizer and a second source of a trace mineral are added to the aerobic fermentate, thereby forming an intermediate composition. In some embodiments, a stabilizer is not added to the aerobic fermentate. In some embodiments, turmeric is also added to the aerobic fermentate. The intermediate composition is then fermented anaerobically, thereby forming a product. In some embodiments, the product is immunomodulatory.

In some embodiments, the source of starch is bran, flour, rice kernels, buckwheat, rye, or oats; the source of sugar is molasses, brown sugar, white sugar, beet sugar, or cane sugar; the first source of the trace mineral or the second source of the trace mineral are independently selected from sea salt, rock salt, Himalayan sea salt, or marine algae; and/or the stabilizer is bentonite clay. In some embodiments, the stabilizer is bentonite clay, and the effective amount of the stabilizer is the bentonite clay as 5% to 20% by dry weight of the intermediate composition. In additional embodiments, the first source of the trace mineral is kelp, and the second source of the trace mineral is sea salt. In more embodiments, the first and/or second source of the trace mineral comprises fulvic acid or humic acid.

In some embodiments, the slurry includes: the source of starch at about 35% to about 45% by dry weight of the slurry, the source of sugar at about 35% to about 45% by dry weight of the slurry, the first source of the trace mineral at about 4% to about 6% by dry weight of the slurry, the turmeric at about 7.5% to about 9% by dry weight of the slurry, and the probiotic bacteria and yeast at about 0.5% to about 2% by dry weight of the slurry.

In additional embodiments, the intermediate composition includes: the second source of the trace mineral at about 1% to about 2% by dry weight of the intermediate composition, and the stabilizer at about 6% to about 9% by dry weight of the intermediate composition.

In yet other embodiments, the method includes fermenting the slurry aerobically for about 6 to about 8 days to form the aerobic fermentate, and fermenting the intermediate composition for about 6 to about 8 days to form the product.

In further embodiments, the probiotic bacteria include *Lactobacillus* acidophilus, *Lactobacillus plantarum*, *Lactobacillus rhamnosus*, *Lactobacillus fermentum*, *Lactobacillus casei*, *Bifidobacterium bifidum*, *Bifidobacterium longum*, *Bifidobacterium breve*, *Bifidobacterium animalis* subsp. *lactis*, *Streptococcus thermophillus*, *Lactococcus lactis*, *Lactobacillus bulgaricus*, and the probiotic yeast is *Saccharomyces cerevisiae*.

In some embodiments, the probiotic bacteria and yeast are provided as a starter culture. In additional embodiments, the probiotic bacteria are provided at about 110 billion bacterial cells and the probiotic yeast are provided at a concentration of about 1.5 billion yeast cells in the starter culture. In further embodiments, the starter culture is aerobically fermented prior to preparing the slurry.

In some non-limiting examples, a method is provided for producing an immunomodulatory product, including the steps of:
 a) preparing a starter culture including i) rice bran, ii) molasses, and iii) a blend of probiotic bacteria and yeast, wherein the blend includes *Lactobacillus acidophilus*, *Lactobacillus plantarum*, *Lactobacillus rhamnosus*, *Lactobacillus fermentum*, *Lactobacillus casei*, *Bifidobacterium bifidum*, *Bifidobacterium longum*, *Bifidobacterium breve*, *Bifidobacterium animalis* subsp. *lactis*, *Streptococcus thermophillus*, *Lactococcus lactis*, *Lactobacillus bulgaricus*, and *Saccharomyces cerevisiae*;
 b) aerobically fermenting the starter culture for about one day, thereby forming an aerobically fermented starter culture;
 c) preparing a slurry, wherein the slurry includes i) rice bran, ii) molasses, iii) turmeric, iv) kelp powder, and v) the aerobically fermented starter culture;
 d) aerobically fermenting the slurry for about 6 days, thereby forming an aerobic fermentate;
 e) adding to the aerobic fermentate: i) bentonite clay, and ii) sea salt, thereby forming an intermediate composition;
 f) fermenting the intermediate composition anaerobically for about 6 days, thereby forming an anaerobic fermentate;
 g) heating the anaerobic fermentate to about 160 to 170° F. for about 3 to about 5 hours; thereby forming the immunomodulatory product.

In a non-limiting example, the method for producing the immunomodulatory product essentially consists of, or consists of, steps a)-g) above.

In some embodiments, the method includes spray drying the immunomodulatory product into a powder.

In further embodiments, disclosed is a product produced by the methods disclosed herein. Also disclosed is a composition comprising an effective amount of the product. In some embodiments, the composition includes a prebiotic, a probiotic, and a postbiotic. In additional embodiments, the composition includes glucosamine, collagen, immune-supportive fungi, and/or mammalian colostrum. In more embodiments, the composition is animal feed.

Methods are also disclosed for decreasing inflammation in a subject, that include administering to the subject an effective amount of the composition, thereby decreasing inflammation in the subject. In some non-limiting examples, the subject has an inflammatory disorder. In some embodiments, methods are disclosed for increasing function of natural killer cells, decreasing T cell activation, altering cytokine expression, and/or altering CD69 expression on immune cells, in a subject. These methods include administering to the subject an effective amount of a disclosed composition, thereby increasing function of natural killer cells, decreasing T cell activation, altering cytokine expression and/or altering CD69 expression on immune cells in the subject, respectively. In some embodiments, the cytokine is an anti-inflammatory cytokine. In specific non-limiting examples, the cytokine is interferon-γ, interleukin (IL)-1-β, IL-5, IL-6, IL-8, IL-10, IL-13, IL-17A, or IL-12 protein 70 (IL-12p70). In further non-limiting examples, the cytokine is interleukin (IL)-1β or IL-10. In other non-limiting examples, the subject is a veterinary animal or a human.

The stabilizer can be added after aerobic fermentation (e.g., as part of the intermediate composition), or after anaerobic fermentation (e.g., added to the anaerobic fermentate or product). In some embodiments, the stabilizer is a clay, for example, bentonite clay. In some examples, the effective amount is an amount that reduces degradation of the product. In some embodiments, the stabilizer is a preservative. In some embodiments, a stabilizer is not added as part of the intermediate composition, the anaerobic fermentate, or the product.

B) The Slurry

The disclosed methods for producing an immunomodulatory product include combining a source of starch, a source of sugar, a source of a trace mineral, and turmeric, with a probiotic bacteria and yeast to form a slurry.

In the disclosed methods, the source of starch can be cereal grains, for example, wheat, buckwheat, millet, rice, barley, oats, rye, triticale, sorghum, and corn (maize). The source of starch can be whole kernel or milled (e.g., flour or bran). In some embodiments, the source of starch is whole kernels, for example, from rice, sorghum, buckwheat, wheat, rye, or oats. In some embodiments, the source of starch is milled, for example, wheat flour, buckwheat flower, millet flour, rice flour, barley flour, oat flour, rye flour, triticale flour, sorghum flour, corn flour, wheat bran, buckwheat bran, millet bran, rice bran, barley bran, oat bran, or rye bran, triticale bran, sorghum bran, and corn bran. In some examples, the source of starch is bran, flour, rice kernels, buckwheat, rye, or oats. In a specific, non-limiting example, the source of starch is rice bran.

In the disclosed methods, the source of sugar can be any suitable source of soluble carbohydrates. The source of sugar can be raw (e.g., sugar beets, sugar cane, blackstrap molasses) or refined (e.g., white sugar). Exemplary sources of the sugar include molasses (e.g., blackstrap molasses, light molasses, medium molasses, dark molasses, treacle molasses, or sorghum molasses), beet sugar, cane sugar, turbinado sugar, brown sugar, white sugar, and powdered sugar. Other sources of sugar include honey, maple syrup, agave syrup, corn syrup, and fruit sugars (fructose). In some examples, the source of sugar is molasses. In a specific, non-limiting example, the source of sugar is blackstrap molasses.

In the disclosed methods, a trace mineral includes minerals such as iron, manganese, copper, iodine, zinc, cobalt, fluoride, and selenium. Exemplary sources of a trace mineral include, but are not limited to; sea salt, rock salt, marine algae (such as kelp or dulse), fulvic acid, humic acid, and mineral pitch (e.g, Himalayan shilajit). The source of the trace mineral can be a clay. In a specific, non-limiting example, the source of the trace mineral is kelp and/or sea salt. In some embodiments, the source of the trace mineral is added before aerobic fermentation, for example, as part of the slurry. In some embodiments, the source of trace mineral is added after aerobic fermentation, for example, as part of the intermediate composition. In some examples, the slurry includes a first source of a trace mineral, and the intermediate composition includes a second source of a trace mineral. The first and second source are independently selected, and can be the same source or different sources. A source of a trace mineral can be added before aerobic fermentation (e.g., as part of the slurry), after aerobic fermentation (e.g., as part of the intermediate composition), or after anaerobic fermentation (e.g., as part of the product). In some embodiments, the first source of a trace mineral is added before aerobic fermentation (e.g., as part of the slurry), and the second source of a trace mineral is added after aerobic fermentation (e.g., as part of the intermediate composition).

In the disclosed methods, turmeric includes any natural product derived from the *Curcuma longa* plant, including curcumin, a bright yellow compound that is the principal curcuminoid of ground turmeric. Turmeric can come from any part of the *Curcuma longa* plant (e.g., leaves, stems, roots, rhizomes), and includes any suitable form, including whole, ground, extract (e.g., turmeric root extract or curcumin extract), or a further processed form. In some embodiments, the turmeric is ground *Curcuma longa* rhizomes. In some examples, the turmeric is turmeric root alcohol extract (e.g., Oregon's Wild Harvest™ fresh organic turmeric root alcohol extract). In some examples, the turmeric is curcumin extract. The turmeric can be added prior to aerobic fermentation (e.g., added to the slurry), after aerobic fermentation (e.g., added to the aerobic fermentate), or after all fermentation steps (e.g., added to the anaerobic fermentate or product). Turmeric can be added before aerobic fermentation (e.g., as part of the slurry), after aerobic fermentation (e.g., as part of the intermediate composition), after anaerobic fermentation (e.g., as part of the product), or any combination thereof. In some embodiments, turmeric is added before aerobic fermentation.

In some embodiments, the slurry includes a source of starch at about 35% to about 80% by dry weight of the slurry, for example, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 35% to about 75%, about 35% to about 70%, about 35% to about 65%, about 35% to about 60%, about 35% to about 55%, about 35% to about 50%, about 35% to about 45%, about 35% to about 40%, about 40% to about 75%, about 40% to about 70%, about 40% to about 65%, about 40% to about 60%, about 40% to about 55%, about 40% to about 50%, about 50% to about 75%, about 50% to about 70%, about 50% to about 65%, or about 50% to about 60% by dry weight of the slurry. In some examples, the slurry includes the source of starch at about 40-50% by dry weight of the slurry. In a further example, the slurry includes the source of starch at about 35% to 45% by dry weight of the slurry. In a specific, non-limiting example, the slurry includes the source of starch at about 43% by dry weight of the slurry. In a further example, the slurry includes the source of starch at about 42.9% by dry weight of the slurry. In some embodiments, the source of starch is rice bran.

In some embodiments, the slurry includes about 10 to about 50 grams of the source of starch per about 0.5 L slurry volume, for example, about 15 to about 50 about grams, about 20 to about 50 grams, about 25 to about 50 grams, about 30 to about 50 grams, about 35 to about 50 grams, about 40 to about 50 grams, about 45 to about 50 grams, about 10 to about 45 grams, about 10 to about 40 grams, about 10 to about 35 grams, about 10 to about 30 grams, about 10 to about 25 grams, about 10 to about 20 grams, about 10 to about 15 grams, about 20 to about 40 grams, about 20 to about 40 grams, about 20 to about 30 grams, about 20 to about 25 grams, about 25 to about 30 grams, about 25 to about 35 grams, about 25 to about 40 grams, or about 25 to about 50 grams the source of starch. In a specific, non-limiting example, about 20 to about 30 grams of the source of starch is added per about 0.5 L slurry. In some embodiments, the source of starch is rice bran.

In some embodiments, the slurry includes a source of sugar at about 20% to about 60% by dry weight of the slurry, for example, about 25% to about 60%, about 30% to about 60%, about 35% to about 60%, about 40% to about 60%, about 45% to about 60%, about 50% to about 60%, about 55% to about 60%, about 20% to about 55%, about 20% to about 50%, about 20% to about 45%, about 20% to about 40%, about 20% to about 35%, about 20% to about 30%, about 20% to about 35%, about 30% to about 50%, about 30% to about 45%, about 30% to about 40%, about 35% to about 50%, about 35% to about 45%, or about 40% to about 55% by dry weight of the slurry. In some examples, the slurry includes the source of sugar at about 40% to about 50% by dry weight of the slurry. In a further example, the slurry includes the source of sugar at about 35% to 45% by dry weight of the slurry. In a specific, non-limiting example, the slurry includes the source of sugar at about 43% by dry weight of the slurry. In a further example, the slurry includes the source of sugar at about 42.9% by dry weight of the slurry. In some embodiments, the source of sugar is molasses.

In some embodiments, the slurry includes about 10 to about 50 grams of the source of sugar per about 0.5 L slurry volume, for example, about 15 to about 50 grams, about 20 to about 50 grams, about 25 to about 50 grams, about 30 to about 50 grams, about 35 to about 50 grams, about 40 to about 50 grams, about 45 to about 50 grams, about 10 to about 45 grams, about 10 to about 40 grams, about 10 to about 35 grams, about 10 to about 30 grams, about 10 to about 25 grams, about 10 to about 20 grams, about 10 to about 15 grams, about 20 to about 40 grams, about 20 to about 40 grams, about 20 to about 30 grams, about 20 to about 25 grams, about 25 to about 30 grams, about 25 to about 35 grams, about 25 to about 40 grams, or about 25 to about 50 grams the source of sugar per about 0.5 L slurry volume. In a specific, non-limiting example, about 20 to about 30 grams of the source of sugar is added per about 0.5 L slurry. In some embodiments, the source of sugar is molasses.

In some embodiments, the slurry includes turmeric at about 2% to about 40% by dry weight of the slurry, for example, about 5% to about 40%, about 10% to about 40%, about 15% to about 40%, about 20% to about 40%, about 25% to about 40%, about 30% to about 40%, about 35% to about 40%, about 2% to about 35%, about 2% to about 30%, about 2% to about 25%, about 2% to about 20%, about 2% to about 15%, about 2% to about 10%, about 5% to about 35%, about 5% to about 30%, about 5% to about 25%, about 5% to about 20%, about 5% to about 15%, about 5% to about 10%, about 10% to about 40%, about 10% to about 30%, or about 10% to about 20% by dry weight of the slurry. In some examples, the slurry includes turmeric at about 5% to about 10% by dry weight of the slurry. In some examples, the slurry includes turmeric at about 7.5% to about 9% by dry weight of the slurry. In a specific, non-limiting example, the slurry includes turmeric at about 8.5% by dry weight of the slurry.

In some embodiments, the slurry includes about 2 to about 10 grams of turmeric per about 0.5 L slurry volume, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 10 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams turmeric per about 0.5 L slurry volume. In a specific, non-limiting example, about 4-6 grams of turmeric is added per 0.5 L slurry. In some embodiments, the slurry does not include turmeric.

In some embodiments, the slurry includes a first source of a trace mineral at about 0.1% to about 10% by dry weight of the slurry, for example, about 0.2% to about 10%, about 0.3% to about 10%, about 0.4% to about 10%, about 0.5% to about 10%, about 0.6% to about 10%, about 0.7% to about 10%, about 0.8% to about 10%, about 0.9% to about 10%, about 1% to about 10%, about 1.5% to about 10%, about 2% to about 10%, about 2.5% to about 10%, about 3% to about 10%, about 3.5% to about 10%, about 4% to about 10%, about 4.5% to about 10%, about 5% to about 10%, about 6% to about 10%, about 7% to about 10%, about 8% to about 10%, about 9% to about 10%, about 0.1% to about 9%, about 0.1% to about 8%, about 0.1% to about 7%, about 0.1% to about 6%, about 0.1% to about 5%, about 0.1% to about 4.5%, about 0.1% to about 4%, about 0.1% to about 3.5%, about 0.1% to about 3%, about 0.1% to about 2.5%, about 0.1% to about 2%, about 0.1% to about 1.5%, about 0.1% to about 1%, about 0.1% to about 0.5%, about 0.1% to about 0.3%, about 0.5% to about 1.0%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 1% to about 2%, about 1% to about 4%, about 1% to about 5%, about 1% to about 6%, about 1% to about 7%, about 1% to about 8%, about 1% to about 9%, about 2% to about 3%, about 2% to about 4%, about 2% to about 5%, about 2% to about 6%, about 2% to about 7%, about 2% to about 8%, about 2% to about 9%, about 3% to about 6%, about 4% to about 6%, or about 4% to about 8% by dry weight of the slurry. In some examples, the slurry includes the first source of the trace mineral at about 3% to about 5% by dry weight of the slurry. In some examples, the slurry includes the first source of the trace mineral at about 4% to about 6% by dry weight of the slurry. In a specific, non-limiting example, the slurry includes the first source of the trace mineral at about 5% by dry weight of the slurry. In a further example, the slurry includes the first source of the trace mineral at about 4.75% by dry weight of the slurry. In some embodiments, the first source of the trace mineral is kelp powder.

In some embodiments, the slurry includes about 0.5 to about 6 grams of the first source of the trace mineral per about 0.5 L slurry volume, for example, about 1 to about 6 grams, about 1.5 to about 6 grams, about 2 to about 6 grams, about 3 to about 6 grams, about 4 to about 6 grams, about 5 to about 6 grams, about 0.5 to about 5 grams, about 0.5 to about 4 grams, about 0.5 to about 3 grams, about 0.5 to about 2 grams, about 0.5 to about 1 grams, about 2 to about 3 grams, about 2 to about 5 grams, about 2 to about 6 grams, about 3 to about 4 grams, about 3 to about 5 grams, about 3 to about 6 grams the first source of the trace mineral per about 0.5 L slurry volume. In a specific, non-limiting example, about 2 to about 4 grams of the first source of the trace mineral is added per about 0.5 L slurry volume. In some embodiments, the first source of the trace mineral is kelp powder.

The slurry includes a sufficient amount of liquid, such as water, for example, alkaline ionized water. In this context, a sufficient amount of liquid is an amount sufficient to create a suspension for aerobic fermentation. One of ordinary skill in the art can readily determine a sufficient amount of liquid based on the examples provided herein.

The liquid can be any suitable liquid, such as water, for example, alkaline ionized water. The pH of alkaline water, such as alkaline ionized water can be, for example, about 8.5 to about 10, such as about 8.5, about 9.0, about 9.5 or about 10. The pH of alkaline water can be about 8.5 to about 9.5, or about 8.5 to about 9, or about 9 to about 9.5, or about 9.5 to about 10. The pH of alkaline water can be greater than 10, such as, but not limited to about 10 to about 14, such as about 10 to about 13, such as about 10 to about 12, such as about 10 to about 11. The pH of alkaline water can be about 10, about 11, about 12, about 13, or about 14. In some examples, the alkaline water is a pH of about 8 to about 10. The alkaline water can be ionized alkaline water. The alkaline water can be deionized alkaline water. In specific non-limiting examples, the alkaline water can be ionized alkaline water at a pH of about 8 to about 10. The water may be any suitable water, for example, tap water, mineral water, spring water, glacial water, distilled water, sea water, or purified water. In some examples, the water is alkaline water. In some examples, the water is purified water. In other examples, the water is ionized water. In some embodiments, the liquid is a milk or a fruit juice. Any suitable liquid is of use.

The slurry includes probiotic microorganisms, such as probiotic bacteria and/or yeast. Optionally the probiotic microorganisms are provided as a starter culture, and the starter culture is added to the slurry.

In some embodiments, the probiotic microorganisms are collectively capable of aerobic and anaerobic fermentation. In some embodiments the slurry includes at least one probiotic microorganism capable of aerobic fermentation and at least one probiotic microorganism capable of anaerobic fermentation. In some examples, the slurry includes at least 110 billion colony forming units (CFUs) of probiotic bacteria and at least 1.5 billion CFUs of probiotic yeast.

In some embodiments, the probiotic microorganisms are probiotic bacteria and yeast. Exemplary probiotic bacteria include, but are not limited to: *Bifidobacterium lactis* (e.g., SD-5219), *Lactobacillus acidophilus* (e.g., SD-5221), *Lactobacillus paracasei* (e.g., SD-5218), *Bifidobacterium lactis* (e.g., SD-5220), *Bifidobacterium longum, Lactobacillus acidophilus, Lactobacillus brevis, Lactobacillus bulgaricus, Lactobacillus casei, Lactobacillus fermentum, Lactobacillus helveticus, Lactobacillus kefiranofaciens, Lactobacillus kefirgranum, Lactobacillus rhamnosus, Lactococcus lactis, Lactococcus cremoris, Streptococcus thermophilus, Lactobacillus kefir, Lactobacillus parakefir, Lactobacillus plantarum, Lactococcus lactis* biovar diacetylactis, *Leuconostoc lactis, Leuconostoc mesenteroides, Leuconostoc cremoris,* and *Leuconostoc dextranicum.* Additional examples of probiotic *Lactobacillus* species include *L. crispatus, L. delbrueckii* subsp. *bulgaricus, L. gasseri, L. johnsonii, L. reuteri,* and *L. sporogenes.* Additional examples of probiotic *Bifidobacterium* species include: *B. bifidum, B. breve, B. infantis, B. animalis, B. adolescentis, B. essensis,* and *B. laterosporus.* Further examples of probiotic bacteria include: *E. coli* Nissle, *S. cremoris, S. lactis* subsp. *diacetylactis, S. intermedius, S. salivarius, Enterococcus francium, Propionibacterium freudenreichii, Propionibacterium freudenreichii* subsp. *shermanii, Propionibacterium jensenii, Pediococcus, Leuconostoc lactis* subsp. *cremoris, L. lactis* subsp. *lactis Bacillus cereus,* and *Clostridium butyricum.*

In some examples, the probiotic bacteria include a *Lactobacillus,* for example, at least one or more of: *Lactobacillus acidophilus, Lactobacillus paracasei, Lactobacillus acidophilus, Lactobacillus brevis, Lactobacillus bulgaricus, Lactobacillus casei, Lactobacillus fermentum, Lactobacillus helveticus, Lactobacillus kefiranofaciens, Lactobacillus kefirgranum, Lactobacillus rhamnosus, Lactobacillus kefir, Lactobacillus parakefir,* and *Lactobacillus plantarum.*

Exemplary probiotic yeast include, but are not limited to *Kluyveromyces marxianus, Brettanomyces anomalus, Debaryomyces hansenii, Saccharomyces unisporus, Saccharomyces turicensis, Saccharomyces cerevisiae, Saccharomyces exiguus, Torulaspora delbrueckii, Saccharomyces boulardii* and *Kluyveromyces lactis.* In some examples, the probiotic yeast includes *Saccharomyces,* for example, *Saccharomyces cerevisiae.*

In some examples, the probiotic microorganisms is a blend of probiotic bacteria and yeast, wherein the blend includes *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophillus, Lactococcus lactis, Lactobacillus bulgaricus,* and *Saccharomyces cerevisiae.* In some examples, the blend of probiotic bacteria and yeast consists of *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophillus, Lactococcus lactis, Lactobacillus bulgaricus,* and *Saccharomyces cerevisiae.* One or more of these species can be provided separately and blended prior to use. In some embodiments, all of these species are used in the disclosed method.

In some embodiments, the slurry includes a commercially available blend or mixture of probiotic microorganisms, for example, GARDEN OF LIFE™ Raw Probiotics Ultimate Care capsules (Garden of Life, Cat. No: 658010123334), which includes 34 probiotic microorganism strains. Probiotic microorganisms can be added, for example, in the form of a dairy product or fermented product, such as yogurt (e.g., Bulgarian yogurt) or kefir (e.g., Eastern European Wild Kefir culture) cultures. Stains from sauerkraut and wine fermentation, or beer brewing, can also be of use. In some embodiments, the probiotic microorganisms are provided as a starter culture.

In some embodiments, the slurry includes the probiotic microorganisms (e.g., probiotic bacteria and yeast) at about 0.5% to about 5% by dry weight of the slurry, for example, about 0.6% to about 5%, about 0.7% to about 5%, about 0.8% to about 5%, about 0.9% to about 5%, about 1% to about 5%, about 1.5% to about 5%, about 2% to about 5%, about 2.5% to about 5%, about 3% to about 5%, about 3.5% to about 5%, about 4% to about 5% by dry weight, about 1% to about 4%, about 1% to about 3%, about 0.5% to about 3%, or about 0.5% to about 2%, by dry weight of the slurry. In some examples, the slurry includes probiotic microorganisms at about 0.5% to about 2% by dry weight of the slurry. In a specific, non-limiting example, the slurry includes probiotic microorganisms at about 1% by dry weight of the slurry. In a further example, the slurry includes probiotic microorganisms at about 0.9% by dry weight of the slurry. In some examples, a source of probiotic microorganisms is used, such as a commercially available blend or mixture of probiotic microorganisms (which may contain inert filler ingredients), or a dairy or fermented product (such as yogurt, kefir, sauerkraut, wine, or beer product containing probiotic microorganisms).

In some embodiments, the slurry includes about $1\times10^7$ to $1\times10^{12}$ colony forming units (CFUs) of probiotic microorganisms (e.g., probiotic yeast and/or bacteria) per about 0.5 L slurry, for example, about $1\times10^7$ to about $1\times10^{11}$, $1\times10^7$ to about $1\times10^{10}$, about $1\times10^7$ to about $1\times10^9$, about $1\times10^7$ to about $1\times10^8$, about $1\times10^8$ to about $1\times10^{12}$, about $1\times10^9$ to about $1\times10^{12}$, about $1\times10^{10}$ to about $1\times10^{12}$, about $1\times10^{11}$ to about $1\times10^{12}$, about $1\times10^8$ to about $1\times10^{11}$, or about $1\times10^8$ to about $1\times10^{10}$ CFU per 0.5 L slurry. In some examples, the slurry includes about $1\times10^9$ to about $1\times10^{11}$ per 0.5 L slurry. In further examples, the slurry includes at least about $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, or $9\times10^{11}$ CFUs per 0.5 L of slurry.

In some embodiments, the method includes, as a first step, preparing a starter culture that includes a source of starch, a source of sugar, and probiotic microorganisms (e.g., probiotic bacteria and yeast). In some embodiments, the starter culture is aerobically fermented for about 8 hours to 3 days, for about, about 8 hours to about 2 days, about 8 hours to about 1 days, about 12 hours to about 3 days, about 18 hours to about 3 days, about one day to about 3 days, about 2 days to about 3 days, about 12 hours to about 2 days, about 12 hours to about 1 day, about 18 hours to about 2 days, or about 18 hours to about one day. In some examples, the starter culture is aerobically fermented for about 1, about 2, or about 3 days. In some examples, the starter culture is aerobically fermented for about 1 day.

In some embodiments, the starter culture includes the source of starch at about 30% to about 60% by dry weight of the starter culture, for example, in some examples the starter culture includes the source of starch at about 35% to about 60%, about 40% to about 60%, about 45% to about 60%, about 50% to about 60%, about 55% to about 60%, about 30% to about 55%, about 30% to about 50%, about 30% to about 45%, about 30% to about 40%, about 30% to about 35%, about 35% to about 60%, about 35% to about 55%, about 35% to about 50%, about 35% to about 45%, about 35% to about 40%, about 40% to about 50%, or about 45% to about 50% by dry weight of the starter culture. In some examples, the starter culture includes the source of starch at about 40% to about 50% by dry weight of the starter culture. In a specific, non-limiting example, the starter culture includes the source of starch at about 45% by dry weight of the starter culture. In a further example, the starter culture includes the source of starch at about 44.3% by dry weight of the starter culture. In some embodiments, the source of starch is rice bran.

In some embodiments, the starter culture includes the source of sugar at about 30% to about 60% by dry weight of the starter culture, for example, in some examples the starter culture includes the source of sugar at about 35% to about 60%, about 40% to about 60%, about 45% to about 60%, about 50% to about 60%, about 55% to about 60%, about 30% to about 55%, about 30% to about 50%, about 30% to about 45%, about 30% to about 40%, about 30% to about 35%, about 35% to about 60%, about 35% to about 55%, about 35% to about 50%, about 35% to about 45%, about 35% to about 40%, about 40% to about 50%, or about 45% to about 50% by dry weight of the starter culture. In some examples, the starter culture includes the source of sugar at about 40% to about 50% by dry weight of the starter culture. In a specific, non-limiting example, the starter culture includes the source of sugar at about 45% by dry weight of the starter culture. In a further example, the starter culture includes the source of sugar at about 44.3% by dry weight of the starter culture. In some examples, the source of sugar is molasses.

In some embodiments, the starter culture includes probiotic microorganisms (e.g., probiotic bacteria and yeast) at about 5% to about 15% by dry weight of the starter culture, for example, about 5% to about 14%, about 5% to about 13%, about 5% to about 12%, about 5% to about 11%, about 5% to about 10%, about 5% to about 9%, about 5% to about 8%, about 5% to about 7%, about 5% to about 6%, about 6% to about 15%, about 7% to about 15%, about 8% to about 15%, about 9% to about 15%, about 10% to about 15%, about 11% to about 15%, about 12% to about 15%, about 13% to about 15%, about 14% to about 15%, about 8% to about 15%, about 8% to about 12%, about 8% to about 10%, about 10% to about 15%, about 10% to about 14%, or about 10% to about 12% by dry weight of the starter culture. In some examples, the starter culture includes probiotic microorganisms at about 10% to about 13% by dry weight of the starter culture. In another example, the starter culture includes probiotic microorganisms at about 11% to about 12% by dry weight of the starter culture. In a specific, non-limiting example, the starter culture includes probiotic microorganisms at about 11% by dry weight of the starter culture. In a further example, the starter culture includes probiotic microorganisms at about 11.4% by dry weight of the starter culture. In some examples, the starter culture includes at least 110 billion bacterial and about 1.5 billion yeast colony forming units (CFUs) of the probiotic bacteria and yeast, respectively.

In some embodiments, the starter culture includes *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophillus, Lactococcus lactis, Lactobacillus bulgaricus*, and *Saccharomyces cerevisiae*. In some embodiments, the starter culture comprises a blend of probiotic bacteria and yeast consisting of *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophillus, Lactococcus lactis, Lactobacillus bulgaricus*, and *Saccharomyces cerevisiae*.

The starter culture includes a sufficient amount of liquid, such as water, for example, alkaline ionized water. In this context, a sufficient amount of liquid is an amount sufficient to create a suspension for aerobic fermentation. One of ordinary skill in the art can readily determine a sufficient amount of liquid based on the examples provided herein.

Additional ingredients may be added to the slurry, for example, proteases, fruits, or vegetables. In some examples, additional ingredients are added to support growth, maintenance, or other bioactivity of the probiotic microorganisms. Optional ingredients include fibers, peels (such as apple peel), pulps such as fruit and vegetable pulps, spent mash from beer and wine making, and pulp from sugar canes or beets (e.g., for animal feed). In some embodiments, the slurry further includes bentonite clay.

The slurry is fermented aerobically to form the aerobic fermentate. Aerobic fermentation refers to fermentation in the presence of oxygen. In some embodiments, the slurry is fermented aerobically until the pH of the aerobic fermentate becomes acidic. In some embodiments, the slurry is fermented aerobically for about 1 to about 30 days, for example, about 2 to about 30, about 5 to about 30, about 10 to about 30, about 12 to about 30, about 14 to about 30, about 16 to about 30, about 18 to about 30, about 20 to about 30, about 22 to about 30, about 24 to about 30, about 26 to about 30, about 28 to about 30, about 1 to about 28, about 1 to about 26, about 1 to about 24, about 1 to about 22, about 1 to about 20, about 1 to about 18, about 1 to about 16, about 1 to about 14, about 1 to about 12, about 1 to about 10, about 1 to about 8, about 1 to about 7, about 1 to about 6, about 1 to about 4, about 1 to about 2, about 3 to about 8, about 3 to about 10, about 3 to about 14, about 3 to about 20, about 3 to about 25, about 3 to about 30, about 4 to about 8, about 4 to about 10, about 4 to about 14, about 4 to about 20, about 4 to about 25, about 4 to about 30, about 5 to about 10, about 5 to about 12, about 5 to about 14, about 5 to about 16, about 5 to about 18, about 5 to about 20, about 5 to about 25, about 5 to about 30, about 8 to about 10, about 8 to about 12, about 8 to about 14, about 8 to about 16, about 8 to about 18, about 8 to about 20, about 8 to about 25, about 8 to about 30, about 10 to about 15, about 10 to about 20, about 10 to about 25, or about 10 to about 30 days. In some examples, the slurry is fermented aerobically for about 4 to about 7 days. In some examples, the slurry is fermented aerobically for about 5 to about 8 days. In some examples, the slurry is fermented aerobically for about 6 to about 8 days. In a specific, non-limiting example, the slurry is fermented aerobically for about 6 days. In a further example, the slurry is fermented aerobically for about 7 days.

C) The Intermediate Composition

The disclosed methods include fermenting the slurry aerobically at about 10° C. to about 30° C. for about 1 to about 7 days to form an aerobic fermentate. Additional components can be added to the aerobic fermentate, thereby forming an intermediate composition. In some embodiments, the additional components include an effective amount of a stabilizer, a second source of a trace mineral, turmeric, and/or bentonite clay. In some embodiments, a stabilizer is not added to the aerobic fermentate. The intermediate composition is then fermented anaerobically to form the product (immunomodulatory product).

In some embodiments, a stabilizer is added to the aerobic fermentate to form the intermediate composition. The intermediate composition can include the stabilizer at about 5% to about 20% by dry weight of the intermediate composition, for example, about 5% to about 20%, about 8% to about 20%, about 10% to about 20%, about 12% to about 20%, about 15% to about 20%, about 6% to about 20%, about 7% to about 20%, about 8% to about 20%, about 9% to about 20%, about 10% to about 20%, about 12% to about 20%, about 15% to about 20%, about 18% to about 20%, about 3% to about 10%, about 4% to about 10%, about 6% to about 10%, about 7% to about 10%, about 5% to about 10%, about 5% to about 15%, about 7% to about 15%, or about 10% to about 15%, by dry weight of the intermediate composition. In some examples, the intermediate composition includes the stabilizer at about 5% to about 20% by dry weight of the intermediate composition. In some examples, the intermediate composition includes the stabilizer at about 6% to about 9% by dry weight of the intermediate composition. In a specific, non-limiting example, the intermediate composition includes the stabilizer at about 7% by dry weight of the intermediate composition. In a further example, the intermediate composition includes the stabilizer at about 7.1% by dry weight of the intermediate composition. In some embodiments, the stabilizer is bentonite clay. In some embodiments, a stabilizer is not added to the aerobic fermentate.

In some embodiments, the intermediate composition includes about 2 to about 10 grams of stabilizer per about 0.5 L of the intermediate composition, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 15 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams stabilizer per 0.5L of the intermediate composition. In a specific, non-limiting example, about 4 to about 6 grams of stabilizer is added per about 0.5 L of the intermediate composition. In some embodiments, the stabilizer is bentonite clay. In some embodiments, the intermediate composition does not include a stabilizer.

In some embodiments, a second source of a trace mineral is added to the aerobic fermentation to form the intermediate composition. The second source of the trace mineral is independently selected, and can be the same or different, as the first source of the trace mineral added to the slurry. In some examples, the second source of the trace mineral is sea salt. In some examples, the first source of the trace mineral (in the slurry) includes kelp, and the second source of the trace mineral (in the intermediate composition) includes sea salt.

In some embodiments, the intermediate composition includes the second source of the trace mineral at about 0.5% to about 5% by dry weight of the intermediate composition, for example, about 0.6% to about 5%, about 0.7% to about 5%, about 0.8% to about 5%, about 0.9% to about 5%, about 1% to about 5%, about 1.5% to about 5%, about 2% to about 5%, about 2.5% to about 5%, about 3% to about 5%, about 3.5% to about 5%, about 4% to about 5% by dry weight, about 1% to about 4%, about 1% to about 3%, about 0.5% to about 3%, or about 0.5% to about 2%, by dry weight of the intermediate composition. In some examples, the intermediate composition includes the second source of the trace mineral at about 1% to about 2.5% by dry weight of the intermediate composition. In a specific, non-limiting example, the intermediate composition includes the second source of the trace mineral at about 1.5% by dry weight of the intermediate composition. In some embodiments, the second source of the trace mineral is sea salt.

In some embodiments, the intermediate composition includes about 0.5 to about 6 grams of the second source of the trace mineral per about 0.5 L volume of the intermediate composition, for example, about 1 to about 6 grams, about 1.5 to about 6 grams, about 2 to about 6 grams, about 3 to about 6 grams, about 4 to about 6 grams, about 5 to about 6 grams, about 0.5 to about 5 grams, about 0.5 to about 4 grams, about 0.5 to about 3 grams, about 0.5 to about 2 grams, about 0.5 to about 1 grams, about 2 to about 3 grams, about 2 to about 5 grams, about 2 to about 6 grams, about 3 to about 4 grams, about 3 to about 5 grams, or about 3 to about 6 grams the second source of the trace mineral per 0.5 L volume of the intermediate composition. In a specific, non-limiting example, about 1 to about 2 grams of the second source of the trace mineral is added per about 0.5 L of the intermediate composition. In some embodiments, the second source of the trace mineral is sea salt.

In some embodiments, turmeric is added to the aerobic fermentate to form the intermediate composition. In some embodiments, the intermediate composition includes turmeric at about 2% to about 40% by dry weight of the intermediate composition, for example, about 5% to about 40%, about 10% to about 40%, about 15% to about 40%, about 20% to about 40%, about 25% to about 40%, about 30% to about 40%, about 35% to about 40%, about 2% to about 35%, about 2% to about 30%, about 2% to about 25%, about 2% to about 20%, about 2% to about 15%, about 2% to about 10%, about 5% to about 35%, about 5% to about 30%, about 5% to about 25%, about 5% to about 20%, about 5% to about 15%, about 5% to about 10%, about 10% to about 40%, about 10% to about 30%, or about 10% to about 20% by dry weight of the intermediate composition. In some examples, the intermediate composition includes turmeric at about 5% to about 10% by dry weight of the intermediate composition. In a specific, non-limiting example, the intermediate composition includes turmeric at about 8.5% by dry weight of the intermediate composition.

In some embodiments, the intermediate composition includes turmeric at about 2 to about 10 grams per about 0.5 L of the intermediate composition, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 10 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams per about 0.5L of the intermediate composition. In a specific, non-limiting example, about 4 to about 6 grams of turmeric is added per about 0.5L of the intermediate composition.

In some embodiments, the slurry does not include turmeric, but the turmeric is added to the aerobic fermentate to form the intermediate composition. In some embodiments, the slurry includes turmeric and no turmeric is added after aerobic fermentation.

In some embodiments, bentonite clay is added to the aerobic fermentate to form the intermediate composition. The intermediate composition can include bentonite clay at about 5% to about 20% by dry weight of the intermediate composition, for example, about 5% to about 20%, about 8% to about 20%, about 10% to about 20%, about 12% to about 20%, about 15% to about 20%, about 6% to about 20%, about 7% to about 20%, about 8% to about 20%, about 9% to about 20%, about 10% to about 20%, about 12% to about 20%, about 15% to about 20%, about 18% to about 20%, about 3% to about 10%, about 4% to about 10%, about 6% to about 10%, about 7% to about 10%, about 5% to about 10%, about 5% to about 15%, about 7% to about 15%, or about 10% to about 15%, by dry weight of the intermediate composition. In some examples, the intermediate composition includes bentonite clay at about 5% to about 20% by dry weight of the intermediate composition. In some examples, the intermediate composition includes bentonite clay at about 6% to about 9% by dry weight of the intermediate composition. In a specific, non-limiting example, the intermediate composition includes bentonite clay at about 7% by dry weight of the intermediate composition. In a further example, the intermediate composition includes bentonite clay at about 7.1% by dry weight of the intermediate composition. In some embodiments, bentonite clay is an active ingredient.

In some embodiments, the intermediate composition includes about 2 to about 10 grams of bentonite clay per about 0.5 L of the intermediate composition, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 15 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams bentonite clay per 0.5L of the intermediate composition. In a specific, non-limiting example, about 4 to about 6 grams of bentonite clay is added per about 0.5 L of the intermediate composition. In some embodiments, bentonite clay is an active ingredient.

In some embodiments, a sufficient amount of liquid is added to the aerobic fermentate. In some examples, the liquid is water, for example, alkaline ionized water. In this context, a sufficient amount of liquid is an amount sufficient to create a suitable suspension for anaerobic fermentation. One of ordinary skill in the art can readily determine a sufficient amount of liquid based on the examples provided herein.

The intermediate composition is fermented anaerobically to form the anaerobic fermentate. In some embodiments, the anaerobic fermentate is the immunomodulatory product. In some embodiments, the anaerobic fermentate is heated, thereby forming the immunomodulatory product. Anaerobic fermentation refers to fermentation in the absence of oxygen. Anaerobic fermentation can occur for days, weeks, or months. In some embodiments, anaerobic fermentation continues for about 5 to about 120 days, for example, about 10 to about 120 days, about 20 to about 120 days, about 30 to about 120 days, about 40 to about 120 days, about 50 to about 120 days, about 60 to about 120 days, about 70 to about 120 days, about 80 to about 120 days, about 90 to about 120 days, about 100 to about 120 days, about 110 to about 120 days, about 5 to about 110 days, about 5 to about 100 days, about 5 to about 90 days, about 5 to about 80 days, about 5 to about 70 days, about 5 to about 60 days, about 5 to about 50 days, about 5 to about 40 days, about 5 to about 30 days, about 5 to about 20 days, about 5 to about 10 days, about 8 to about 30 days, about 8 to about 60 days, about 8 to about 90 days, about 8 to about 100 days, or about 8 to about 120 days. In some examples, anaerobic fermentation occurs for about 5 days to about 2 months. In some examples, anaerobic fermentation occurs for about 5 to about 8 days. In some examples, anaerobic fermentation occurs for about 6 to about 8 days. In a specific, non-limiting example, the slurry is fermented anaerobically for about 6 days.

In some embodiments, anaerobic fermentation occurs for at least 3 days, for example, for at least 4 days, at least 5 days, at least 6 days, at least 7 days, at least 8 days, at least 10 days, at least 15 days, at least 30 days, at least 45 days, at least 60 days, at least 75 days, at least 90 days, at least 100 days, at least 120 days, or longer. In some examples, anaerobic fermentation occurs for about 5 days to about 2 months, for example, about 1 week to 2 months. In some examples. Anaerobic fermentation occurs for about 5 days to about 8 days. In some examples, anaerobic fermentation continues until the anaerobic fermentate shows reduced activity of the probiotic microorganisms. In some embodiments, cell based testing can be used for quality assurance and to determine the appropriate fermentation time.

The temperature during fermentation (including aerobic and anaerobic) can be, for example, between about 5-60° C., for example, about 5-55° C., about 5-50° C., about 5-45° C., about 5-40° C., about 5-37° C., about 5-35° C., about 5-30° C., about 5-27° C., about 5-25° C., about 7-60° C., about 10-60° C., about 15-60° C., about 25-60° C., about 27-60° C., about 30-60° C., about 35-60° C., about 37-60° C., about 40-60° C., about 18-45° C., about 18-40° C., about 18-37° C., about 18-35° C., about 18-30° C., about 18-27° C., about 18-25° C., about 18-22° C., about 20-45° C., about 20-40° C., about 20-37° C., about 20-35° C., about 20-30° C., about 20-27° C., about 20-25° C., about 25-40° C., about 24-35° C., about 24-37° C., about 30-40° C., about 30-45° C., about 32-35° C., about 40-60° C., about 45-60° C., or about 50-60° C. In a specific, non-limiting example, the temperature during fermentation (aerobic or anaerobic) is about 20-30° C. The temperature during aerobic and anaerobic fermentation can be substantially the same (e.g., both 20-30° C.) or different (e.g., aerobic fermentation at 20-30° C. and anaerobic fermentation at 37-42° C.). The temperature can be room temperature, such as about 24 to about 26° C., for example about 25° C.

A fermentate (including aerobic or anaerobic) may be periodically agitated (e.g., stirred) during fermentation, for example, stirred about every 10 seconds, 30 seconds, 1 minute, 10 minutes, 30 minutes, hourly, every other hour, every three hours, every four hours, every 5 hours, every 12 hours, every day, every other day, or once a week. In some examples, the fermentate is stirred daily. In some examples, the fermentate (including aerobic or anaerobic) is continuously agitated (e.g., mechanically stirred in a vat) throughout fermentation. In some examples, the fermentate (including aerobic or anaerobic) is not agitated. In a specific, non-limiting example, the aerobic fermentate is stirred daily during aerobic fermentation. In another specific example, the anaerobic fermentate is not agitated during fermentation.

In some embodiments, the fermentate (including aerobic or anaerobic) is protected from light during fermentation, for example, by fermenting in an opaque container or by placing a container of fermentate in a dark (or in a substantially dark) location during fermentation.

During aerobic fermentation, the fermentate may be treated to increase oxygen exposure, for example, by adding oxygen to the fermentate, and/or by agitating the fermentate to increase the concentration of dissolved oxygen in the fermentate. During anaerobic fermentation, the fermentate may be substantially deprived of oxygen, for example, by placing the fermentate in a sealed container, not agitating, and/or by adding a $CO_2$ layer over the anaerobic fermentate. During aerobic and/or anaerobic fermentation, the fermentate can be agitated.

Methods of aerobic and anaerobic fermentation can be carried out and optimized following traditional methods for producing fermented foods, such as sauerkraut, Kefir, kimchi, and other traditional fermented foods.

In some embodiments, after anaerobic fermentation the anaerobic fermentate is heated at about 100 to about 200° F. for about 1 to 24 hours, thereby forming the immunomodulatory product. In some examples, the anaerobic fermentate is heated at about 100 to about 200° F., for example, about 100 to about 180° F., about 100 to about 160° F., about 100 to about 140° F., about 100 to about 120° F., about 100 to about 110° F., about 120 to about 200° F., about 140 to about 200° F., about 160 to about 200° F., about 180 to about 200° F., about 120 to about 180° F., about 120 to about 160° F., about 120 to about 140° F., about 140 to about 180° F., about 140 to about 160° F., or about 150 to about 160° F. In some examples, the anaerobic fermentate is heated for about 1 to about 24 hours, for example, about 1 to about 20 hours, about 1 to about 18 hours, about 1 to about 16 hours, about 1 to about 14 hours, about 1 to about 12 hours, about 1 to about 10 hours, about 1 to about 8 hours, about 1 to about 6 hours, about 1 to about 4 hours, about 1 to about 3 hours, about 1 to about 2 hours, about 2 to about 3 hours, about 2 to about 4 hours, about 3 to about 5 hours, about 3 to about 6 hours, about 3 to about 8 hours, about 3 to about 10 hours, about 3 to about 12 hours, about 3 to about 16 hours, about 3 to about 20 hours, about 4 to about 8 hours, about 4 to about 12 hours, about 4 to about 16 hours, about 4 to about 24 hours, about 8 to about 24 hours, or about 12 to 24 hours. In some examples, the anaerobic fermentate is heated at about 150 to 160° F. for about 2 to about 6 hours. In some examples, the anaerobic fermentate is heated at about 150 to 160° F. for about 3 to about 5 hours. In a specific, non-limiting example, the anaerobic fermentate is heated at about 150 to 160° F. for about 4 hours.

D) Additional Description

In some embodiments, the product includes the source of starch at about 35% to about 45% by dry weight of the product, the source of sugar at about 35% to about 45% by dry weight of the product, the first and second source of the trace mineral at about 5% to about 7% by dry weight of the product, the turmeric at about 7.5% to about 9% by dry weight of the product, the stabilizer at about 6% to about 9% by dry weight of the product, and the probiotic bacteria and yeast at about 0.5% to about 2% by dry weight of the product. In some examples, the product includes the source of starch at about 38% to about 40% by dry weight of the product, the source of sugar at about 38% to about 40% by dry weight of the product, the first and second source of the trace mineral together are at about 5% to about 6% by dry weight of the product, the turmeric at about 7.5% to about 8% by dry weight of the product, the stabilizer at about 6.5% to about 8% by dry weight of the product, and the probiotic bacteria and yeast at about 0.5% to about 1.5% by dry weight of the product. In a non-limiting example, the product includes the source of starch at about 39.2% by dry weight of the product, the source of sugar at about 39.2% by dry weight of the product, the first and second source of the trace mineral at about 5.8% by dry weight of the product, the turmeric at about 7.8% by dry weight of the product, the stabilizer at about 7.1% by dry weight of the product, and the probiotic bacteria and yeast at about 0.9% by dry weight of the product.

In several embodiments, the product of the methods disclosed herein is immunomodulatory. In some embodiments, an immunomodulatory product modulates the immune system of a subject, for example, by altering expression of certain markers (e.g., CD69) or altering cytokine production in the subject. The methods can enhance immune surveillance, increase phagocytosis of immune cells, or alter responses to immune challenges, such as allergens or infectious agents. In some examples, the subject is a human. In some examples, the subject is a non-human mammal, for example, a domestic mammal or wild mammal kept in captivity. In some examples, the immunomodulatory product is a food grade product.

In some embodiments, the product is further processed. For example, the liquid and solid fractions of the product may be separated, for example, by centrifugation or membrane filtration. The product can be in the form of a liquid, solid, or processed with other foods. It can be provided as a powder or in a pill format. In some embodiments, the product is spray dried to a powder.

In some examples, the product is further mixed with a suitable carrier (e.g., a pharmaceutically acceptable carrier). Exemplary suitable carriers include starch, cyclodextrin, maltodextrin, methylcellulose, carbonmethoxy cellulose, xanthan gum, and aqueous solutions thereof. Other examples include solvents, dispersion media, coatings, surfactants, antioxidants, preservatives (e.g., arborcide), isotonic agents, absorption delaying agents, stabilizers, gels, binders, excipients, disintegration agents, lubricants, sweetening agents, flavoring agents, dyes, such like materials and combinations thereof. In some examples, the product is further mixed with binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulphate).

In some embodiments, the product (or a fraction thereof) is added to other compositions, for example, to create a nutraceutical product (e.g., health food products or dietary supplements). The nutraceutical can be any suitable form, for example, a liquid, semi-solid, gel, cream, syrup, solid, aerosol, powder, bar, wafer, suspension, or emulsion. The nutraceutical may be a food product (e.g., tea-based beverages, juice, soft drinks, coffee, milk, jelly, cookies, cereals, chocolates, snack bars, herbal extracts, dairy products (e.g., ice cream, and yogurt)), or a food/dietary supplement. Capsules are also o fuse for providing a nutraceutical, such as, but not limited to, gelatin based capsules.

In some embodiments, the product (or a fraction thereof) is added to animal feed, such as a cat or dog food. In some examples, the animal feed is dog food. In some examples, the animal feed is cat food.

Additional compositions can be mixed with the product (or a fraction thereof), for example, one or more of collagen, glucosamine, lutein, cannabidiol, vitamins (such as Vitamin A, B, C, D, E, K, or combinations thereof), fish oil (or other source of omega-3 fatty acids), antioxidants (such as coenzyme Q10), additional probiotics, colostrum, and immune-supportive fungi. In some examples, the product further includes collagen. In some examples, the product further includes glucosamine. In some examples, the product further includes colostrum. In further examples, the product further includes one or more immune-supportive fungi.

In some embodiments, a stabilizer, a source of a trace mineral, turmeric, or bentonite clay is added after anaerobic fermentation (e.g., to the anaerobic fermentate) to form the product.

In some embodiments, the stabilizer is added to the anaerobic fermentate to form the product. In some embodiments, the product includes the stabilizer at about 5% to about 20% by dry weight of the product, for example, about 5% to about 20%, about 8% to about 20%, about 10% to about 20%, about 12% to about 20%, about 15% to about 20%, about 6% to about 20%, about 7% to about 20%, about 8% to about 20%, about 9% to about 20%, about 10% to about 20%, about 12% to about 20%, about 15% to about 20%, about 18% to about 20%, about 3% to about 10%, about 4% to about 10%, about 6% to about 10%, about 7% to about 10%, about 5% to about 10%, about 5% to about 15%, about 7% to about 15%, or about 10% to about 15%, by dry weight of the product. In some examples, the product includes the stabilizer at about 5% to about 20% by dry weight of the product. In some examples, the product includes the stabilizer at about 6% to about 9% by dry weight of the product. In a specific, non-limiting example, the product includes the stabilizer at about 7% by dry weight of the product. In a further example, the product includes the stabilizer at about 7.1% by dry weight of the product.

In some embodiments, the product includes about 2 to about 10 grams of stabilizer per about 0.5 L of the product, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 15 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams stabilizer per 0.5L of the product. In a specific, non-limiting example, about 4 to about 6 grams of stabilizer is added per about 0.5 L of the product.

In some embodiments, a second source of a trace mineral is added to the anaerobic fermentate to form the product. In some embodiments, the product includes a first and a second source of a trace mineral. The second source of the trace mineral can be the same, or different, as the first source of the trace mineral. In some examples, the first source of the trace mineral is kelp (e.g., kelp powder). In another example, the second source of the trace mineral is sea salt. In some examples, the first source of the trace mineral (e.g., kelp) is added to the slurry, and the second source of the trace mineral (e.g., sea salt) is added to the anaerobic fermentate.

In some embodiments, the product includes the second source of the trace mineral at about 0.5% to about 5% by dry weight of the product, for example, about 0.6% to about 5%, about 0.7% to about 5%, about 0.8% to about 5%, about 0.9% to about 5%, about 1% to about 5%, about 1.5% to about 5%, about 2% to about 5%, about 2.5% to about 5%, about 3% to about 5%, about 3.5% to about 5%, about 4% to about 5% by dry weight, about 1% to about 4%, about 1% to about 3%, about 0.5% to about 3%, or about 0.5% to about 2%, by dry weight of the product. In some examples, the product includes the second source of the trace mineral at about 1% to about 2.5% by dry weight of the product. In a specific, non-limiting example, the product includes the second source of the trace mineral at about 1.5% by dry weight of the product.

In some embodiments, turmeric is added to the anaerobic fermentate to form the product. In some embodiments, the product includes turmeric at about 2% to about 40% by dry weight of the product, for example, about 5% to about 40%, about 10% to about 40%, about 15% to about 40%, about 20% to about 40%, about 25% to about 40%, about 30% to about 40%, about 35% to about 40%, about 2% to about 35%, about 2% to about 30%, about 2% to about 25%, about 2% to about 20%, about 2% to about 15%, about 2% to about 10%, about 5% to about 35%, about 5% to about 30%, about 5% to about 25%, about 5% to about 20%, about 5% to about 15%, about 5% to about 10%, about 10% to about 40%, about 10% to about 30%, or about 10% to about 20% by dry weight of the product. In some examples, the product includes turmeric at about 5% to about 10% by dry weight of the product. In a specific, non-limiting example, the product includes turmeric at about 8.5% by dry weight of the product.

In some embodiments, the product includes turmeric at about 2 to about 10 grams per about 0.5 L of the product, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 10 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams per about 0.5L of the product. In a specific, non-limiting example, about 4 to about 6 grams of turmeric is added per about 0.5 L of the product.

In some embodiments, bentonite clay is added to the anaerobic fermentate to form the product. In some embodiments, the product includes bentonite clay at about 5% to about 20% by dry weight of the product, for example, about 5% to about 20%, about 8% to about 20%, about 10% to about 20%, about 12% to about 20%, about 15% to about 20%, about 6% to about 20%, about 7% to about 20%, about 8% to about 20%, about 9% to about 20%, about 10% to about 20%, about 12% to about 20%, about 15% to about 20%, about 18% to about 20%, about 3% to about 10%, about 4% to about 10%, about 6% to about 10%, about 7% to about 10%, about 5% to about 10%, about 5% to about 15%, about 7% to about 15%, or about 10% to about 15%, by dry weight of the product. In some examples, the product includes bentonite clay at about 5% to about 20% by dry weight of the product. In some examples, the product includes bentonite clay at about 6% to about 9% by dry weight of the product. In a specific, non-limiting example, the product includes bentonite clay at about 7% by dry weight of the product. In a further example, the product includes bentonite clay at about 7.1% by dry weight of the product. In some embodiments, bentonite clay is an active ingredient.

In some embodiments, the product includes about 2 to about 10 grams of bentonite clay per about 0.5 L of the product, for example, about 2 to about 8 grams, about 2 to about 7 grams, about 2 to about 6 grams, about 2 to about 5 grams, about 2 to about 4 grams, about 2 to about 3 grams, about 3 to about 10 grams, about 4 to about 10 grams, about 5 to about 10 grams, about 6 to about 15 grams, about 7 to about 10 grams, about 8 to about 10 grams, about 9 to about 10 grams, about 3 to about 9 grams, about 3 to about 7 grams, about 3 to about 6 grams, about 3 to about 5 grams, about 4 to about 9 grams, about 4 to about 8 grams, about 4 to about 7 grams, about 4 to about 6 grams, or about 4 to about 5 grams bentonite clay per 0.5L of the product. In a specific, non-limiting example, about 4 to about 6 grams of bentonite clay is added per about 0.5 L of the product. In some embodiments, bentonite clay is an active ingredient.

As disclosed in U.S. Pat. No. 6,254,920, three main types of pet foods embody the desired characteristics to varying degrees. Canned or high-moisture (greater than 50% moisture) foods are typically all meat and therefore generally highly palatable to animals. Dry or low-moisture content pet foods (less than 15% moisture) are generally highly nutritious, may be inexpensively packaged, and are highly convenient to store and use. Semi-dry or intermediate moisture content pet foods (about 15% to about 50% moisture) are generally more palatable than dry foods, have higher nutritional value, and are more inexpensively packaged and more conveniently used than high moisture foods. The presently disclosed immunomodulatory product can be added to any of these types of pet foods.

The immunomodulatory product can be added to animal feed in general without regard to the protein content which typically varies according to species, breeding status, and age, among other factors. For example, the immunomodulatory product may be used with a dry or semi-dry dog food composition for non-breeding, adult dogs, which requires a minimum protein content of about 18% by weight on a dry matter basis. Similarly, the immunomodulatory product may be applied to a dry or semi-dry puppy food having a minimum protein content of about 22% by weight on a dry matter basis. The immunomodulatory product can be added to both wet and dry cat food. The immunomodulatory product may also be used with other dry and semi-dry foods of varying protein content, and with foods for other animals such as livestock and research animals. To make a dry formulation of the immunomodulatory product, for example, commercially available dry ingredients, including the immunomodulatory product, various nucleotides, amino acids, inorganic salts and organic materials are combined in the desired proportions in a batch mixer and blended to homogeneity.

To make a liquid formulation of the immunomodulatory product, for example, commercially available liquid ingredients are combined in a mixer. Wet ingredients such as animal tissue are ground or emulsified to a slurry and the liquid ingredients are combined with the mixture. A commercially available protease is added to the mixture to hydrolyze the proteins, and later inactivated with heat, acid or another method. Preservatives such as sorbates are also added to the mixture. Water is added to adjust the viscosity and the solids content to between about 10% and 50%. The immunomodulatory product, and other dry ingredients as desired, can be added to the mixture to make the liquid formulation.

In use, the immunomodulatory product can be applied to the particles or pieces of dry or semi-dry pet food such as, for example, dry extruded kibbles. The immunomodulatory product is applied, for example, by spraying or dusting onto the particles or pieces of the food. In a non-limiting example, to make a cat food composition to which the immunomodulatory product is applied, proteinaceous and farinaccous materials and additional desired materials are combined to form an admixture and are well blended. The admixture is then transferred to a steam conditioner and subjected to steam and moisture to adjust the moisture content of the admixture to between about 20% and 40% by weight. The conditioned admixture is then cooked under conditions of elevated temperature and pressure in an extruder such as a single screw extruder. The extruder may include a die having a particular shape, such as a fish, cross or circle. The product is segmented into discrete particles or pieces by a rotating cutting knife as the product is extruded.

The particles or pieces are conveyed to a forced air drying system which raises the temperature of the pieces to about 140° F., and reduces the moisture level to about 8% by weight. The dried particles or pieces are then transferred by bulk conveyor to a coating drum and sprayed with animal fat. Other liquids such as, for example, citric acid or phosphoric acid may alternatively be applied to the pieces, or applied in addition to the animal fat. The pieces are then sprayed or dusted with the immunomodulatory product, and tumbled to thoroughly coat the pieces with the palatability enhancer. The pieces are then cooled to ambient temperature and packaged.

III. Method of Use

Also disclosed herein are methods of decreasing inflammation. These methods can include increasing function of natural killer cells, decreasing T cell activation, altering CD69 expression on immune cells, and/or altering cytokine expression in a subject, by administering to the subject an effective amount of the immunomodulatory product disclosed herein. In some embodiments, the methods include selecting a subject in need of treatment to decrease inflammation or to decrease an autoimmune response.

The subject can be a veterinary subject or a human, for example, a non-human, primate (such as simians), or livestock, including swine, ruminants, horses, and poultry. In some examples, the subject is a domestic pet, such as a cat, dog or rabbit. In some examples, the subject is a mammal. In some examples, the subject is human.

In some embodiments, the subject is healthy, and does not have any underlying disease or condition. In some embodiments, the subject has one or more sign or symptom of inflammation or has an inflammatory disorder (or disease associated with chronic inflammation). Signs or symptoms of inflammation include, but are not limited to: redness, swelling, heat, pain, loss of function of the affected site, fatigue, fever, sores, rashes, abdominal pain, or chest pain. Exemplary inflammatory disorders or diseases associated with chronic inflammation include: asthma, heart disease, diabetes (type I and type II), cancer, chronic peptic ulcer, tuberculosis, arthritis, rheumatoid arthritis, periodontitis, ulcerative colitis, Crohn's disease, sinusitis, fatty liver disease, endometriosis, obesity, Alzheimer's disease, Parkinson's disease, and hepatitis.

In some embodiments, the method decreases inflammation in a subject. In some examples, signs or symptoms of the inflammatory disorder are reduced or eliminated, for example, a complete or partial remission of the inflammatory disorder in a subject. In some examples, the methods reduce or eliminate flare-ups or relapse of the inflammatory disorder in a subject. In some examples, the method reduces or eliminates the frequency or intensity of flare-ups of the inflammatory disorder in a subject. In some embodiments, the method prevents progression of an inflammatory disorder in a subject.

In some embodiments, a subject that has an inflammatory disorder (such as a chronic inflammatory disorder) is selected for treatment. In some embodiments, the inflammatory disorder affects or primarily affects the skin, the respiratory system, the reproductive system, the cardiovascular system, or the nervous system. The subject can have angitis, appendicitis, arteritis, arthrosteitis, asbestosis, asthma, atherosclerosis, Bechet's disease, berylliosis, blepharitis, bronchiectasis, bronchiolitis, bronchitis, chronic bronchitis, bursitis, cellular interstitial pneumonia, cellulitis, cervicitis, cholangitis, chorioamnionitis, chronic cholecystitis, chronic inflammatory demyelinating polyneuropathy, chronic obstructive pulmonary disease (COPD), chronic kidney disease (CKD), conjunctivitis, cystitis, dacryoadenitis, degenerative arthritis, atopic dermatitis, dermatitis, Seborrheic dermatitis, dermatomyositis, desquamative interstitial pneumonia, encephalitis, endocarditis, enteritis, epicondylitis, epididymitis, fasciitis, fibrositis, gastritis, gastroenteritis, giant cell interstitial pneumonia, gingivitis, glomerulonephritis, gout, hepatitis, hiradentis suppurativa, ileitis, inclusion body myositis, inflammatory arthritis, interstitial cystitis, juvenile idiopathic arthritis, laryngitis, Lyme arthritis, lymphadenitis, lymphoid interstitial pneumonia, myelitis, myocarditis, nephritis, omphalitis, orchitis, osteitis, osteomyelitis, otitis, pancreatitis, parotitis, pelvic inflammatory disease, pericarditis, periodontitis, pharyngitis, phlebitis, pleuritis, pneumoconiosis, pneumonia, pneumonitis, polymyalgia rheumatica (PMR), polymyositis, proctitis, prostatitis, pyelonephritis, reactive arthritis, Reiter's syndrome, relapsing polychondritis, respiratory tract inflammation, rhinitis, rosacea, sarcoidosis, sclerosing cholangitis, sepsis, silicosis, sinusitis, stomatitis, synovitis, systemic sclerosis, talcosis, temporal arteritis, tendonitis, testitis, thrombocytopenia purpura, tonsillitis, transverse myelitis, urethritis, urocystitis, usual interstitial pneumonitis, vaginitis, vasculitis, vulvitis, and/or vulvovaginitis. In some examples, the subject has arthritis (e.g., osteoarthritis or rheumatoid arthritis). In some examples, the subject has systemic lupus erythematosus.

In a specific, non-limiting example, the subject has encephalitis. A variety of encephalitis types are included, such as viral encephalitis (such as herpes viral, rabies virus, poliovirus, measles virus, arboviral flavivirus (such as St. Louis and west Nile virus encephalitis), bunyavirus (such as the La Crosse strain), arenavirus (such as lymphocytic choriomeningitis virus), reovirus (such as Colorado tick virus), henipavirus, and Powassan virus), bacterial (such as mycoplasma, rickettsial disease-causing bacteria, bacterial meningitis, or syphilis), parasitic or protozoal infestations (such as toxoplasmosis, malaria, primary amoebic meningoencephalitis, Lyme disease, or *Bartonella henselae*), acute disseminated encephalitis, limbic encephalitis, autoimmune encephalitis, and encephalitis lethargica.

In some examples, the subject has atopic dermatitis (AD). A subject with AD can be selected for treatment. AD due to a variety of causes can be included, such as AD due to genetic factors (such as subjects with a family history of atopy), lack of childhood exposure to allergens, allergens, *Staphylococcus aureus*, and hard water. The methods can include selecting a subject with AD, for example, based on a clinical diagnosis from symptoms such as itchy, red, swollen, and cracked skin with clear fluid may come from the affected areas that can thicken over time.

In some embodiments, the immunomodulatory product is administered systemically to treat the subject. In some examples, the immunomodulatory product is administered by oral administration. In other examples, the immunomodulatory product is administered locally to the skin. In some examples, the method decreases the frequency or severity of flare-ups, or cause remission.

In some embodiments, the method decreases inflammation in the subject, for example, by decreasing one or more sign or symptom of inflammation (e.g., redness, swelling, heat, pain, loss of function of the affected site, fatigue, fever, sores, rashes, abdominal pain, or chest pain). A subject can be selected for treatment that has one or more of symptoms of inflammation. According to one embodiment, for a subject with AD, a subject experiences a decrease in SCORAD (Scoring Atopic Dermatitis score (Dermatology 1993; 186: 23-31) score for one month, two months, three months, or more following a course of treatment. In one embodiment, a subject experiences a decrease in SCORAD score from severe (>50) to moderate (25-50) or mild (<25) for one month, two months, three months or more following a course of treatment. In one embodiment, a subject experiences a decrease in SCORAD score from moderate (25-50) to mild (<25) for one month, two months, three months or more following a course of treatment.

In some embodiments, the method increases function of natural killer (NK) cells in the subject, for example, decreases expression of CD69 or increases cytokine production in NK cells. In some examples, the method increases production and/or secretion of granzyme and perforin, and increases killing of target cells of NK cells. Increased killing can be measured in vitro, such as assessing the ability of isolated NK cells to by cytotoxic for the K562 tumor cell line.

In some embodiments, the method decreases T cell activation in the subject. A decrease in T cell activation can be measured, for example, by a decrease of expression of T cell activation markers (e.g., CD69) or by altering cytokine expression (e.g., (IL)-1-β, IL-1ra, IL-2, IL-4, IL-5, IL-6, IL-7, IL-8, IL-9, IL-10, IL-12 protein 70 (IL-12p70), IL-13, IL-15, IL-17, IL-17A, cotaxin, basic FGF, G-CSF, GM-CSF, IFN-γ, IP-10, MCP-1 (MCAF), MIP-1α, MIP-1β, PDGF-BB, RANTES, TNF-α, and VEGF). In some embodiments, the immunomodulatory product reduces responsiveness of Th17 cells, which produce IL-17A. In some embodiments, the method reduces IL-17 expression by T cells.

In some embodiments, the method alters expression of activation markers on immune cells in the subject. In some examples, the immune cell is a peripheral blood mononuclear cell (PBMC). Non-limiting, exemplary immune cells include T cells, NK cells, NKT cells, non-NK/non-T cell lymphocytes, polymorphonuclear (PMN) cells, monocytes, and macrophages. Exemplary activation markers include, CD69, HLA-DR, CD44, CD137, CD62L, CD27, CCR7, CD154, CD16, NKG2D, NKp46, CD25. In some examples, the method alters expression of CD69 on immune cells. In other embodiments, the method alters monocyte/macrophage activation. Altering expression includes increasing or decreasing expression of activation markers on immune cells. In some embodiments, the method reduces CD69 expression on immune cells, for example, reduces CD69 expression on NK cells, NKT cells, T cells, non-NK/non-T cell lymphocytes, and/or monocytes. In a specific, non-limiting example, the method reduces CD69 expression on NK cells, T cells, and/or monocytes.

In some embodiments, the method alters cytokine expression in the subject. For example, in some examples the effective amount of the immunomodulatory product disclosed herein increases or decreases expression of cytokines, for example, increases or decreases one or more of interleukin (IL)-1-β, IL-1ra, IL-2, IL-4, IL-5, IL-6, IL-7, IL-8, IL-9, IL-10, IL-12 protein 70 (IL-12p70), IL-13, IL-15, IL-17, IL-17A, cotaxin, basic FGF, G-CSF, GM-CSF, IFN-γ, IP-10, MCP-1 (MCAF), MIP-la, MIP-1β, PDGF-BB, RANTES, TNF-α, and VEGF. In some embodiments, the effective amount of the immunomodulatory produce alters IL-1b, IL-6, and/or IL-10 in the subject. In other embodiment, the immunomodulatory product alters G-CSF. In some embodiment, the cytokines are increased. In other embodiments, the cytokines are decreased. In some examples, the method increases (IL)-1β or IL-10 expression in the subject. Altering cytokine expression in the subject includes altering cytokine production by immune cells in the subject, for example, in some examples the method alters cytokine production by immune cells (e.g., PBMCs, NK cells, NKT cells, T cells, non-NK/non-T cell lymphocytes, and monocytes) in the subject. In some embodiments, the method increases expression of one or more cytokines. In other embodiment, the method increased GM-CSF expression in the subject.

In some examples, the cytokine is a proinflammatory cytokine, for example, IL-1-β, IL-5, IL-6, IL-8, IL-12 protein 70 (IL-12p70), IL-13, IL-17A, cotaxin, IFN-γ, IP-10, MCP-1 (MCAF), MIP-1α, MIP-1β, RANTES, and TNF-α. In some examples, the cytokine is an anti-inflammatory cytokine, such as IL-1ra and IL-10. In some examples, the cytokine is a regulatory cytokine (shows both anti- and pro-inflammatory effects), such as IL-2, IL-4, IL-7, IL-9, and IL-15.

Administration of the immunomodulatory product disclosed herein can be by any suitable route. Exemplary routes of administration include, but are not limited to, topical, oral, injection (such as subcutaneous, intramuscular, intradermal, intraperitoneal, and intravenous), sublingual, transdermal, intranasal, topical, and inhalation routes. In some embodiments, administration is oral. Administration can be a single dose, or several doses, for example daily or multiple times daily. In some examples, the immunomodulary product is administered for at least one day, at least one week, at least two weeks, at least four weeks, at least eight weeks, at least twelve weeks, at least twenty-four weeks, at least a year, or longer. In some embodiments, the immunomodulatory product is administered at least once a day for at least about one week. The immunomodulatory product can be administered 1, 2, 3, 4, 5, or 6 times a day.

In additional embodiments, the immunomodulatory product is administered at least twice a day for at least one week. In further embodiments, the immunomodulatory product is administered once a day for at least twelve weeks, at least twice a day for at least twelve weeks, at least three times a day for at least twelve weeks, or at least four times a day for at least twelve weeks. In some embodiments, the immunomodulatory product is administered as needed. The effective amount can depend on the subject being treated, the severity and type of the condition being treated, and the manner of administration.

The effective amount of the immunomodulatory product is an amount that alters immune status of the subject, for example, an amount that reduces inflammatory immune responses of the subject. In some embodiments, the effective amount reduces one or more signs or symptoms of inflammation, including but not limited to, redness, swelling, heat, pain, loss of function of the affected site, fatigue, fever, sores, rashes, abdominal pain, or chest pain. In several embodiments, the effective amount is an amount that alters (increases or decreases) expression of activation markers on immune cells. In some embodiments, the effective amount reduces CD69 expression, for example, on an immune cell of the subject, such as a NK cell, NKT cell, T cell, non-NK/non-T cell lymphocyte, or monocyte. In several embodiments, the effective amount is an amount that alters (increases or decreases) expression of cytokines in the subject, for example, one or more of: IL-1-β, IL-1ra, IL-2, IL-4, IL-5, IL-6, IL-7, IL-8, IL-9, IL-10, IL-12 protein 70 (IL-12p70), IL-13, IL-15, IL-17, IL-17A, cotaxin, basic FGF, G-CSF, GM-CSF, IFN-γ, IP-10, MCP-1 (MCAF), MIP-la, MIP-1β, PDGF-BB, RANTES, TNF-α, and VEGF. In some embodiments, the effective amount increases cytokine expression, for example, IL-1β or IL-10 expression in the subject.

The disclosure is illustrated by the following non-limiting Examples.

EXAMPLES

Example 1

Production of the Test Products

This example describes the development of a consumable nutritional composition that is based on microbial fermentation of a substrate by a mixture of probiotic bacteria and yeast. Four test products (AIW-Tur, AIW-2, PBW-Tur, PBW-2) were produced to evaluate the effects of using alkaline ionized water vs. purified bottled water, or adding turmeric before aerobic fermentation vs. after aerobic fermentation.

Two starter cultures were prepared using a small portion of rice bran, molasses (blackstrap), and probiotic organisms, as indicated below in Table 1.

TABLE 1

Starter Culture

| Name | Rice Bran | Molasses | Probiotic Blend | Water* |
|---|---|---|---|---|
| Starter 1 | 2.5 g | 2.5 g | 630 mg | Alkaline Ionized (AIW) |
| Starter 2 | 2.5 g | 2.5 g | 630 mg | Purified Bottled (PBW) |

*Rice bran, molasses, and probiotic blend were added first, then topped up to 50 mL with water The starter cultures were mixed gently by inversion until the rice bran was wetted, the molasses was dissolved, and the probiotic powder was dispersed. The starter cultures were then covered with a loosened lid and placed in a dark place until they began to show activity (1 day).

The starter cultures were moved to larger containers and additional ingredients were added, as shown below in Table 2:

TABLE 2

Slurry Ingredients

| Name | Starter | Rice Bran | Molasses | Kelp | Turmeric | Water |
|---|---|---|---|---|---|---|
| AIW-Tur | Starter 1 | 25 g | 25 g | 3 g | 5 g[1] | 400 mL AIW |
| AIW-2 | Starter 1 | 25 g | 25 g | 3 g | 5 g[2] | 400 mL AIW |
| PBW-Tur | Starter 2 | 25 g | 25 g | 3 g | 5 g[1] | 400 mL PBW |
| PBW-2 | Starter 2 | 25 g | 25 g | 3 g | 5 g[2] | 400 mL PBW |

[1]Turmeric was added to AIW-Tur and PBW-Tur before fermentation.
[2]Turmeric was added to AIW-2 and PBW-2 after aerobic fermentation was complete.

TABLE 3

| Percent by Dry Weight Slurry Ingredients | | |
|---|---|---|
| Ingredient | Mass | % Total |
| Probiotic | 0.63 g | 1% |
| Rice Bran | 27.5 g | 43.2% |
| Molasses | 27.5 g | 43.2% |
| Kelp | 3 g | 4.7% |
| Turmeric | 5 g | 7.8% |
| Total | 63.63 g | 100% |

Fermentation was carried out in two stages. The first stage was an aerobic fermentation. During aerobic fermentation, the fermentate was placed in a dark cupboard with a loosened lid and stirred daily by inversion for 5 days (until the pH of the fermentate became acidic).

After aerobic fermentation, 5 g bentonite and 1 g sea salt were added to each fermentate, as shown in Table 4 below. These components were added after aerobic fermentation, but before anaerobic fermentation.

TABLE 4

| Percent by Weight Aerobic Fermentate | | |
|---|---|---|
| Ingredient | Mass | % Total |
| Slurry Ingredients | 63.63 g | 91.3% |
| Bentonite Clay | 5 g | 7.2% |
| Sea Salt | 1 g | 1.4% |
| Total | 69.63 g | 100% |

The fermentate container was then closed to facilitate anaerobic fermentation. During anaerobic fermentation, the fermentate was not stirred or agitated. Anaerobic fermentation continued for 8 days.

Aqueous and solid fractions of each product (AIW-Tur, AIW-2, PBW-Tur, PBW-2) can be heated at 150-160° F. for 2-3 hours aliquoted, and banked (frozen). Natural preservatives, such as arborcide, can be added.

Preliminary results indicate that the aqueous fraction contains water-soluble compounds, including metabolites produced during the fermentation and antioxidants. The solid fractions included bacteria, yeast, and the remains of unfermented starting ingredients, such as rice bran, which contains insoluble beta-glucans.

A product containing the same ingredients as the test products, but unfermented (unfermented ingredients; UFI), was also produced for comparison.

Example 2

Antioxidant Capacity

The four products described in Example 1 were tested for antioxidant capacity using the Folin-Ciocalteu assay (also known as the total phenolics assay). The assay was performed by adding Folin-Ciocalteu's phenol reagent to serial dilutions of each test product, thoroughly mixing, and incubating for 5 minutes. Sodium carbonate was then added. The reaction continued for up to 30 minutes at 37° C. Optical absorbance was measured at 765 nm in a colorimetric plate reader. Gallic acid was used as a reference standard, and the data was reported in Gallic Acid Equivalents per milliliter test product.

As shown in FIGS. 1A and 1B, all four products showed increased total antioxidant capacity than the unfermented ingredients (UFI). The two products produced using alkaline ionized water (AIW-Tur and AIW-2) showed better antioxidant capacity than the two test products produced using purified bottled water (PBW-Tur and PBW-2). For both types of water, there was a marginally better total antioxidant capacity in the products where turmeric was added prior to the fermentation process. Turmeric can be added as part of the substrate for fermentation. The fermentation enhanced the benefits of turmeric. However, turmeric can also be added after the fermentation process. The fermentation process enhanced the antioxidant capacity above and beyond that of the antioxidant capacity of the unfermented ingredients.

Example 3

Reduced ROS Production in Human Polymorphonuclear Cells

Natural products with antioxidant capacity can reduce ROS (reactive oxygen species) formation in inflammatory cells.

Freshly purified human polymorphonuclear (PMN) cells were exposed to each of the four test products of Example 1. The cells were then washed and loaded with DCF-DA dye, which turns fluorescent upon exposure to ROS. Formation of ROS was triggered by addition of $H_2O_2$. Fluorescence intensity of the PMN cells was evaluated by flow cytometry. Untreated control cells served as a baseline (negative control) and PMN cells treated with $H_2O_2$ alone served as a positive control.

Figure 2B:
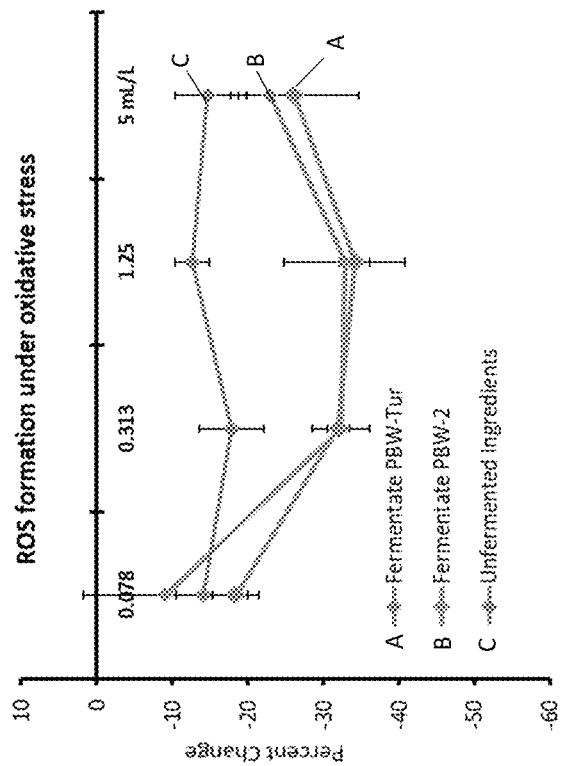
FIGS. 2A and 2B show formation of Reactive Oxygen Species (ROS) by cells under oxidative stress in the presence of each test product or the unfermented ingredients (UFI). The average+standard deviation of replicate data points is shown. The fermentates had more anti-inflammatory properties than the unfermented ingredients, since the production of Reactive Oxygen Species was reduced below that of UFI.
Figure 2A:
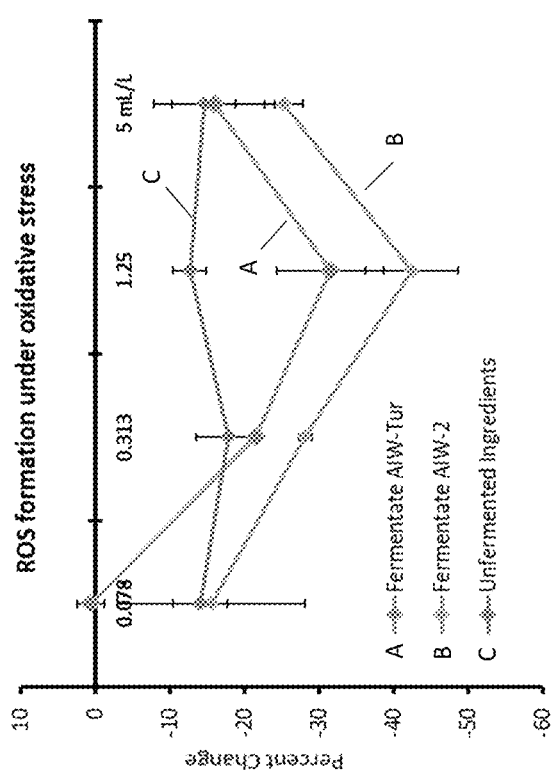

All four test products showed stronger inhibition of ROS than the unfermented ingredients (UFI) (FIGS. 2A and 2B). This was statistically significant for one or more tested doses for all four of the test products. There was not a robust difference between test products produced using alkaline ionized water versus purified bottled water, however, for the two test products using alkaline ionized water, there was a slightly higher reduction in ROS formation when turmeric was added after the completion of the fermentation process (FIG. 2A).

The testing of oxidative stress using human inflammatory cells showed differences between the inhibition of ROS formation by the test products as compared to the UFI sample. This result is one indication of the anti-inflammatory potential of the test products. Without being bound to any particular theory, reduced ROS formation may be achieved through the test product neutralizing ROS by a direct antioxidant effect, or by triggering an anti-inflammatory response that results in reduced ROS.

Example 5

Cell Viability Assay

Peripheral blood mononuclear (PBMC) cells were tested using the MTT assay to help determine an appropriate dose range.

Figure 3A:
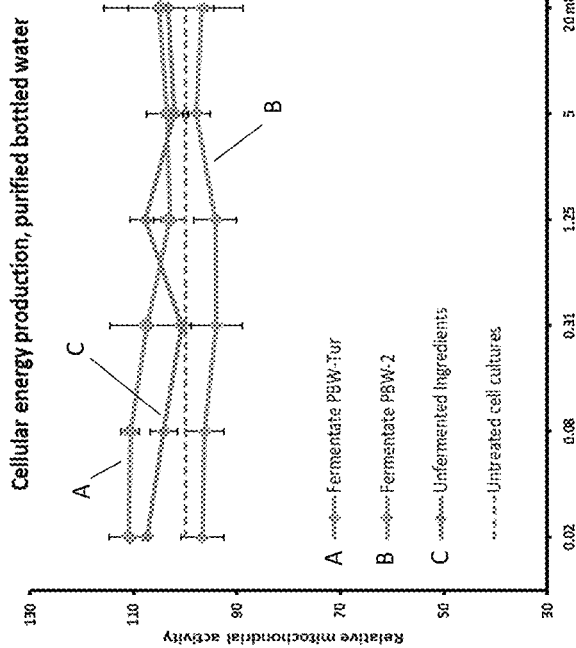
FIGS. 3A and 3B shows cellular energy production as a measure of relative mitochondrial activity. The average±standard deviation is shown. The fermentate produced using purified water supported the mitochondrial function as the difference, when comparing to untreated cells, reached a high level of statistical significance.
Figure 3B:
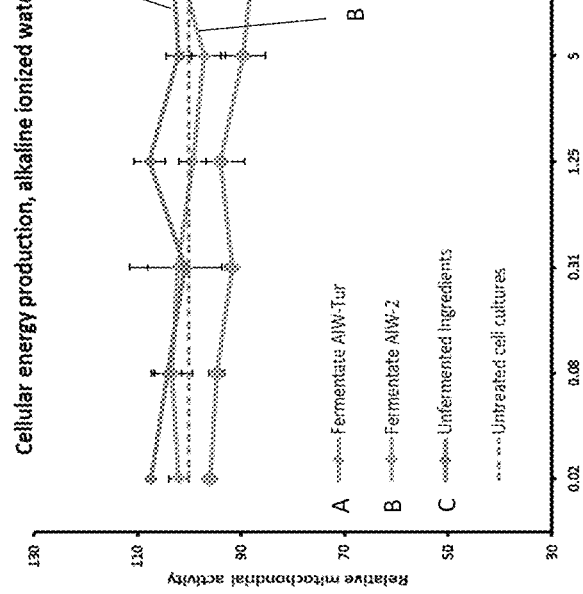
Figure 4A:
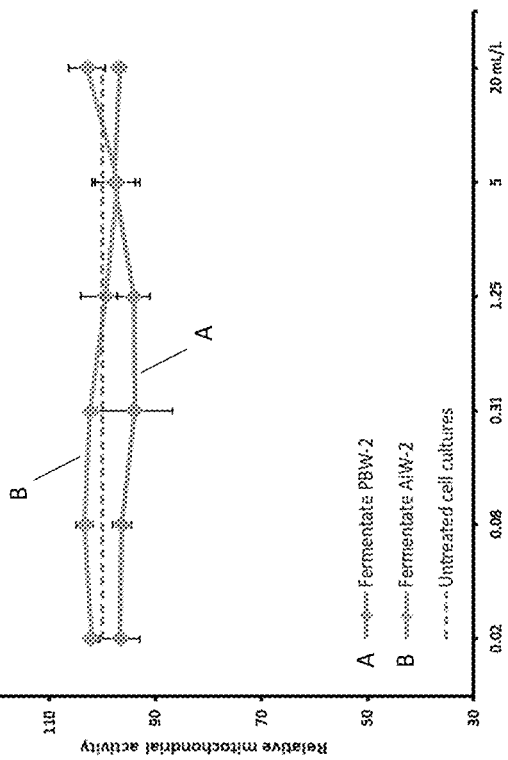
FIGS. 4A and 4B show cellular energy production.
Figure 4B:
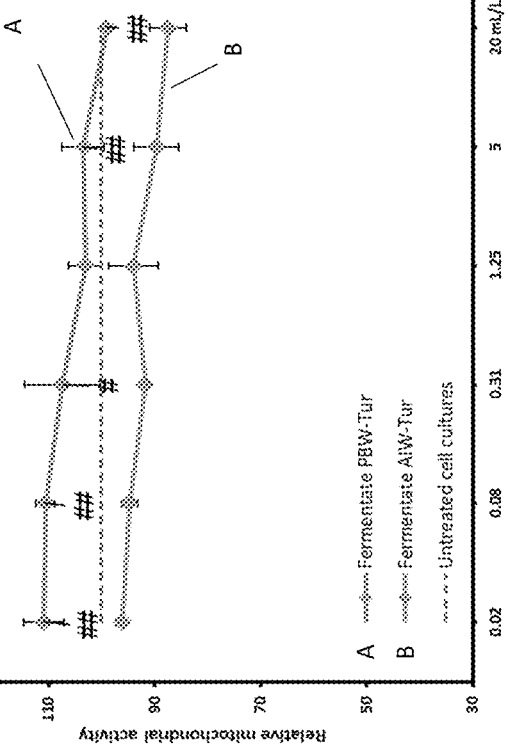

Test product AIW-Tur showed reduced mitochondrial activity at all doses tested (FIG. 3A). Test product PBW-Tur showed increased mitochondrial activity at lower doses as compared to both the untreated control or to treatment with the unfermented ingredients sample (UFI) (FIG. 3B). Test product AIW-2 did not show a change in mitochondrial function as compared to untreated cultures (FIG. 3A). PBW-2 showed decreased mitochondrial activity, both when compared to untreated cultures and when compared to treatment with UFI (FIG. 3B). Treatment with UFI did not affect mitochondrial function, except at the 1.25 mL/L dose where an increase in mitochondrial function was recorded (FIGS. 3A and 3B). There was no detriment to cellular viability in this assay.

Example 6

Expression of Activation Markers

Human peripheral blood mononuclear cells (PBMC) were obtained from a healthy donor. Cultures were incubated for 24 hours with the four test products of Example 1 as well the unfermented ingredients (UFI) and LPS from E. coli (a positive control for activation). The cultures were incubated for 24 hours, after which the cells and the culture supernatants were harvested.

Cells were stained with a combination of monoclonal antibodies to monitor activation, and analyzed by multi-parameter flow cytometry using an acoustic dual laser Attune flow cytometer. The analysis included fluorescent markers for CD3, CD56, and CD69. This combination allowed monitoring of changes to monocyte/macrophages, as well as activation of natural killer cells, NKT cells, and T lymphocytes. Staining with CD3 and CD56 identified CD3-CD56+NK cells, CD3+CD56-T lymphocytes, and CD3+CD56+NK-T cells. When combined with forward/side scatter analysis for cellular size and granularity, monocytes were also identified. Each population was examined for expression level of the activation marker CD69. CD69 is an inducible cell surface glycoprotein involved with lymphoid activation, and has recently been implicated in the immunomodulatory effects leading to control of inflammation.

During data analysis, the physical properties of different cell types allowed electronic gating on lymphocytes versus monocytes, so that the CD69 expression could be analyzed on these cell types separately. In addition, the lymphocyte fraction was divided into 4 separate subpopulations, based on whether cells stain with CD3, CD56, or both.

Natural Killer Cells

Figure 6:
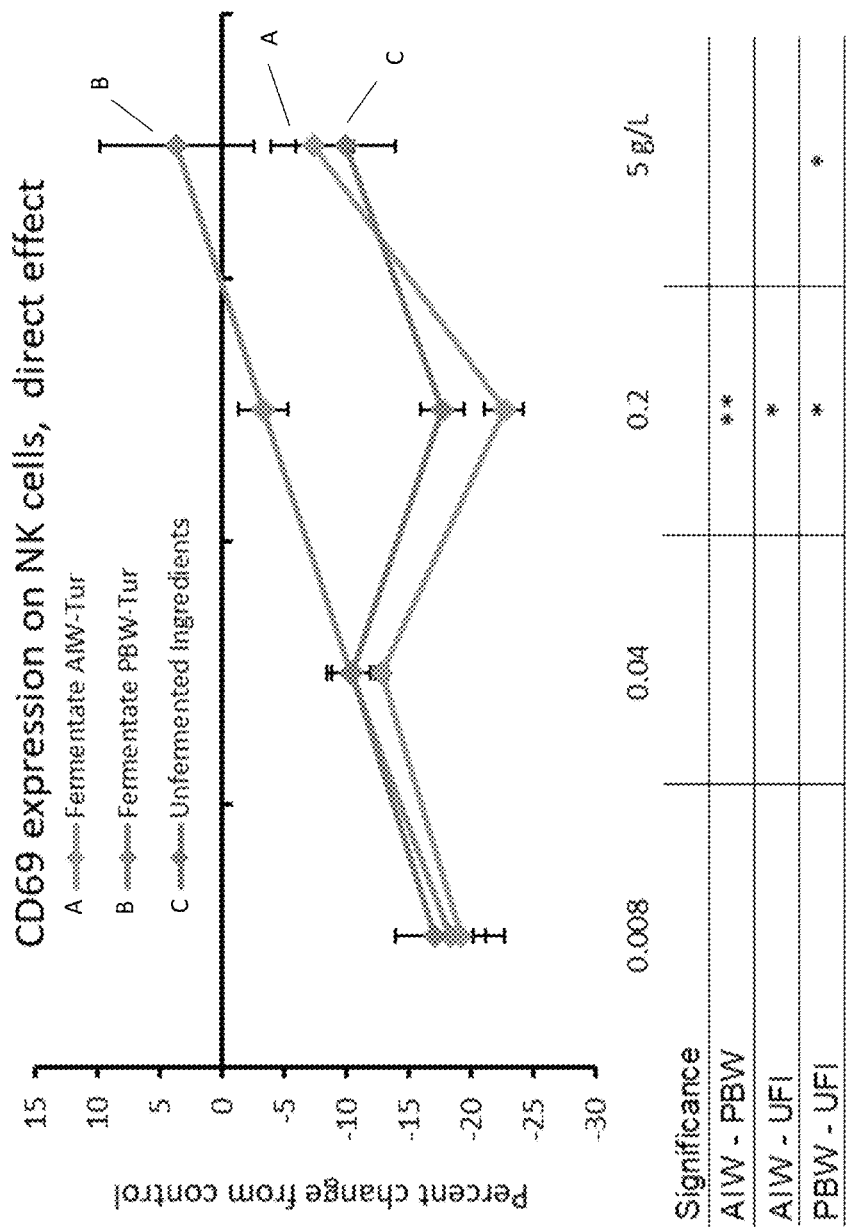
FIG. 6 shows a line graph of the data of FIG. 5 as percent change from the untreated control.

Following activation, Natural Killer (NK) cells express CD69 and therefore an increase in this glycoprotein on the cell surface of NK cells reflects a state of activation. AIW-Tur, PBW-Tur, and UFI all triggered a reduction of CD69 expression on NK cells (FIGS. 5 and 6). At lower doses, all three test products reduced CD69 in a similar manner. At higher doses, the PBW-Tur had no significant effect on CD69 expression on NK cells. In contrast, AIW-Tur and UFI continued to reduce CD69 at higher doses. At a dose of 0.2, AIW-Tur was significantly lower expression as compared to UFI.

T Lymphocytes

Figure 7:
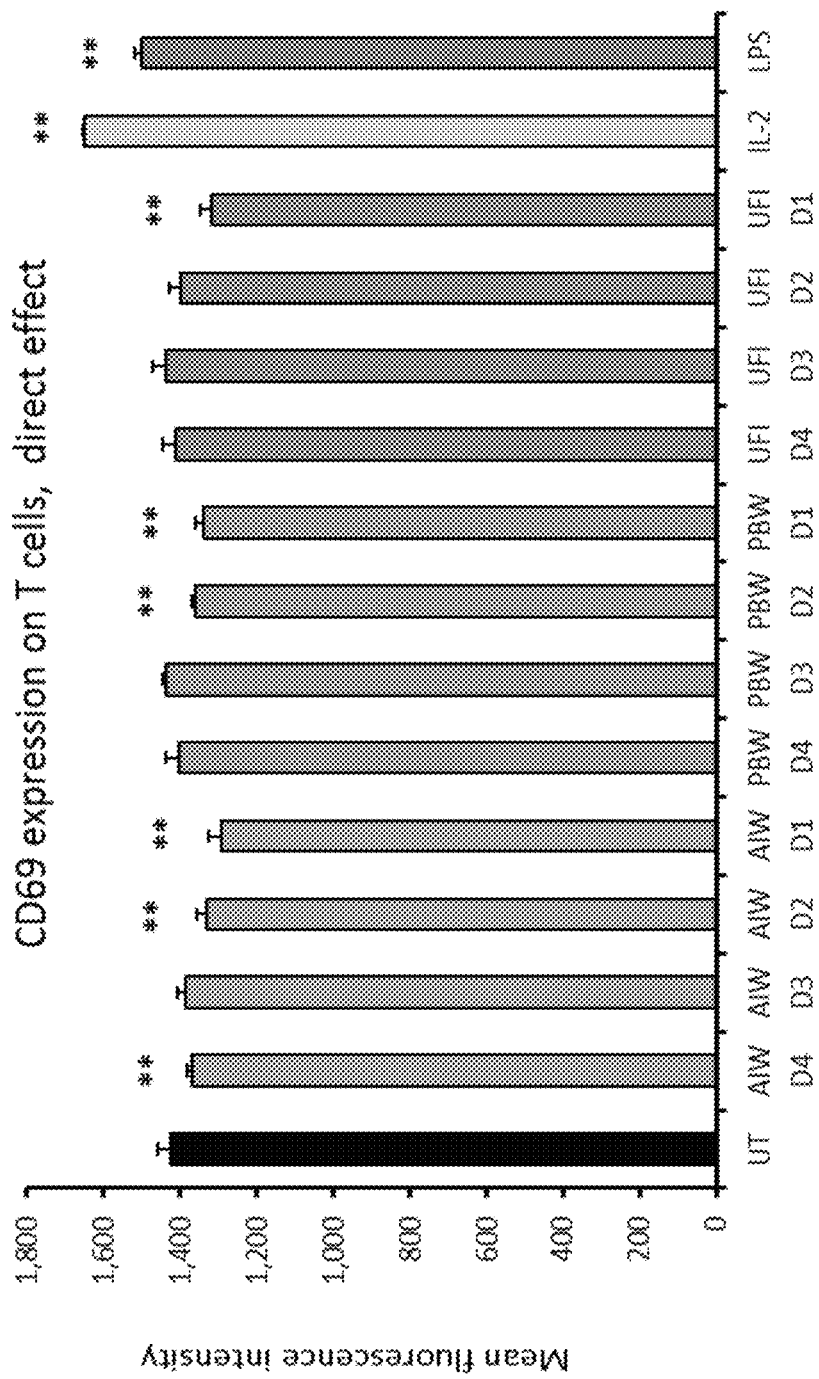
FIG. 7 shows raw data for CD69 expression on T lymphocytes (T cells). The data points represent the average±standard deviation of triplicate data sets.
Figure 8:
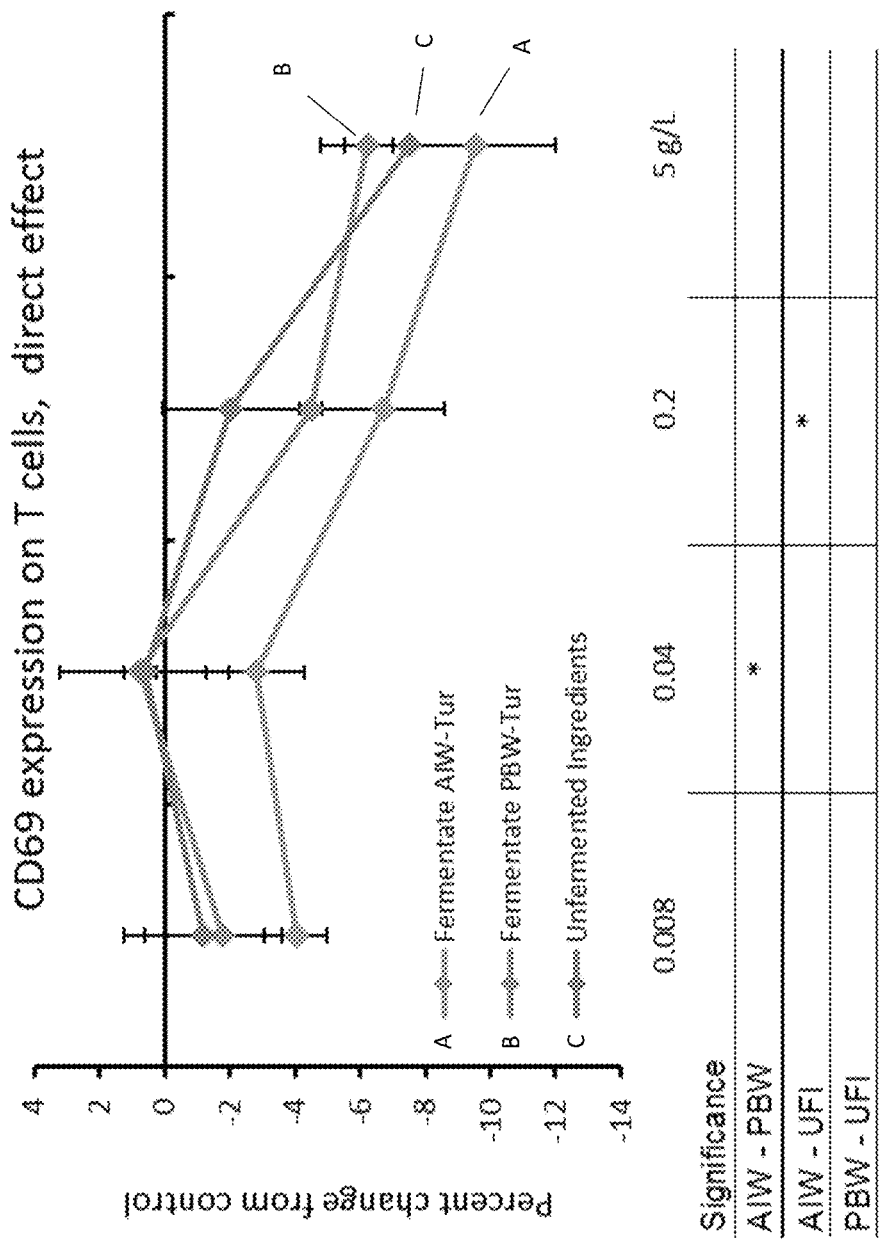
FIG. 8 shows a line graph of the data of FIG. 7 as percent change from the untreated control.

AIW-Tur, PBW-Tur, and UFI all triggered a reduction of CD69 expression on T lymphocytes, with AIW-Tur treatment showing the strongest reduction (FIGS. 7 and 8). The difference between AIW and UFI as well as PBW-Tur, was statistically significant.

Monocytes

Figure 9:
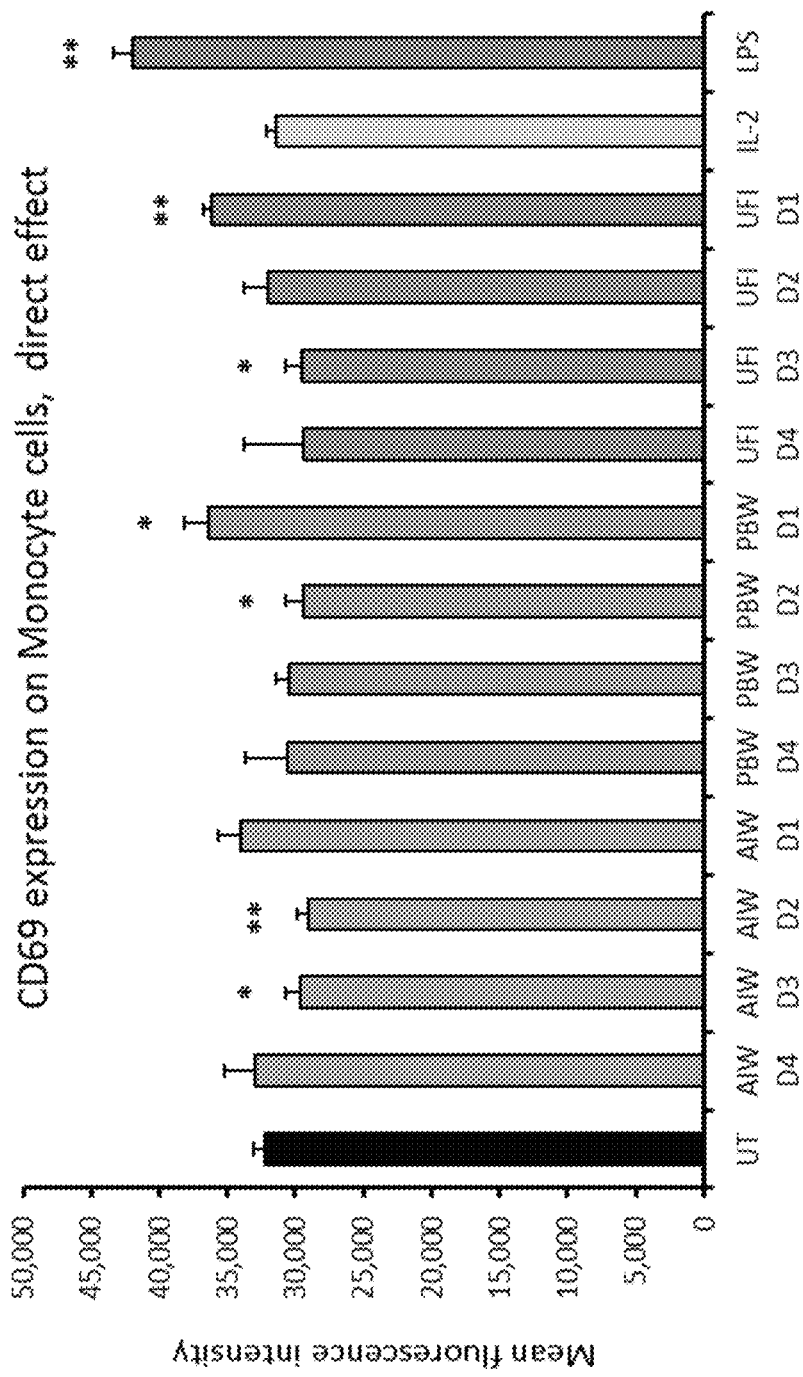
FIG. 9 shows raw data for CD69 expression on monocytes. The data points represent the average±standard deviation of triplicate data sets.
Figure 10:
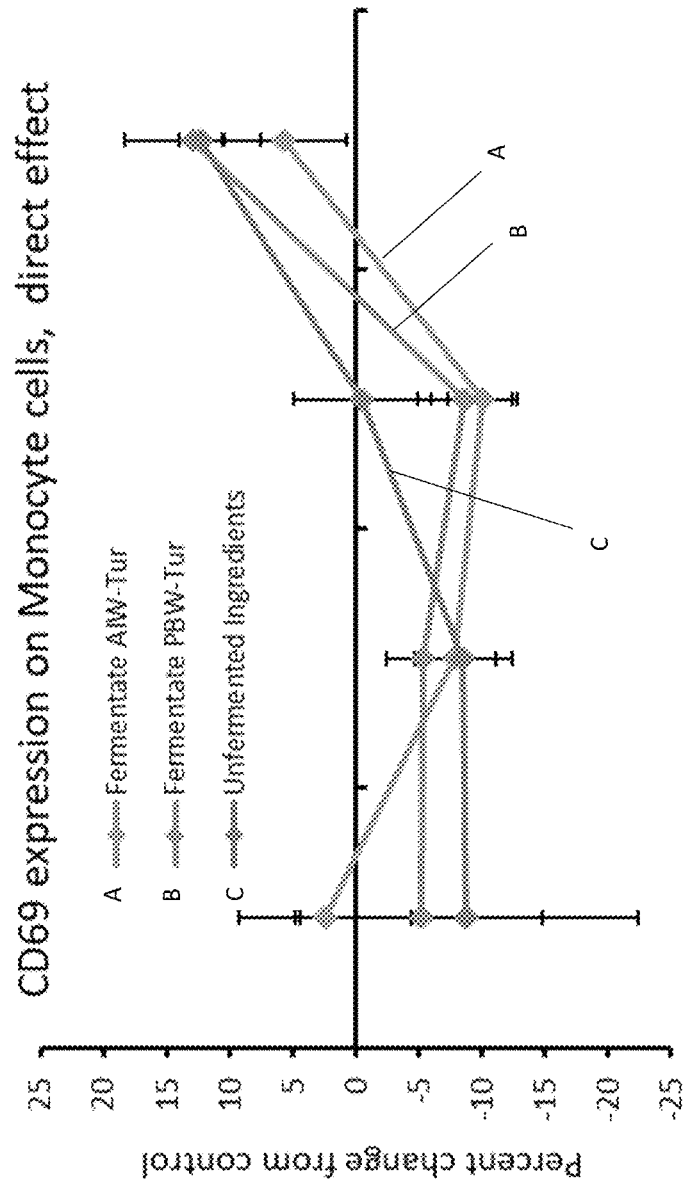
FIG. 10 shows a line graph of the data of FIG. 9 as percent change from the untreated control.

Monocytes express CD69, and inflammatory responses can be triggered via this cell surface receptor. At the highest dose tested, AIW-Tur, PBW-Tur, and UFI all triggered a mild increase in CD69 expression on monocytes (FIGS. 9 and 10). This increase was significant for PBW and UFI when compared to untreated cell cultures. At the second-highest dose tested, both AIW-Tur and PBW-Tur triggered a reduction in CD69 expression, while UFI had no effect. This reduction reached statistical trends when comparing each test product to UFI treatment. At the lowest dose the effects were less conclusive and did not show statistical differences.

Both the test products and UFI had effects on immune cell activation status, however, the test products had a stronger effect than UFI on reducing CD69 expression on monocytes.

Without being bound by any particular theory, the reduction of CD69 on NK cells suggest that the NK cells enter into a cell division mode, rather than an aggressive cytotoxic mode. In comparing the two fermented test products, AIW-Tur had a stronger effect than PBW-Tur on reducing CD69 expression on NK cells and T cells.

Example 7

Cytokine Production

Immune activating proinflammatory cytokines/chemokines, anti-inflammatory cytokines, anti-viral peptides, and growth factors were measured from the supernatant of PBMC cultures in the presence of aqueous or solid fractions of the test product or UFI. A 27-plex Luminex magnetic bead array and the MAGPIX® multiplexing system was used to test: IL-1beta, IL-1ra, IL-2, IL-4, IL-5, IL-6, IL-7, IL-8, IL-9, IL-10, IL-12 (p70), IL-13, IL-15, IL-17, cotaxin, basic FGF, G-CSF, GM-CSF, IFN-gamma, IP-10, MCP-1 (MCAF), MIP-1alpha, MIP-1beta, PDGF-BB, RANTES, TNF-alpha, and VEGF.

Regarding the pro-inflammatory cytokines/chemokines (IL-1-β, IL-5, IL-6, IL-8, IL-12 protein 70 (IL-12p70), IL-13, IL-17A, cotaxin, IFN-γ, IP-10, MCP-1 (MCAF), MIP-1α, MIP-1β, RANTES, and TNF-α), after 2 hours of culture, UFI had triggered a stronger increase than the test products (AIW-Tur and PBW-Tur), however, by 24 hours of culture the trend reversed with the two test products inducing higher levels of proinflammatory cytokines than UFI. The two test products performed similarly, with a slightly more robust cytokine induction by PBW-Tur. 24 hour results for several cytokines are shown in FIGS. 12A, 12B, 13A, 13B, 14A, 14B, 15A, 15B, 16A, 16B, 17A, 17B, 18A and 18B.

Figure 11A:
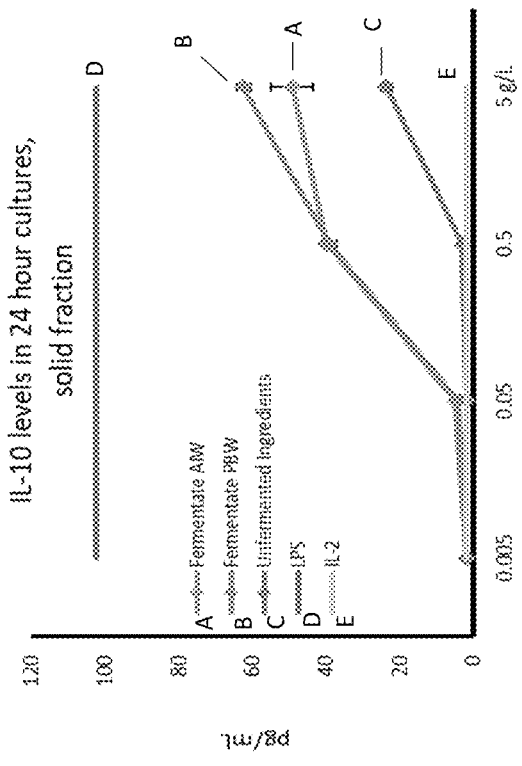
FIGS. 11A and 11B show interleukin 10 (IL-10) levels in PBMC cultures treated with the aqueous fractions (FIG.
Figure 11B:
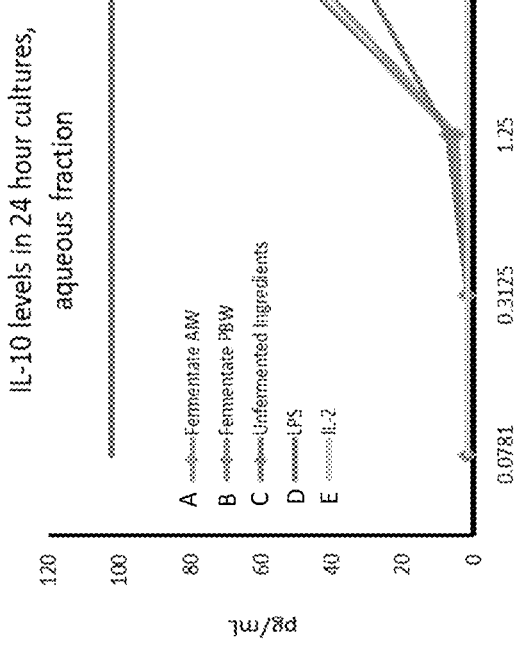

Regarding the anti-inflammatory cytokines (IL-1ra and IL-10), IL-1ra was comparable between the test products and UFI, however, the test products induced higher levels of IL-10 than UFI (FIGS. 11A and 11B).

Regarding cytokines with regulatory functions (both anti and pro-inflammatory effects), including IL-2, IL-4, IL-7, IL-9, and IL-15, after 2 hours of culture, the aqueous fraction of UFI induced higher levels of regulating cytokines than the aqueous fractions of the two test products. However, after 24 hours of culture, the aqueous fractions of the two test products induced higher levels of regulating cytokines than the aqueous fraction of UFI.

Growth factors, including Basic FGF (basic fibroblast growth factor), PDGF-BB (platelet derived growth factor subunit beta), VEGF (vascular endothelial growth factor), G-CSF (granulocyte colony-stimulating factor), and GM-CSF (granulocyte-macrophage colony stimulating factor), were also evaluated. After 2 hours of culture, the aqueous fraction of UFI induced higher levels of growth factors than the aqueous fractions of the two test products. After 24 hours of culture, the aqueous fractions of the two test products induced higher levels of growth factors than the aqueous fraction of UFI. The two test products performed similarly, with a slightly more robust cytokine induction by PBW-Tur. Growth factors involved in regenerative function were most robustly increased, with only minor effects of the inflammation-related GM-CSF. Both the test products and UFI triggered strong up-regulation of G-CSF, which is involved in stem cell mobilization.

The results show a more potent up-regulation of multiple cytokines by the fermented test products (both the aqueous and solid fractions) as compared to UFI. The test products also up-regulated the growth factor G-CSF more than UFI. This is interesting in view of the therapeutic role of G-CSF in stem cell mobilization for regenerative purposes. GM-CSF production can improve recovery after resolving the inflammatory state.

Example 8

Exemplary Production Process for a Liquid Product
The following instructions make a 16 fluid oz portion.
Day 1—Starter Culture
40 mLs of alkaline ionized water is added to a clean container along with the ingredients of Table 5.

TABLE 5

| Day 1 Ingredients | |
| --- | --- |
| Ingredient | Mass |
| Rice Bran | 2.5 g |
| Molasses | 2.5 g |
| Probiotic and SC yeast | 630 mg |

The probiotic and SC yeast is the GARDEN OF LIFE™ Raw Probiotics Ultimate Care capsule (Cat. No: 658010123334). The solution is gently mixed by inversion until the rice bran is wetted, the molasses dissolved, and probiotic powder dispersed. The container is placed in a dark place with a loosened lid.
Day 2—Aerobic Fermentation
The starter culture is transferred to a 0.5 L container that has been rinsed several times in alkaline ionized water. Then, the ingredients of Table 6 are added to the 0.5L container along with the starter culture.

TABLE 6

| Day 2 Ingredients | |
| --- | --- |
| Ingredient | Amount |
| Kelp Powder | 3 g |
| Rice Bran | 25 g |
| Molasses | 25 mg |
| Turmeric | 5 g |
| Alkaline Ionized Water | 400 mL |

The slurry is mixed vigorously by inversion until the bran is wetted and the molasses is dissolved. The bottle in placed in a dark cupboard with a loosened lid to let air in, but tight enough to keep airborne microbes out. The fermentate is stirred daily (close lid, mix by inversion, loosen lid again).
Day 7—Anaerobic Fermentation
After aerobic fermentation is complete, the ingredients of Table 6 are added to the mixture.

TABLE 7

| Day 7 Ingredients | |
| --- | --- |
| Ingredient | Mass |
| Bentonite Clay | 5 g |
| Sea Salt | 1 g |

The container is closed for anaerobic fermentation without stirring.
Day 15—Heating
After anaerobic fermentation, the mixture is homogenized well and heated to 150-160° F. for 2 to 3 hours.
Day 16—Add Natural Preservative
The fermentate is mixed well. Natural preservatives, such as Arborcide, are added.
Day 17—Harvest Fermentate
The product is ready for use.

Example 9

Production Process for a Spray Dried Product
The following example is a process for producing a spray dried product. Ingredients at each step are provided in Table 8 as % dry weight of total components of the composition.

TABLE 8

| Ingredients by % Dry Weight of Total Ingredients. | |
| --- | --- |
| Ingredients | % Composition (dry weight) |
| Starter Culture | |
| Rice bran | 3.50 |
| Molasses | 3.50 |
| Probiotic and SC yeast special blend | 0.90 |
| Aerobic Fermentation | |
| Kelp powder (5 capsules) | 4.30 |
| Rice bran | 35.70 |
| Molasses | 35.70 |
| Turmeric root powder | 7.80 |
| Anaerobic Fermentation | |
| Bentonite clay | 7.15 |
| Sea salt | 1.45 |
| Total | 100.00 |

The probiotic and SC yeast special blend includes *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophillus, Lactococcus lactis, Lactobacillus bulgaricus*, and *Saccharomyces cerevisiae*.
Starter Culture
20 kgs of alkaline ionized water ((pH=8 to 10) was added to a tank. Rice bran and molasses was slowly added and mixed for 2 hours. Then, the probiotic and SC yeast blend was added and mixed for two hours. The tank was covered and let sit overnight.
Aerobic Fermentation
150 kgs of alkaline ionized water (pH=8 to 10) was added to the mix from Part A. Kelp powder, rice bran, molasses, and turmeric root powder were slowly mixed in. The slurry was mixed for 4 hours. The tank was covered and let sit overnight. The slurry was stirred daily through the next 6 days.
Anaerobic Fermentation
30 kgs of alkaline ionized water (pH=8 to 10) was added to the mix from Part C. Bentonite clay and sea salt were slowly added and mixed for one hour. The tank was covered and let sit for 6 days at room temperature (approximately 22 to 28° C.).

Heating and Harvesting

After anaerobic fermentation, the fermentate was mixed well and heated to 160-170° F. for 4 hours. The product was homogenized well and spray dried into a powder.

Example 10

Comparison of Liquid Product Vs. Spray Dried Product

The liquid and spray-dried products were tested and compared to verify the efficacy of the production-type fermentates before and after spray drying. Both products were prepared according to Example 9, with the only difference being that the liquid product was not spray-dried at the conclusion of the process. The liquid product was prepared for addition to lab tests by centrifuging and harvesting the supernatant, which was sterile-filtered through a 0.22 micron cellulose-acetate membrane. Serial dilutions were prepared in physiological saline. The spray dried product was prepared by initially preparing a stock solution in physiological saline and allowing the powder to rehydrate under gentle agitation for 1 hour. The slush was centrifuged, and the supernatant was harvested and sterile-filtered through a 0.22 micron cellulose-acetate membrane. Serial dilutions were prepared in physiological saline.

The aqueous fraction containing metabolites produced during the fermentation process were tested in several of assays, including:

Cellular survival/viability assay;

Total antioxidant capacity assay;

Cell-based antioxidant protection assay;

Free radical formation by inflammatory cells assay.

Cellular Survival/Viability Assay

Mitochondrial metabolic activity of peripheral blood mononuclear cells was detected using a MTT assay, a colorimetric assay for assessing cell metabolic activity. The MTT assay utilizes a dye that changes color dependent on mitochondrial activity. A reduction in color intensity suggests reduced cellular viability, whereas an increase in color intensity suggests increased mitochondrial function.

Both the liquid and spray dried products were well-tolerated by the peripheral blood mononuclear cells in 24-hour culture (see, FIGS. 19A-C). A mild indication of stress was seen at higher doses of both products. The stress was slightly more pronounced for the liquid product. Neither product triggered a dramatic loss of cell viability, and metabolic activity in each culture remained higher than 80% (the metabolic activity of untreated cell cultures was set to 100% metabolic rate (100% viability)).

Total Antioxidant Capacity Assay

Folin-Ciocalteu phenol reagent was added to serial dilutions of each test sample. Samples were thoroughly mixed and incubated for 5 minutes. Sodium carbonate was added. The reaction continued for 30 minutes at 37° C. Color intensity was documented by measuring the optical absorbance at 765 nm in a colorimetric plate reader. Gallic acid was used as a reference standard.

Both products showed antioxidant capacity (see, FIGS. 20A-20C). When calculating antioxidant capacity on the basis of dry weight, the spray dried product had a slightly higher total antioxidant capacity than the liquid product. Table 9 reports Gallic Acid Equivalents (GAE) per gram product.

TABLE 9

| Cellular Antioxidant Capacity | |
| --- | --- |
| Sample | GAE |
| Liquid product | 0.34 mL/L |
| Liquid product (dry weight adjusted) | 2.1 g/L |
| Spray dried product | 2.6 g/L |

Cell-Based Antioxidant Protection

The CAP-e bioassay was used to detect the presence of antioxidants that are able to cross the cell membrane, enter the cell, and provide antioxidant protection under conditions of oxidative stress.

Human red blood cells (RBCs) were washed in physiological saline and then incubated with the spray dried product or liquid product (or no product for the controls). After incubation, RBCs were washed to remove compounds that were not absorbed by the cells. The cells were then loaded with DCF-DA dye, which fluoresces upon exposure to reactive oxygen species, and were challenged with 2,2'-azobis(2-amidinopropane) dihydrochloride (AAPH) to induce oxidative stress. Fluorescence intensity prior to exposure to oxidative stress was used to calculate the percent inhibition of cellular oxidative stress. Control treatments included untreated cells (baseline reading) and RBCs treated with AAPH alone (maximum oxidative damage). Reduced fluorescence intensity of RBCs exposed to AAPH after pre-incubation with a test product indicates that the test product contains antioxidants available to penetrate into the cells and protect these from oxidative damage.

CAP-e units are presented in Table 10 below. The fluorescence intensity in cell cultures treated with test products prior to exposure to oxidative stress was used to calculate the percent inhibition of cellular oxidative stress. The unit is micromoles gallic acid (GA) per mL or gram of test product, calculated using a standard curve of known gallic acid (GA).

At higher doses, both products caused some stress in the cell cultures. This is often seen with potent bioactive natural products, where higher doses may overwhelm the cellular integrity. However, at lower doses, both products provided cellular antioxidant protection (see, FIGS. 21A-21C). The spray-dried product provided better protection than the liquid product, confirming that the spray-drying process did not destroy compounds responsible for cellular antioxidant protection, but rather showed an increase in the level of antioxidants available to enter into and protect cells from oxidative stress.

TABLE 10

| Cellular Antioxidant Protection | |
| --- | --- |
| Sample | CAP-e units |
| Liquid product | 2* µM GA/mL |
| Liquid product (dry weight adjusted) | 12* µM GA/gram |
| Spray dried product | 17 µM GA/gram |

*IC50 was achieved based on data points with some display of cell lysing. Therefore, even though product showed antioxidant protection, a CAP-e value is calculated as an estimate only.

Free Radical Formation by Inflammatory Cells

Human mononuclear (monocytes) and polymorphonuclear (PMN) phagocytic cells in whole blood samples were used to test the effects of the spray dried and liquid products on ROS formation. Testing was performed on cells from a healthy blood donor. Samples of blood were incubated with the test products. Then, the cells were loaded with the dihydrorhodamine (DHR) dye, which turns fluorescent upon exposure to ROS. Formation of ROS was triggered by addition of the bacterial peptide f-Met-Leu-Phe (fMLP). Samples were treated with a lysis buffer to eliminate most of the red blood cells in the samples, after which the samples were fixed in formalin. The fluorescence intensity of the monocytes and PMN cells was evaluated by flow cytometry. The fluorescence intensity of untreated control cells served as a baseline and PMN cells treated with fMLP alone serve as a positive control. If the DHR fluorescence intensity of cells exposed to a test product, and subsequently exposed to fMLP, is reduced compared to fMLP alone, this indicates that the test product has anti-inflammatory effects.

The results were analyzed in two different ways for each cell type:
1. The mean fluorescence intensity for the DHR reporter dye across the cell population was analyzed separately for monocytes (FIGS. 24A-24C) and PMN cells (FIGS. 22A-22C).
2. The percentage of cells engaging in immune defensive behavior by producing ROS, as indicated by % cells being positive for the dihydrorhodamine (DHR) reporter dye, was analyzed separately for monocytes (FIGS. 25A-25C) and PMN cells (FIGS. 23A-23C).

Additional data graphs are shown for lymphocytes (FIGS. 26A-26C). These cells contain some sub-populations that can engage in recognition of the bacterial peptide and respond by ROS formation.

Both the spray dried and the liquid products demonstrated antioxidant capacity and the ability to provide cellular antioxidant protection from free radical stress, suggesting that some of the antioxidants in the products are bioavailable at the cellular level. In addition, both the spray-dried and the liquid products increased immune defense activity of phagocytic cells (PMN cells and monocytes/macrophages); the phagocytic cells were more active in terms of ROS formation in response to a bacterial peptide, and a higher number of phagocytes engaged in this immune defense behavior after being treated with the products.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. A method for producing an immunomodulatory product, comprising
performing steps a-g in order:
   a) preparing a starter culture comprising:
      i) rice bran,
      ii) molasses, and
      iii) a blend of probiotic bacteria and yeast, wherein the blend comprises *Lactobacillus acidophilus, Lactobacillus plantarum, Lactobacillus rhamnosus, Lactobacillus fermentum, Lactobacillus casei, Bifidobacterium bifidum, Bifidobacterium longum, Bifidobacterium breve, Bifidobacterium animalis* subsp. *lactis, Streptococcus thermophilus, Lactococcus lactis, Lactobacillus bulgaricus,* and *Saccharomyces cerevisiae;*
   b) aerobically fermenting the starter culture for about one day, thereby forming an aerobically fermented starter culture;
   c) adding rice bran, molasses, turmeric, and kelp powder to the aerobically fermented starter culture to form a slurry comprising:
      i) 35% to 45% by dry weight rice bran,
      ii) 35% to 45% by dry weight molasses,
      iii) 7.5% to 9% by dry weight turmeric, and
      iv) 4% to 6% by dry weight kelp powder;
   d) aerobically fermenting the slurry for about 6 days, thereby forming an aerobic fermentate;
   e) adding bentonite clay and sea salt to the aerobic fermentate to form an intermediate composition comprising:
      i) 6% to 9% by dry weight bentonite clay, and
      ii) 1% to 2% by dry weight sea salt;
   f) fermenting the intermediate composition anaerobically for about 6 days, thereby forming an anaerobic fermentate; and
   g) heating the anaerobic fermentate to about 160 to 170° F. for about 3 to about 5 hours;
thereby forming the immunomodulatory product.

2. The method of claim 1, further comprising spray drying the immunomodulatory product into a powder.

3. A product produced by the method of claim 1.

4. A composition comprising the product of claim 3.

5. The composition of claim 4, further comprising glucosamine, collagen, immune-supportive fungi, and/or mammalian colostrum.

6. The composition of claim 4, wherein the composition is an animal feed.

7. A method of increasing function of natural killer cells, decreasing T cell activation, altering cytokine expression, and/or altering CD69 expression on immune cells, in a subject, comprising:
administering to the subject an effective amount of the composition of claim 4, thereby increasing function of natural killer cells, decreasing T cell activation, altering cytokine expression and/or altering CD69 expression on immune cells in the subject, respectively.

8. The method of claim 1, wherein the immunomodulatory product increases a function of natural killer cells, decreases T cell activation, alters cytokine expression, and/or alters CD69 expression on immune cells.

9. The method of claim 1, wherein:
step a), wherein the starter culture comprises:
   i) about 3.5% by dry weight rice bran,
   ii) about 3.5% by dry weight molasses, and
   iii) the blend of probiotic bacteria and yeast;
step c), wherein the slurry comprises:
   i) about 35% by dry weight rice bran,
   ii) about 35% by dry weight molasses,
   iii) about 7.5% by dry weight turmeric, and
   iv) about 4.5% dry weight kelp powder; and
step e), wherein the intermediate composition comprises:
   i) about 7% by dry weight bentonite clay, and
   ii) about 1% by dry weight sea salt.

10. The method of claim 9, further comprising spray drying the immunomodulatory product into a powder.

11. The method of claim 10, further comprising mixing the powder into animal feed.

12. The method of claim 11, wherein the animal feed is food for dogs, cats, or horses.

13. The method of claim 9, further comprising adding glucosamine, collagen, immune-supportive fungi, and/or mammalian colostrum to the immunomodulatory product.

14. The method of claim 13, further comprising mixing the immunomodulatory product into animal feed.

15. The method of claim 14, wherein the animal feed is food for dogs, cats, or horses.

* * * * *